(12) United States Patent
Morita et al.

(10) Patent No.: US 12,319,718 B2
(45) Date of Patent: Jun. 3, 2025

(54) MODIFIED FIBROIN

(71) Applicant: Spiber Inc., Tsuruoka (JP)

(72) Inventors: Keisuke Morita, Tsuruoka (JP); Yunosuke Abe, Tsuruoka (JP); Hiroyuki Nakamura, Tsuruoka (JP); Shota Togashi, Tsuruoka (JP); Tetsuo Asakura, Fuchu (JP)

(73) Assignee: Spiber Inc., Tsuruoka (JP)

( * ) Notice: Subject to any disclaimer, the term of this patent is extended or adjusted under 35 U.S.C. 154(b) by 858 days.

(21) Appl. No.: 17/421,243

(22) PCT Filed: Jan. 9, 2020

(86) PCT No.: PCT/JP2020/000535
§ 371 (c)(1),
(2) Date: Jul. 7, 2021

(87) PCT Pub. No.: WO2020/145363
PCT Pub. Date: Jul. 16, 2020

(65) Prior Publication Data
US 2022/0119463 A1    Apr. 21, 2022

(30) Foreign Application Priority Data
Jan. 9, 2019   (JP) ................................ 2019-001812

(51) Int. Cl.
| | | |
|---|---|---|
| *C07K 14/435* | (2006.01) | |
| *C12N 15/63* | (2006.01) | |
| *C12P 21/02* | (2006.01) | |
| *D01F 4/02* | (2006.01) | |

(52) U.S. Cl.
CPC ........ *C07K 14/43586* (2013.01); *C12N 15/63* (2013.01); *C12P 21/02* (2013.01); *D01F 4/02* (2013.01)

(58) Field of Classification Search
CPC .............. C07K 14/43586; C12N 15/63; C12P 21/02; D01F 4/02
See application file for complete search history.

(56) References Cited

U.S. PATENT DOCUMENTS

| | | | |
|---|---|---|---|
| 5,245,012 A | 9/1993 | Lombari et al. | |
| 10,899,792 B2 * | 1/2021 | Osawa ..................... | C12P 21/00 |
| 2017/0214520 A1 | 7/2017 | Teper et al. | |
| 2019/0135880 A1 | 5/2019 | Morita et al. | |
| 2019/0186050 A1 | 6/2019 | Numata et al. | |
| 2019/0233481 A1 | 8/2019 | Morita et al. | |
| 2020/0207817 A1 | 7/2020 | Morita et al. | |

FOREIGN PATENT DOCUMENTS

| | | |
|---|---|---|
| CN | 101018806 A | 8/2007 |
| CN | 101395178 A | 3/2009 |
| CN | 102532295 A | 7/2012 |
| CN | 109071619 A | 12/2018 |
| EP | 3859056 A1 | 8/2021 |
| JP | 2014-502140 A | 1/2014 |
| WO | 1991016351 A | 10/1991 |
| WO | 2006/008163 A2 | 1/2006 |
| WO | 2007/078239 A2 | 7/2007 |
| WO | 2012050919 A2 | 4/2012 |
| WO | 2013065651 A1 | 5/2013 |
| WO | 2015042164 A2 | 3/2015 |
| WO | 2017/222034 A1 | 12/2017 |
| WO | 2018034111 A1 | 2/2018 |
| WO | 2018164190 A1 | 9/2018 |
| WO | 2018/221498 A1 | 12/2018 |
| WO | 2018235958 A1 | 12/2018 |
| WO | 2019022163 A1 | 1/2019 |

(Continued)

OTHER PUBLICATIONS

Lee et al., Mechanical behavior comparison of spider and silkworm silks using molecular dynamics at atomic scale, Phys Chem Chem Phys 18, 4814. (Year: 2016).*
Narita, Kozo, "Reaction of Anhydrous Formic Acid with Proteins", Journal of American Chemical Society, Apr. 5, 1959, pp. 1751-1756.
"Artificial synthesis spider silk protein MASP2", Mar. 15, 2017, pp. 1-83, English Abstract.
Zhoughu, Wu, "The research of secondary structure and spinning mechanism of recombinant spider silk protein", May 15, 2017, pp. 1-57, English Abstract.
Wang et al., "Research Progress in Spidroin Gene Recombinant Expression", China Academic Journal Electronic Publishing House, Mar. 30, 2017, pp. 24-27, English Abstract.
Patent Cooperation Treaty, International Search Report issued in PCT/JP2020/000535, Jul. 22, 2021, pp. 1-11.
Patent Cooperation Treaty, International Preliminary Report on Patentability issued in PCT/JP2020/000535, Mar. 17, 2020, pp. 1-3.

(Continued)

*Primary Examiner* — Suzanne M Noakes
*Assistant Examiner* — Ciara A McKnight
(74) *Attorney, Agent, or Firm* — Studebaker Brackett PLLC

(57) ABSTRACT

The present invention relates to a modified fibroin including a domain sequence represented by Formula 1: [(A)$_n$ motif-REP]$_m$ or Formula 2: [(A)$_n$ motif-REP]$_m$-(A)$_n$ motif, and having a serine residue content rate of less than 5.5%.

[In Formula 1 and Formula 2, the (A)$_n$ motif represents an amino acid sequence consisting of 4 to 27 amino acid residues, and the number of alanine residues with respect to the total number of amino acid residues in the (A)$_n$ motif is 80% or more. REP represents an amino acid sequence consisting of 10 to 200 amino acid residues. m represents an integer of 10 to 300. The plurality of (A)$_n$ motifs may be the same amino acid sequence or different amino acid sequences. A plurality of REPs may be the same amino acid sequence or different amino acid sequences.]

24 Claims, 2 Drawing Sheets
Specification includes a Sequence Listing.

(56) References Cited

FOREIGN PATENT DOCUMENTS

WO  WO-2019054506 A1 * 3/2019  ............... A61K 8/64
WO  WO-2020067573 A1 * 4/2020

OTHER PUBLICATIONS

Lazaris et al., "Spider Silk Fibers Spun from Soluble Recombinant Silk Produced in Mammalian Cells.", Science, 2002, pp. 472-476, vol. 295(5554).
European Patent Office, Extended European Search Report issued in EP 20738473.6, Apr. 21, 2023, pp. 1-45.
Ko Jae Sang et al, "Effect of Sericin Content on the Structural Characteristics and Properties of Electro-spun Regenerated Silk", Ffibers and Polymers, The Korean Fiber Society, Seoul, Mar. 23, 2018, pp. 507-514, XP036465718, vol. 19(3).

* cited by examiner

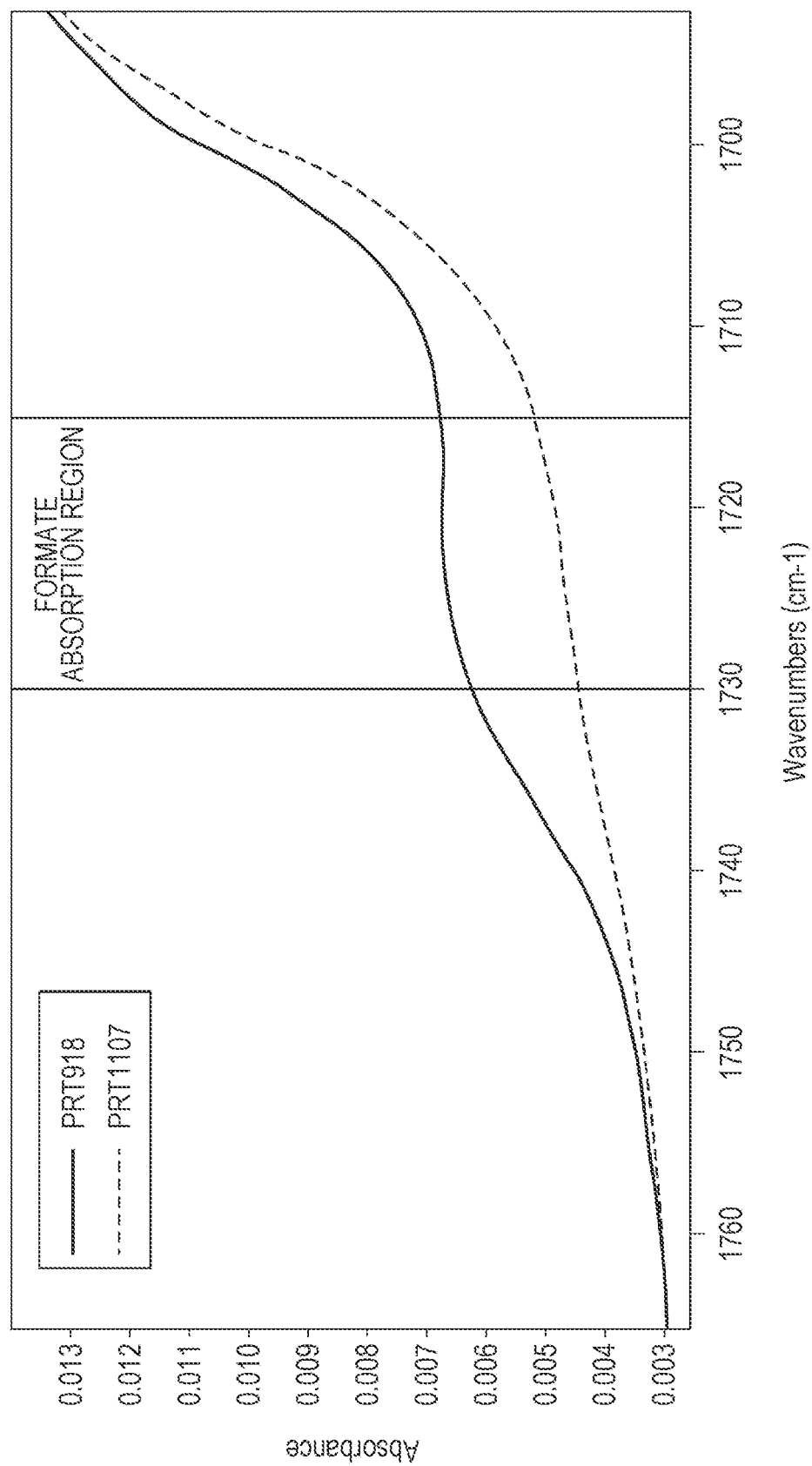

SEQUENCE LISTING

<160> NUMBER OF SEQ ID NOS: 28

<210> SEQ ID NO 1
<211> LENGTH: 590
<212> TYPE: PRT
<213> ORGANISM: Artificial Sequence
<220> FEATURE:
<223> OTHER INFORMATION: Met-PRT918

<400> SEQUENCE: 1

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
                20                  25                  30

Ile Ser Gly Ile Tyr Gly Pro Gly Val Phe Gly Pro Gly Val Phe Gly
            35                  40                  45

Pro Gly Ser Ser Ala Ala Ala Ala Gly Pro Gly Ile Tyr Gly Pro
    50                  55                  60

Gly Val Phe Gly Pro Ser Ala Ser Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
                100                 105                 110

Gly Ile Tyr Gly Ser Gly Pro Gly Val Phe Gly Pro Tyr Gly Ser Ala
            115                 120                 125

Ala Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Gly Ser Gly Val Phe Gly Pro
                165                 170                 175

Gly Ile Tyr Gly Pro Tyr Ala Ser Ala Ala Ala Ala Gly Ile Tyr
                180                 185                 190

Gly Ser Gly Pro Gly Val Phe Gly Pro Tyr Gly Pro Gly Ile Ser Gly
            195                 200                 205

Ser Gly Val Phe Gly Pro Gly Val Phe Gly Pro Tyr Ala Ser Ala Ala
210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
            260                 265                 270

Tyr Gly Pro Gly Val Phe Gly Pro Gly Ile Ser Ala Ala Ala Ala Ala
            275                 280                 285

Gly Pro Gly Val Phe Gly Pro Tyr Gly Pro Gly Ala Ser Ala Ala Ala
            290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
            325                 330                 335

Ser Ala Ala Ala Ala Gly Ile Tyr Gly Pro Gly Val Phe Gly Pro
            340                 345                 350

Tyr Gly Pro Gly Ile Ser Ala Ala Ala Ala Gly Ile Tyr Val Phe
            355                 360                 365

Gly Pro Gly Val Phe Gly Pro Tyr Gly Pro Gly Ala Ser Gly Pro Gly
            370                 375                 380

Val Phe Gly Pro Tyr Gly Pro Gly Ala Ser Ala Ala Ala Ala Gly
385                 390                 395                 400

Pro Gly Ile Tyr Gly Pro Gly Val Phe Gly Pro Ser Ala Ser Ala Ala
            405                 410                 415

Ala Ala Ala Gly Ile Tyr Gly Ser Gly Pro Gly Ile Tyr Gly Pro Tyr
            420                 425                 430

Gly Pro Gly Ile Ser Gly Pro Gly Ser Gly Val Phe Gly Ile Gly Pro
            435                 440                 445

Tyr Gly Pro Gly Ala Ser Ala Ala Ala Ala Gly Ile Tyr Gly Pro
            450                 455                 460

Gly Val Phe Gly Pro Tyr Gly Pro Gly Ile Ser Ala Ala Ala Ala
465                 470                 475                 480

Gly Pro Gly Ser Gly Ile Tyr Gly Pro Gly Ala Ser Gly Ile Asn Gly
            485                 490                 495

Pro Gly Ser Gly Ile Tyr Gly Pro Gly Val Phe Gly Pro Gly Ile Ser
            500                 505                 510

Ala Ala Ala Ala Ala Gly Ile Tyr Val Phe Gly Pro Gly Val Phe Gly
            515                 520                 525

Pro Tyr Gly Pro Gly Ala Ser Ala Ala Ala Ala Gly Ile Tyr Gly
            530                 535                 540

Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala
            565                 570                 575

Ala Ala Gly Pro Gly Ser Gly Val Phe Gly Pro Gly Ala Ser
            580                 585                 590

<210> SEQ ID NO 2
<211> LENGTH: 590

<212> TYPE: PRT
<213> ORGANISM: Artificial Sequence
<220> FEATURE:
<223> OTHER INFORMATION: Met-PRT1104

<400> SEQUENCE: 2

```
Met Gly Pro Gly Gln Gln Gly Pro Tyr Gly Pro Gly Ala Gly Ala Ala
1               5                   10                  15

Ala Ala Ala Gly Gln Asn Gly Pro Gly Ala Gly Gln Gln Gly Pro Gly
            20                  25                  30

Gln Ala Gly Gln Tyr Gly Pro Gly Gln Gln Gly Pro Gly Gln Gln Gly
        35                  40                  45

Pro Gly Ala Gly Ala Ala Ala Ala Gly Pro Gly Gln Tyr Gly Pro
    50                  55                  60

Gly Gln Gln Gly Pro Ser Ala Gly Ala Ala Ala Ala Gly Pro Gly
65                  70                  75                  80

Ala Gly Gln Gln Gly Pro Gly Ala Ala Gly Gln Tyr Gly Pro Gly Gln
                85                  90                  95

Gln Gly Pro Gly Gln Gln Gly Pro Gly Ala Gly Ala Ala Ala Ala
                100                 105                 110

Gly Gln Tyr Gly Ala Gly Pro Gly Gln Gln Gly Pro Tyr Gly Gly Ala
        115                 120                 125

Ala Ala Ala Ala Gly Pro Gly Ala Gly Gln Tyr Gly Gln Gly Pro Tyr
    130                 135                 140

Gly Pro Gly Ala Ala Gly Pro Gly Gln Tyr Gly Pro Gly Gln Gln Gly
145                 150                 155                 160

Pro Ser Ala Gly Ala Ala Ala Ala Gly Gln Gln Gly Pro
                165                 170                 175

Gly Gln Tyr Gly Pro Tyr Ala Gly Ala Ala Ala Ala Gly Gln Tyr
        180                 185                 190

Gly Ala Gly Pro Gly Gln Gln Gly Pro Tyr Gly Pro Gly Gln Ala Gly
        195                 200                 205

Ala Gly Gln Gln Gly Pro Gly Gln Gln Gly Pro Tyr Ala Gly Ala Ala
    210                 215                 220

Ala Ala Ala Gly Pro Gly Gln Gln Gly Pro Tyr Gly Pro Gly Ala Gly
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ala Gly Gln Asn Gly Pro Gly Ala Gly Gln
        260                 265                 270

Tyr Gly Pro Gly Gln Gln Gly Pro Gln Gly Ala Ala Ala Ala
        275                 280                 285

Gly Pro Gly Gln Gln Gly Pro Tyr Gly Pro Gly Ala Gly Ala Ala Ala
        290                 295                 300

Ala Ala Gly Gln Tyr Gly Pro Gly Gln Gln Gly Pro Gly Gln Tyr Gly
305                 310                 315                 320

Pro Gly Ala Ala Gly Pro Gly Gln Gln Gly Pro Tyr Gly Pro Gly Ala
            325                 330                 335

Gly Ala Ala Ala Ala Gly Gln Tyr Gly Pro Gly Gln Gln Gly Pro
            340                 345                 350

Tyr Gly Pro Gly Gln Gly Ala Ala Ala Ala Gly Gln Tyr Gln Gln
        355                 360                 365

Gly Pro Gly Gln Gln Gly Pro Tyr Gly Pro Gly Ala Ala Gly Pro Gly
        370                 375                 380
```

```
Gln Gln Gly Pro Tyr Gly Pro Gly Ala Gly Ala Ala Ala Ala Gly
385                 390                 395                 400

Pro Gly Gln Tyr Gly Pro Gly Gln Gln Gly Pro Ser Ala Gly Ala Ala
                405                 410                 415

Ala Ala Ala Gly Gln Tyr Gly Ala Gly Pro Gly Gln Tyr Gly Pro Tyr
            420                 425                 430

Gly Pro Gly Gln Ala Gly Pro Gly Ala Gly Gln Gln Gly Gln Gly Pro
        435                 440                 445

Tyr Gly Pro Gly Ala Gly Ala Ala Ala Ala Ala Gly Gln Tyr Gly Pro
        450                 455                 460

Gly Gln Gln Gly Pro Tyr Gly Pro Gly Gln Gly Ala Ala Ala Ala
465                 470                 475                 480

Gly Pro Gly Ala Gly Gln Tyr Gly Pro Gly Ala Ala Gly Gln Asn Gly
            485                 490                 495

Pro Gly Ala Gly Gln Tyr Gly Pro Gly Gln Gln Gly Pro Gly Gln Gly
            500                 505                 510

Ala Ala Ala Ala Ala Gly Gln Tyr Gln Gln Gly Pro Gly Gln Gln Gly
            515                 520                 525

Pro Tyr Gly Pro Gly Ala Gly Ala Ala Ala Ala Gly Gln Tyr Gly
530                 535                 540

Ala Gly Pro Gly Gln Gln Gly Pro Tyr Gly Pro Gly Gln Ala Gly Ala
545                 550                 555                 560

Gly Gln Gln Gly Pro Gly Gln Gln Gly Pro Tyr Ala Gly Ala Ala Ala
            565                 570                 575

Ala Ala Gly Pro Gly Ala Gly Gln Gln Gly Pro Gly Ala Ser
            580                 585                 590

<210> SEQ ID NO 3
<211> LENGTH: 590
<212> TYPE: PRT
<213> ORGANISM: Artificial Sequence
<220> FEATURE:
<223> OTHER INFORMATION: Met-PRT1105

<400> SEQUENCE: 3

Met Gly Pro Gly Val Phe Gly Pro Tyr Gly Pro Gly Ala Gly Ala Ala
1                   5                   10                  15

Ala Ala Ala Gly Ile Asn Gly Pro Gly Ala Gly Val Phe Gly Pro Gly
                20                  25                  30

Ile Ala Gly Ile Tyr Gly Pro Gly Val Phe Gly Pro Gly Val Phe Gly
            35                  40                  45

Pro Gly Ala Gly Ala Ala Ala Ala Gly Pro Gly Ile Tyr Gly Pro
        50                  55                  60

Gly Val Phe Gly Pro Gly Ala Ala Ala Ala Ala Gly Pro Gly
65                  70                  75                  80

Ala Gly Val Phe Gly Pro Gly Ala Gly Ile Tyr Gly Pro Gly Val
            85                  90                  95

Phe Gly Pro Gly Val Phe Gly Pro Gly Ala Gly Ala Ala Ala Ala Ala
            100                 105                 110

Gly Ile Tyr Gly Ala Gly Pro Gly Val Phe Gly Pro Tyr Gly Gly Ala
            115                 120                 125

Ala Ala Ala Ala Gly Pro Gly Ala Gly Ile Tyr Gly Ile Gly Pro Tyr
            130                 135                 140

Gly Pro Gly Ala Ala Gly Pro Gly Ile Tyr Gly Pro Gly Val Phe Gly
145                 150                 155                 160
```

```
Pro Gly Ala Gly Ala Ala Ala Ala Gly Ala Val Phe Gly Pro
            165                 170                 175

Gly Ile Tyr Gly Pro Tyr Ala Gly Ala Ala Ala Gly Ile Tyr
            180                 185                 190

Gly Ala Gly Pro Gly Val Phe Gly Pro Tyr Gly Pro Gly Ile Ala Gly
            195                 200                 205

Ala Gly Val Phe Gly Pro Gly Val Phe Gly Pro Tyr Ala Gly Ala Ala
210                 215                 220

Ala Ala Ala Gly Pro Gly Val Phe Gly Pro Tyr Gly Pro Gly Ala Gly
225                 230                 235                 240

Ala Ala Ala Ala Ala Gly Ile Tyr Gly Tyr Gly Pro Gly Val Phe Gly
            245                 250                 255

Pro Tyr Gly Pro Gly Ala Ala Gly Ile Asn Gly Pro Gly Ala Gly Ile
            260                 265                 270

Tyr Gly Pro Gly Val Phe Gly Pro Gly Ile Gly Ala Ala Ala Ala
            275                 280                 285

Gly Pro Gly Val Phe Gly Pro Tyr Gly Pro Gly Ala Gly Ala Ala Ala
            290                 295                 300

Ala Ala Gly Ile Tyr Gly Pro Gly Val Phe Gly Pro Gly Ile Tyr Gly
305                 310                 315                 320

Pro Gly Ala Ala Gly Pro Gly Val Phe Gly Pro Tyr Gly Pro Gly Ala
            325                 330                 335

Gly Ala Ala Ala Ala Gly Ile Tyr Gly Pro Gly Val Phe Gly Pro
            340                 345                 350

Tyr Gly Pro Gly Ile Gly Ala Ala Ala Ala Gly Ile Tyr Val Phe
            355                 360                 365

Gly Pro Gly Val Phe Gly Pro Tyr Gly Pro Gly Ala Ala Gly Pro Gly
            370                 375                 380

Val Phe Gly Pro Tyr Gly Pro Gly Ala Gly Ala Ala Ala Ala Gly
385                 390                 395                 400

Pro Gly Ile Tyr Gly Pro Gly Val Phe Gly Pro Gly Ala Gly Ala Ala
            405                 410                 415

Ala Ala Ala Gly Ile Tyr Gly Ala Gly Pro Gly Ile Tyr Gly Pro Tyr
            420                 425                 430

Gly Pro Gly Ile Ala Gly Pro Gly Ala Gly Val Phe Gly Ile Gly Pro
            435                 440                 445

Tyr Gly Pro Gly Ala Gly Ala Ala Ala Ala Gly Ile Tyr Gly Pro
            450                 455                 460

Gly Val Phe Gly Pro Tyr Gly Pro Gly Ile Gly Ala Ala Ala Ala
465                 470                 475                 480

Gly Pro Gly Ala Gly Ile Tyr Gly Pro Gly Ala Ala Gly Ile Asn Gly
            485                 490                 495

Pro Gly Ala Gly Ile Tyr Gly Pro Gly Val Phe Gly Pro Gly Ile Gly
            500                 505                 510

Ala Ala Ala Ala Gly Ile Tyr Val Phe Gly Pro Gly Val Phe Gly
            515                 520                 525

Pro Tyr Gly Pro Gly Ala Gly Ala Ala Ala Ala Gly Ile Tyr Gly
            530                 535                 540

Ala Gly Pro Gly Val Phe Gly Pro Tyr Gly Pro Gly Ile Ala Gly Ala
545                 550                 555                 560

Gly Val Phe Gly Pro Gly Val Phe Gly Pro Tyr Ala Gly Ala Ala Ala
            565                 570                 575
```

Ala Ala Gly Pro Gly Ala Gly Val Phe Gly Pro Gly Ala Gly
            580                 585                 590

<210> SEQ ID NO 4
<211> LENGTH: 590
<212> TYPE: PRT
<213> ORGANISM: Artificial Sequence
<220> FEATURE:
<223> OTHER INFORMATION: Met-PRT1103

<400> SEQUENCE: 4

Met Gly Pro Gly Gln Gln Gly Pro Phe Gly Pro Gly Ala Gly Ala Ala
1               5                   10                  15

Ala Ala Ala Gly Gln Asn Gly Pro Gly Ala Gly Gln Gln Gly Pro Gly
            20                  25                  30

Gln Ala Gly Gln Phe Gly Pro Gly Gln Gln Gly Pro Gly Gln Gln Gly
        35                  40                  45

Pro Gly Ala Gly Ala Ala Ala Ala Gly Pro Gly Gln Phe Gly Pro
    50                  55                  60

Gly Gln Gln Gly Pro Ser Ala Gly Ala Ala Ala Ala Gly Pro Gly
65                  70                  75                  80

Ala Gly Gln Gln Gly Pro Gly Ala Ala Gly Gln Phe Gly Pro Gly Gln
                85                  90                  95

Gln Gly Pro Gly Gln Gln Gly Pro Gly Ala Gly Ala Ala Ala Ala
            100                 105                 110

Gly Gln Phe Gly Ala Gly Pro Gly Gln Gln Gly Pro Phe Gly Gly Ala
        115                 120                 125

Ala Ala Ala Ala Gly Pro Gly Ala Gln Phe Gly Gln Gly Pro Phe
    130                 135                 140

Gly Pro Gly Ala Ala Gly Pro Gly Gln Phe Gly Pro Gly Gln Gln Gly
145                 150                 155                 160

Pro Ser Ala Gly Ala Ala Ala Ala Gly Ala Gly Gln Gln Gly Pro
                165                 170                 175

Gly Gln Phe Gly Pro Phe Ala Gly Ala Ala Ala Ala Gly Gln Phe
            180                 185                 190

Gly Ala Gly Pro Gly Gln Gln Gly Pro Phe Gly Pro Gly Gln Ala Gly
        195                 200                 205

Ala Gly Gln Gln Gly Pro Gly Gln Gln Gly Pro Phe Ala Gly Ala Ala
    210                 215                 220

Ala Ala Ala Gly Pro Gly Gln Gln Gly Pro Phe Gly Pro Gly Ala Gly
225                 230                 235                 240

Ala Ala Ala Ala Gly Gln Phe Gly Phe Gly Pro Gly Gln Gln Gly
                245                 250                 255

Pro Phe Gly Pro Gly Ala Ala Gly Gln Asn Gly Pro Gly Ala Gly Gln
            260                 265                 270

Phe Gly Pro Gly Gln Gly Pro Gly Gln Ala Ala Ala Ala
        275                 280                 285

Gly Pro Gly Gln Gln Gly Pro Phe Gly Pro Gly Ala Gly Ala Ala Ala
    290                 295                 300

Ala Ala Gly Gln Phe Gly Pro Gly Gln Gly Pro Gly Gln Phe Gly
305                 310                 315                 320

Pro Gly Ala Ala Gly Pro Gly Gln Gln Gly Pro Phe Gly Pro Gly Ala
                325                 330                 335

Gly Ala Ala Ala Ala Gly Gln Phe Gly Pro Gly Gln Gln Gly Pro
            340                 345                 350

```
Phe Gly Pro Gly Gln Gly Ala Ala Ala Ala Gly Gln Phe Gln Gln
            355                 360                 365

Gly Pro Gly Gln Gln Gly Pro Phe Gly Pro Gly Ala Ala Gly Pro Gly
        370                 375                 380

Gln Gln Gly Pro Phe Gly Pro Gly Ala Gly Ala Ala Ala Ala Gly
385                 390                 395                 400

Pro Gly Gln Phe Gly Pro Gly Gln Gln Gly Pro Ser Ala Gly Ala Ala
            405                 410                 415

Ala Ala Ala Gly Gln Phe Gly Ala Gly Pro Gly Gln Phe Gly Pro Phe
            420                 425                 430

Gly Pro Gly Gln Ala Gly Pro Gly Ala Gly Gln Gln Gly Gln Gly Pro
            435                 440                 445

Phe Gly Pro Gly Ala Gly Ala Ala Ala Ala Gly Gln Phe Gly Pro
            450                 455                 460

Gly Gln Gln Gly Pro Phe Gly Pro Gly Gln Gly Ala Ala Ala Ala
465                 470                 475                 480

Gly Pro Gly Ala Gly Gln Phe Gly Pro Gly Ala Ala Gly Gln Asn Gly
            485                 490                 495

Pro Gly Ala Gly Gln Phe Gly Pro Gly Gln Gln Gly Pro Gly Gln Gly
            500                 505                 510

Ala Ala Ala Ala Gly Gln Phe Gln Gln Pro Gly Gln Gln Gly
            515                 520                 525

Pro Phe Gly Pro Gly Ala Gly Ala Ala Ala Gly Gln Phe Gly
        530                 535                 540

Ala Gly Pro Gly Gln Gln Gly Pro Phe Gly Pro Gln Ala Gly Ala
545                 550                 555                 560

Gly Gln Gln Gly Pro Gly Gln Gly Pro Phe Ala Gly Ala Ala Ala
            565                 570                 575

Ala Ala Gly Pro Gly Ala Gly Gln Gln Gly Pro Gly Ala Ser
            580                 585                 590

<210> SEQ ID NO 5
<211> LENGTH: 590
<212> TYPE: PRT
<213> ORGANISM: Artificial Sequence
<220> FEATURE:
<223> OTHER INFORMATION: Met-PRT1107

<400> SEQUENCE: 5

Met Gly Pro Gly Val Phe Gly Pro Tyr Gly Pro Gly Ala Val Ala
1               5                   10                  15

Ala Ala Ala Gly Ile Asn Gly Pro Gly Ala Gly Val Phe Gly Pro Gly
            20                  25                  30

Ile Leu Gly Ile Tyr Gly Pro Gly Val Phe Gly Pro Val Phe Gly
            35                  40                  45

Pro Gly Ala Leu Ala Ala Ala Ala Gly Pro Gly Ile Tyr Gly Pro
            50                  55                  60

Gly Val Phe Gly Pro Ile Ala Val Ala Ala Ala Ala Gly Pro Gly
65                  70                  75                  80

Ala Gly Val Phe Gly Pro Gly Ala Leu Gly Ile Tyr Gly Pro Gly Val
            85                  90                  95

Phe Gly Pro Gly Val Phe Gly Pro Gly Ala Leu Ala Ala Ala Ala Ala
            100                 105                 110

Gly Ile Tyr Gly Ala Gly Pro Gly Val Phe Gly Pro Tyr Gly Leu Ala
            115                 120                 125
```

```
Ala Ala Ala Ala Gly Pro Gly Ala Gly Ile Tyr Gly Ile Gly Pro Tyr
            130                 135                 140

Gly Pro Gly Ala Leu Gly Pro Gly Ile Tyr Gly Pro Gly Val Phe Gly
145                 150                 155                 160

Pro Ile Ala Val Ala Ala Ala Ala Gly Ala Gly Val Phe Gly Pro
                165                 170                 175

Gly Ile Tyr Gly Pro Tyr Ala Val Ala Ala Ala Ala Gly Ile Tyr
            180                 185                 190

Gly Ala Gly Pro Gly Val Phe Gly Pro Tyr Gly Pro Gly Ile Leu Gly
        195                 200                 205

Ala Gly Val Phe Gly Pro Gly Val Phe Gly Pro Tyr Ala Val Ala Ala
210                 215                 220

Ala Ala Ala Gly Pro Gly Val Phe Gly Pro Tyr Gly Pro Gly Ala Leu
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Leu Gly Ile Asn Gly Pro Gly Ala Gly Ile
            260                 265                 270

Tyr Gly Pro Gly Val Phe Gly Pro Gly Ile Leu Ala Ala Ala Ala
            275                 280                 285

Gly Pro Gly Val Phe Gly Pro Tyr Gly Pro Gly Ala Val Ala Ala Ala
        290                 295                 300

Ala Ala Gly Ile Tyr Gly Pro Gly Val Phe Gly Pro Gly Ile Tyr Gly
305                 310                 315                 320

Pro Gly Ala Leu Gly Pro Gly Val Phe Gly Pro Tyr Gly Pro Gly Ala
            325                 330                 335

Leu Ala Ala Ala Ala Ala Gly Ile Tyr Gly Pro Gly Val Phe Gly Pro
        340                 345                 350

Tyr Gly Pro Gly Ile Leu Ala Ala Ala Ala Gly Ile Tyr Val Phe
            355                 360                 365

Gly Pro Gly Val Phe Gly Pro Tyr Gly Pro Gly Ala Leu Gly Pro Gly
        370                 375                 380

Val Phe Gly Pro Tyr Gly Pro Gly Ala Val Ala Ala Ala Ala Gly
385                 390                 395                 400

Pro Gly Ile Tyr Gly Pro Gly Val Phe Gly Pro Ile Ala Val Ala Ala
            405                 410                 415

Ala Ala Ala Gly Ile Tyr Gly Ala Gly Pro Gly Ile Tyr Gly Pro Tyr
            420                 425                 430

Gly Pro Gly Ile Leu Gly Pro Gly Ala Val Phe Gly Ile Gly Pro
        435                 440                 445

Tyr Gly Pro Gly Ala Val Ala Ala Ala Gly Ile Tyr Gly Pro
450                 455                 460

Gly Val Phe Gly Pro Tyr Gly Pro Gly Ile Leu Ala Ala Ala Ala
465                 470                 475                 480

Gly Pro Gly Ala Gly Ile Tyr Gly Pro Gly Ala Leu Gly Ile Asn Gly
                485                 490                 495

Pro Gly Ala Gly Ile Tyr Gly Pro Gly Val Phe Gly Pro Gly Ile Leu
            500                 505                 510

Ala Ala Ala Ala Ala Gly Ile Tyr Val Phe Gly Pro Gly Val Phe Gly
            515                 520                 525

Pro Tyr Gly Pro Gly Ala Val Ala Ala Ala Ala Gly Ile Tyr Gly
            530                 535                 540
```

-continued

Ala Gly Pro Gly Val Phe Gly Pro Tyr Gly Pro Gly Ile Leu Gly Ala
545                 550                 555                 560

Gly Val Phe Gly Pro Gly Val Phe Gly Pro Tyr Ala Val Ala Ala Ala
                565                 570                 575

Ala Ala Gly Pro Gly Ala Gly Val Phe Gly Pro Gly Ala Ile
            580                 585                 590

<210> SEQ ID NO 6
<211> LENGTH: 590
<212> TYPE: PRT
<213> ORGANISM: Artificial Sequence
<220> FEATURE:
<223> OTHER INFORMATION: Met-PRT1083

<400> SEQUENCE: 6

Met Gly Leu Gly Val Phe Gly Leu Tyr Gly Thr Gly Ala Ser Ala Ala
1               5                   10                  15

Ala Ala Ala Gly Ile Ala Gly Thr Gly Ser Gly Val Phe Gly Thr Gly
                20                  25                  30

Ile Ser Gly Ile Tyr Gly Leu Gly Val Phe Gly Leu Gly Val Phe Gly
            35                  40                  45

Thr Gly Ser Ser Ala Ala Ala Ala Gly Thr Gly Ile Tyr Gly Leu
50                  55                  60

Gly Val Phe Gly Leu Ser Ala Ser Ala Ala Ala Ala Gly Thr Gly
65                  70                  75                  80

Ser Gly Val Phe Gly Thr Gly Ala Ser Gly Ile Tyr Gly Leu Gly Val
                85                  90                  95

Phe Gly Leu Gly Val Phe Gly Thr Gly Ser Ser Ala Ala Ala Ala
                100                 105                 110

Gly Ile Tyr Gly Ser Gly Leu Gly Val Phe Gly Leu Tyr Gly Ser Ala
            115                 120                 125

Ala Ala Ala Gly Thr Gly Ser Gly Ile Tyr Gly Ile Gly Leu Tyr
130                 135                 140

Gly Thr Gly Ala Ser Gly Thr Gly Ile Tyr Gly Leu Gly Val Phe Gly
145                 150                 155                 160

Leu Ser Ala Ser Ala Ala Ala Ala Gly Ser Gly Val Phe Gly Thr
                165                 170                 175

Gly Ile Tyr Gly Leu Tyr Ala Ser Ala Ala Ala Ala Gly Ile Tyr
            180                 185                 190

Gly Ser Gly Leu Gly Val Phe Gly Leu Tyr Gly Thr Gly Ile Ser Gly
            195                 200                 205

Ser Gly Val Phe Gly Leu Gly Val Phe Gly Leu Tyr Ala Ser Ala Ala
                210                 215                 220

Ala Ala Ala Gly Leu Gly Val Phe Gly Leu Tyr Gly Thr Gly Ser Ser
225                 230                 235                 240

Ala Ala Ala Ala Ala Gly Ile Tyr Gly Tyr Gly Leu Gly Val Phe Gly
                245                 250                 255

Leu Tyr Gly Thr Gly Ala Ser Gly Ile Ala Gly Thr Gly Ser Gly Ile
            260                 265                 270

Tyr Gly Leu Gly Val Phe Gly Thr Gly Ile Ser Ala Ala Ala Ala
            275                 280                 285

Gly Leu Gly Val Phe Gly Leu Tyr Gly Thr Gly Ala Ser Ala Ala
        290                 295                 300

Ala Ala Gly Ile Tyr Gly Leu Gly Val Phe Gly Thr Gly Ile Tyr Gly
305                 310                 315                 320

```
Thr Gly Ser Ser Gly Leu Gly Val Phe Gly Leu Tyr Gly Thr Gly Ser
            325                 330                 335

Ser Ala Ala Ala Ala Gly Ile Tyr Gly Leu Gly Val Phe Gly Leu
        340                 345                 350

Tyr Gly Thr Gly Ile Ser Ala Ala Ala Ala Gly Ile Tyr Val Phe
        355                 360                 365

Gly Leu Gly Val Phe Gly Leu Tyr Gly Thr Gly Ala Ser Gly Leu Gly
            370                 375                 380

Val Phe Gly Leu Tyr Gly Thr Gly Ala Ser Ala Ala Ala Ala Gly
385                 390                 395                 400

Thr Gly Ile Tyr Gly Leu Gly Val Phe Gly Leu Ser Ala Ser Ala Ala
            405                 410                 415

Ala Ala Ala Gly Ile Tyr Gly Ser Gly Thr Gly Ile Tyr Gly Leu Tyr
            420                 425                 430

Gly Thr Gly Ile Ser Gly Thr Gly Ser Gly Val Phe Gly Ile Gly Leu
            435                 440                 445

Tyr Gly Thr Gly Ala Ser Ala Ala Ala Ala Gly Ile Tyr Gly Leu
        450                 455                 460

Gly Val Phe Gly Leu Tyr Gly Thr Gly Ile Ser Ala Ala Ala Ala
465                 470                 475                 480

Gly Thr Gly Ser Gly Ile Tyr Gly Thr Gly Ala Ser Gly Ile Ala Gly
            485                 490                 495

Thr Gly Ser Gly Ile Tyr Gly Leu Gly Val Phe Gly Thr Gly Ile Ser
            500                 505                 510

Ala Ala Ala Ala Ala Gly Ile Tyr Val Phe Gly Leu Gly Val Phe Gly
            515                 520                 525

Leu Tyr Gly Thr Gly Ala Ser Ala Ala Ala Ala Gly Ile Tyr Gly
        530                 535                 540

Ser Gly Leu Gly Val Phe Gly Leu Tyr Gly Thr Gly Ile Ser Gly Ser
545                 550                 555                 560

Gly Val Phe Gly Leu Gly Val Phe Gly Leu Tyr Ala Ser Ala Ala Ala
            565                 570                 575

Ala Ala Gly Thr Gly Ser Gly Val Phe Gly Thr Gly Ala Ser
        580                 585                 590

<210> SEQ ID NO 7
<211> LENGTH: 590
<212> TYPE: PRT
<213> ORGANISM: Artificial Sequence
<220> FEATURE:
<223> OTHER INFORMATION: Met-PRT826

<400> SEQUENCE: 7

Met Gly Pro Gly Gln Gln Gly Pro Tyr Gly Pro Gly Ala Thr Ala Ala
1               5                   10                  15

Ala Ala Ala Gly Gln Asn Gly Pro Gly Thr Gly Gln Gln Gly Pro Gly
            20                  25                  30

Gln Thr Gly Gln Tyr Gly Pro Gly Gln Gln Gly Pro Gly Gln Gln Gly
            35                  40                  45

Pro Gly Thr Thr Ala Ala Ala Ala Gly Pro Gly Gln Tyr Gly Pro
        50                  55                  60

Gly Gln Gln Gly Pro Thr Ala Thr Ala Ala Ala Ala Gly Pro Gly
65                  70                  75                  80

Thr Gly Gln Gln Gly Pro Gly Ala Thr Gly Gln Tyr Gly Pro Gly Gln
            85                  90                  95
```

```
Gln Gly Pro Gly Gln Gly Pro Thr Ala Ala Ala Ala
            100             105             110
Gly Gln Tyr Gly Thr Gly Pro Gly Gln Gly Pro Tyr Gly Thr Ala
        115             120             125
Ala Ala Ala Ala Gly Pro Gly Thr Gly Gln Tyr Gly Gln Gly Pro Tyr
130             135             140
Gly Pro Gly Ala Thr Gly Pro Gly Gln Tyr Gly Pro Gly Gln Gln Gly
145             150             155             160
Pro Thr Ala Thr Ala Ala Ala Ala Gly Thr Gly Gln Gln Gly Pro
            165             170             175
Gly Gln Tyr Gly Pro Tyr Ala Thr Ala Ala Ala Ala Gly Gln Tyr
        180             185             190
Gly Thr Gly Pro Gly Gln Gln Gly Pro Tyr Gly Pro Gly Gln Thr Gly
        195             200             205
Thr Gly Gln Gln Gly Pro Gly Gln Gln Gly Pro Tyr Ala Thr Ala Ala
    210             215             220
Ala Ala Ala Gly Pro Gly Gln Gln Gly Pro Tyr Gly Pro Gly Thr Thr
225             230             235             240
Ala Ala Ala Ala Ala Gly Gln Tyr Gly Tyr Gly Pro Gly Gln Gln Gly
                245             250             255
Pro Tyr Gly Pro Gly Ala Thr Gly Gln Asn Gly Pro Gly Thr Gly Gln
            260             265             270
Tyr Gly Pro Gly Gln Gln Gly Pro Gly Gln Thr Ala Ala Ala Ala Ala
            275             280             285
Gly Pro Gly Gln Gln Gly Pro Tyr Gly Pro Gly Ala Thr Ala Ala Ala
        290             295             300
Ala Ala Gly Gln Tyr Gly Pro Gly Gln Gln Gly Pro Gly Gln Tyr Gly
305             310             315             320
Pro Gly Thr Thr Gly Pro Gly Gln Gln Gly Pro Tyr Gly Pro Gly Thr
            325             330             335
Thr Ala Ala Ala Ala Ala Gly Gln Tyr Gly Pro Gly Gln Gln Gly Pro
        340             345             350
Tyr Gly Pro Gly Gln Thr Ala Ala Ala Ala Gly Gln Tyr Gln Gln
        355             360             365
Gly Pro Gly Gln Gln Gly Pro Tyr Gly Pro Gly Ala Thr Gly Pro Gly
        370             375             380
Gln Gln Gly Pro Tyr Gly Pro Gly Ala Thr Ala Ala Ala Ala Gly
385             390             395             400
Pro Gly Gln Tyr Gly Pro Gly Gln Gln Gly Pro Thr Ala Thr Ala Ala
            405             410             415
Ala Ala Ala Gly Gln Tyr Gly Thr Gly Pro Gly Gln Tyr Gly Pro Tyr
        420             425             430
Gly Pro Gly Gln Thr Gly Pro Gly Thr Gly Gln Gln Gly Gln Gly Pro
        435             440             445
Tyr Gly Pro Gly Ala Thr Ala Ala Ala Ala Gly Gln Tyr Gly Pro
        450             455             460
Gly Gln Gln Gly Pro Tyr Gly Pro Gly Gln Thr Ala Ala Ala Ala Ala
465             470             475             480
Gly Pro Gly Thr Gly Gln Tyr Gly Pro Gly Ala Thr Gly Gln Asn Gly
            485             490             495
Pro Gly Thr Gly Gln Tyr Gly Pro Gly Gln Gln Gly Pro Gly Gln Thr
            500             505             510
```

```
Ala Ala Ala Ala Ala Gly Gln Tyr Gln Gln Gly Pro Gly Gln Gln Gly
            515                 520                 525

Pro Tyr Gly Pro Gly Ala Thr Ala Ala Ala Ala Gly Gln Tyr Gly
        530                 535                 540

Thr Gly Pro Gly Gln Gln Gly Pro Tyr Gly Pro Gly Gln Thr Gly Thr
545                 550                 555                 560

Gly Gln Gln Gly Pro Gln Gln Gly Pro Tyr Ala Thr Ala Ala Ala
                565                 570                 575

Ala Ala Gly Pro Gly Thr Gly Gln Gln Gly Pro Gly Ala Thr
            580                 585                 590

<210> SEQ ID NO 8
<211> LENGTH: 590
<212> TYPE: PRT
<213> ORGANISM: Artificial Sequence
<220> FEATURE:
<223> OTHER INFORMATION: Met-PRT1127

<400> SEQUENCE: 8

Met Gly Pro Gly Val Phe Gly Pro Tyr Gly Pro Gly Ala Thr Ala Ala
1               5                   10                  15

Ala Ala Ala Gly Ile Asn Gly Pro Gly Thr Gly Val Phe Gly Pro Gly
            20                  25                  30

Ile Thr Gly Ile Tyr Gly Pro Gly Val Phe Gly Pro Gly Val Phe Gly
            35                  40                  45

Pro Gly Thr Thr Ala Ala Ala Ala Gly Pro Gly Ile Tyr Gly Pro
        50                  55                  60

Gly Val Phe Gly Pro Thr Ala Thr Ala Ala Ala Ala Gly Pro Gly
65                  70                  75                  80

Thr Gly Val Phe Gly Pro Gly Ala Thr Gly Ile Tyr Gly Pro Gly Val
                85                  90                  95

Phe Gly Pro Gly Val Phe Gly Pro Gly Thr Thr Ala Ala Ala Ala
            100                 105                 110

Gly Ile Tyr Gly Thr Gly Pro Gly Val Phe Gly Pro Tyr Gly Thr Ala
            115                 120                 125

Ala Ala Ala Ala Gly Pro Gly Thr Gly Ile Tyr Gly Ile Gly Pro Tyr
        130                 135                 140

Gly Pro Gly Ala Thr Gly Pro Gly Ile Tyr Gly Pro Gly Val Phe Gly
145                 150                 155                 160

Pro Thr Ala Thr Ala Ala Ala Ala Gly Thr Gly Val Phe Gly Pro
            165                 170                 175

Gly Ile Tyr Gly Pro Tyr Ala Thr Ala Ala Ala Ala Gly Ile Tyr
            180                 185                 190

Gly Thr Gly Pro Gly Val Phe Gly Pro Tyr Gly Pro Gly Ile Thr Gly
            195                 200                 205

Thr Gly Val Phe Gly Pro Gly Val Phe Gly Pro Tyr Ala Thr Ala Ala
            210                 215                 220

Ala Ala Ala Gly Pro Gly Val Phe Gly Pro Tyr Gly Pro Gly Thr Thr
225                 230                 235                 240

Ala Ala Ala Ala Ala Gly Ile Tyr Gly Tyr Gly Pro Gly Val Phe Gly
            245                 250                 255

Pro Tyr Gly Pro Gly Ala Thr Gly Ile Asn Gly Pro Gly Thr Gly Ile
            260                 265                 270

Tyr Gly Pro Gly Val Phe Gly Pro Gly Ile Thr Ala Ala Ala Ala Ala
            275                 280                 285
```

-continued

```
Gly Pro Gly Val Phe Gly Pro Tyr Gly Pro Gly Ala Thr Ala Ala
        290                 295                 300
Ala Ala Gly Ile Tyr Gly Pro Gly Val Phe Gly Pro Gly Ile Tyr Gly
305                 310                 315                 320
Pro Gly Thr Thr Gly Pro Gly Val Phe Gly Pro Tyr Gly Pro Gly Thr
                325                 330                 335
Thr Ala Ala Ala Ala Ala Gly Ile Tyr Gly Pro Gly Val Phe Gly Pro
        340                 345                 350
Tyr Gly Pro Gly Ile Thr Ala Ala Ala Ala Gly Ile Tyr Val Phe
        355                 360                 365
Gly Pro Gly Val Phe Gly Pro Tyr Gly Pro Gly Ala Thr Gly Pro Gly
        370                 375                 380
Val Phe Gly Pro Tyr Gly Pro Gly Ala Thr Ala Ala Ala Ala Gly
385                 390                 395                 400
Pro Gly Ile Tyr Gly Pro Gly Val Phe Gly Pro Thr Ala Thr Ala Ala
                405                 410                 415
Ala Ala Ala Gly Ile Tyr Gly Thr Gly Pro Gly Ile Tyr Gly Pro Tyr
        420                 425                 430
Gly Pro Gly Ile Thr Gly Pro Gly Thr Gly Val Phe Gly Ile Gly Pro
        435                 440                 445
Tyr Gly Pro Gly Ala Thr Ala Ala Ala Ala Gly Ile Tyr Gly Pro
        450                 455                 460
Gly Val Phe Gly Pro Tyr Gly Pro Gly Ile Thr Ala Ala Ala Ala
465                 470                 475                 480
Gly Pro Gly Thr Gly Ile Tyr Gly Pro Gly Ala Thr Gly Ile Asn Gly
                485                 490                 495
Pro Gly Thr Gly Ile Tyr Gly Pro Gly Val Phe Gly Pro Gly Ile Thr
                500                 505                 510
Ala Ala Ala Ala Ala Gly Ile Tyr Val Phe Gly Pro Gly Val Phe Gly
        515                 520                 525
Pro Tyr Gly Pro Gly Ala Thr Ala Ala Ala Ala Gly Ile Tyr Gly
        530                 535                 540
Thr Gly Pro Gly Val Phe Gly Pro Tyr Gly Pro Gly Ile Thr Gly Thr
545                 550                 555                 560
Gly Val Phe Gly Pro Gly Val Phe Gly Pro Tyr Ala Thr Ala Ala Ala
                565                 570                 575
Ala Ala Gly Pro Gly Thr Gly Val Phe Gly Pro Gly Ala Thr
        580                 585                 590

<210> SEQ ID NO 9
<211> LENGTH: 601
<212> TYPE: PRT
<213> ORGANISM: Artificial Sequence
<220> FEATURE:
<223> OTHER INFORMATION: PRT918

<400> SEQUENCE: 9

Met His His His His His Ser Ser Gly Ser Ser Gly Pro Gly Val
1               5                   10                  15
Phe Gly Pro Tyr Gly Pro Gly Ala Ser Ala Ala Ala Ala Gly Ile
            20                  25                  30
Asn Gly Pro Gly Ser Gly Val Phe Gly Pro Gly Ile Ser Gly Ile Tyr
        35                  40                  45
Gly Pro Gly Val Phe Gly Pro Gly Val Phe Gly Pro Gly Ser Ser Ala
    50                  55                  60
```

```
Ala Ala Ala Ala Gly Pro Gly Ile Tyr Gly Pro Val Phe Gly Pro
 65                  70                  75                  80

Ser Ala Ser Ala Ala Ala Ala Gly Pro Gly Ser Gly Val Phe Gly
                     85                  90                  95

Pro Gly Ala Ser Gly Ile Tyr Gly Pro Gly Val Phe Gly Pro Gly Val
            100                 105                 110

Phe Gly Pro Gly Ser Ser Ala Ala Ala Ala Gly Ile Tyr Gly Ser
            115                 120                 125

Gly Pro Gly Val Phe Gly Pro Tyr Gly Ser Ala Ala Ala Ala Gly
        130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
                165                 170                 175

Ala Ala Ala Ala Gly Ser Gly Val Phe Gly Pro Gly Ile Tyr Gly Pro
                180                 185                 190

Tyr Ala Ser Ala Ala Ala Ala Gly Ile Tyr Gly Ser Gly Pro Gly
        195                 200                 205

Val Phe Gly Pro Tyr Gly Pro Gly Ile Ser Gly Ser Gly Val Phe Gly
210                 215                 220

Pro Gly Val Phe Gly Pro Tyr Ala Ser Ala Ala Ala Ala Gly Pro
225                 230                 235                 240

Gly Val Phe Gly Pro Tyr Gly Pro Gly Ser Ser Ala Ala Ala Ala
                245                 250                 255

Gly Ile Tyr Gly Tyr Gly Pro Gly Val Phe Gly Pro Tyr Gly Pro Gly
            260                 265                 270

Ala Ser Gly Ile Asn Gly Pro Gly Ser Gly Ile Tyr Gly Pro Gly Val
        275                 280                 285

Phe Gly Pro Gly Ile Ser Ala Ala Ala Ala Gly Pro Gly Val Phe
        290                 295                 300

Gly Pro Tyr Gly Pro Gly Ala Ser Ala Ala Ala Ala Gly Ile Tyr
305                 310                 315                 320

Gly Pro Gly Val Phe Gly Pro Gly Ile Tyr Gly Pro Gly Ser Ser Gly
                325                 330                 335

Pro Gly Val Phe Gly Pro Tyr Gly Pro Gly Ser Ser Ala Ala Ala Ala
            340                 345                 350

Ala Gly Ile Tyr Gly Pro Gly Val Phe Gly Pro Tyr Gly Pro Gly Ile
        355                 360                 365

Ser Ala Ala Ala Ala Gly Ile Tyr Val Phe Gly Pro Gly Val Phe
    370                 375                 380

Gly Pro Tyr Gly Pro Gly Ala Ser Gly Pro Gly Val Phe Gly Pro Tyr
385                 390                 395                 400

Gly Pro Gly Ala Ser Ala Ala Ala Ala Gly Pro Gly Ile Tyr Gly
            405                 410                 415

Pro Gly Val Phe Gly Pro Ser Ala Ser Ala Ala Ala Ala Gly Ile
                420                 425                 430

Tyr Gly Ser Gly Pro Gly Ile Tyr Gly Pro Tyr Gly Pro Gly Ile Ser
        435                 440                 445

Gly Pro Gly Ser Gly Val Phe Gly Ile Gly Pro Tyr Gly Pro Gly Ala
    450                 455                 460

Ser Ala Ala Ala Ala Gly Ile Tyr Gly Pro Gly Val Phe Gly Pro
465                 470                 475                 480
```

```
Tyr Gly Pro Gly Ile Ser Ala Ala Ala Ala Gly Pro Gly Ser Gly
                485                 490                 495

Ile Tyr Gly Pro Gly Ala Ser Gly Ile Asn Gly Pro Gly Ser Gly Ile
        500                 505                 510

Tyr Gly Pro Gly Val Phe Gly Pro Gly Ile Ser Ala Ala Ala Ala
        515                 520                 525

Gly Ile Tyr Val Phe Gly Pro Gly Val Phe Gly Pro Tyr Gly Pro Gly
        530                 535                 540

Ala Ser Ala Ala Ala Ala Gly Ile Tyr Gly Ser Gly Pro Gly Val
545                 550                 555                 560

Phe Gly Pro Tyr Gly Pro Gly Ile Ser Gly Ser Gly Val Phe Gly Pro
                565                 570                 575

Gly Val Phe Gly Pro Tyr Ala Ser Ala Ala Ala Ala Gly Pro Gly
                580                 585                 590

Ser Gly Val Phe Gly Pro Gly Ala Ser
                595                 600
```

<210> SEQ ID NO 10
<211> LENGTH: 601
<212> TYPE: PRT
<213> ORGANISM: Artificial Sequence
<220> FEATURE:
<223> OTHER INFORMATION: PRT1104

<400> SEQUENCE: 10

```
Met His His His His His Ala Ala Gly Ala Ala Gly Pro Gly Gln
1               5                   10                  15

Gln Gly Pro Tyr Gly Pro Gly Ala Gly Ala Ala Ala Ala Gly Gln
                20                  25                  30

Asn Gly Pro Gly Ala Gly Gln Gln Gly Pro Gly Gln Ala Gly Gln Tyr
        35                  40                  45

Gly Pro Gly Gln Gln Gly Pro Gly Gln Gln Gly Pro Gly Ala Gly Ala
        50                  55                  60

Ala Ala Ala Ala Gly Pro Gly Gln Tyr Gly Pro Gly Gln Gln Gly Pro
65                  70                  75                  80

Ser Ala Gly Ala Ala Ala Ala Gly Pro Gly Ala Gly Gln Gln Gly
                85                  90                  95

Pro Gly Ala Ala Gly Gln Tyr Gly Pro Gly Gln Gln Gly Pro Gly Gln
                100                 105                 110

Gln Gly Pro Gly Ala Gly Ala Ala Ala Ala Gly Gln Tyr Gly Ala
        115                 120                 125

Gly Pro Gly Gln Gln Gly Pro Tyr Gly Gly Ala Ala Ala Ala Gly
        130                 135                 140

Pro Gly Ala Gly Gln Tyr Gly Gln Gly Pro Tyr Gly Pro Gly Ala Ala
145                 150                 155                 160

Gly Pro Gly Gln Tyr Gly Pro Gly Gln Gln Gly Pro Ser Ala Gly Ala
                165                 170                 175

Ala Ala Ala Ala Gly Ala Gly Gln Gln Gly Pro Gly Gln Tyr Gly Pro
                180                 185                 190

Tyr Ala Gly Ala Ala Ala Ala Gly Gln Tyr Gly Ala Gly Pro Gly
        195                 200                 205

Gln Gln Gly Pro Tyr Gly Pro Gly Ala Gly Ala Gly Gln Gln Gly
        210                 215                 220

Pro Gly Gln Gln Gly Pro Tyr Ala Gly Ala Ala Ala Ala Gly Pro
225                 230                 235                 240
```

Gly Gln Gln Gly Pro Tyr Gly Pro Gly Ala Gly Ala Ala Ala
                245                 250                 255

Gly Gln Tyr Gly Tyr Gly Pro Gly Gln Gln Gly Pro Tyr Gly Pro Gly
            260                 265                 270

Ala Ala Gly Gln Asn Gly Pro Gly Ala Gly Gln Tyr Gly Pro Gly Gln
            275                 280                 285

Gln Gly Pro Gly Gln Gly Ala Ala Ala Gly Pro Gly Gln Gln
    290                 295                 300

Gly Pro Tyr Gly Pro Gly Ala Ala Ala Ala Gly Gln Tyr
305                 310                 315                 320

Gly Pro Gly Gln Gln Gly Pro Gly Gln Tyr Gly Pro Gly Ala Ala Gly
                325                 330                 335

Pro Gly Gln Gln Gly Pro Tyr Gly Pro Gly Ala Gly Ala Ala Ala
            340                 345                 350

Ala Gly Gln Tyr Gly Pro Gly Gln Gln Gly Pro Tyr Gly Pro Gly Gln
            355                 360                 365

Gly Ala Ala Ala Ala Gly Gln Tyr Gln Gln Gly Pro Gly Gln Gln
370                 375                 380

Gly Pro Tyr Gly Pro Gly Ala Ala Gly Pro Gly Gln Gln Gly Pro Tyr
385                 390                 395                 400

Gly Pro Gly Ala Gly Ala Ala Ala Ala Gly Pro Gly Gln Tyr Gly
                405                 410                 415

Pro Gly Gln Gln Gly Pro Ser Ala Gly Ala Ala Ala Ala Gly Gln
            420                 425                 430

Tyr Gly Ala Gly Pro Gly Gln Tyr Gly Pro Tyr Gly Pro Gly Gln Ala
            435                 440                 445

Gly Pro Gly Ala Gly Gln Gln Gly Gln Gly Pro Tyr Gly Pro Gly Ala
    450                 455                 460

Gly Ala Ala Ala Ala Gly Gln Tyr Gly Pro Gly Gln Gly Pro
465                 470                 475                 480

Tyr Gly Pro Gly Gln Gly Ala Ala Ala Gly Pro Gly Ala Gly
                485                 490                 495

Gln Tyr Gly Pro Gly Ala Ala Gly Gln Asn Gly Pro Gly Ala Gly Gln
            500                 505                 510

Tyr Gly Pro Gly Gln Gln Gly Pro Gly Gln Gly Ala Ala Ala Ala
            515                 520                 525

Gly Gln Tyr Gln Gln Gly Pro Gly Gln Gln Gly Pro Tyr Gly Pro Gly
    530                 535                 540

Ala Gly Ala Ala Ala Ala Gly Gln Tyr Gly Ala Gly Pro Gly Gln
545                 550                 555                 560

Gln Gly Pro Tyr Gly Pro Gly Gln Ala Gly Ala Gly Gln Gln Gly Pro
            565                 570                 575

Gly Gln Gln Gly Pro Tyr Ala Gly Ala Ala Ala Ala Gly Pro Gly
            580                 585                 590

Ala Gly Gln Gln Gly Pro Gly Ala Ser
    595                 600

<210> SEQ ID NO 11
<211> LENGTH: 601
<212> TYPE: PRT
<213> ORGANISM: Artificial Sequence
<220> FEATURE:
<223> OTHER INFORMATION: PRT1105

-continued

<400> SEQUENCE: 11

Met His His His His His Ala Ala Gly Ala Ala Gly Pro Gly Val
1               5                   10                  15

Phe Gly Pro Tyr Gly Pro Gly Ala Gly Ala Ala Ala Ala Gly Ile
                20                  25                  30

Asn Gly Pro Gly Ala Gly Val Phe Gly Pro Gly Ile Ala Gly Ile Tyr
                35                  40                  45

Gly Pro Gly Val Phe Gly Pro Gly Val Phe Gly Pro Gly Ala Gly Ala
            50                  55                  60

Ala Ala Ala Ala Gly Pro Gly Ile Tyr Gly Pro Gly Val Phe Gly Pro
65                  70                  75                  80

Gly Ala Gly Ala Ala Ala Ala Gly Pro Gly Ala Gly Val Phe Gly
                85                  90                  95

Pro Gly Ala Ala Gly Ile Tyr Gly Pro Gly Val Phe Gly Pro Gly Val
                100                 105                 110

Phe Gly Pro Gly Ala Gly Ala Ala Ala Ala Gly Ile Tyr Gly Ala
                115                 120                 125

Gly Pro Gly Val Phe Gly Pro Tyr Gly Gly Ala Ala Ala Ala Gly
            130                 135                 140

Pro Gly Ala Gly Ile Tyr Gly Ile Gly Pro Tyr Gly Pro Gly Ala Ala
145                 150                 155                 160

Gly Pro Gly Ile Tyr Gly Pro Gly Val Phe Gly Pro Gly Ala Gly Ala
                165                 170                 175

Ala Ala Ala Gly Ala Gly Val Phe Gly Pro Gly Ile Tyr Gly Pro
                180                 185                 190

Tyr Ala Gly Ala Ala Ala Ala Gly Ile Tyr Gly Ala Gly Pro Gly
                195                 200                 205

Val Phe Gly Pro Tyr Gly Pro Gly Ile Ala Gly Ala Gly Val Phe Gly
                210                 215                 220

Pro Gly Val Phe Gly Pro Tyr Ala Gly Ala Ala Ala Ala Gly Pro
225                 230                 235                 240

Gly Val Phe Gly Pro Tyr Gly Pro Gly Ala Gly Ala Ala Ala Ala
                245                 250                 255

Gly Ile Tyr Gly Tyr Gly Pro Gly Val Phe Gly Pro Tyr Gly Pro Gly
                260                 265                 270

Ala Ala Gly Ile Asn Gly Pro Gly Ala Gly Ile Tyr Gly Pro Gly Val
                275                 280                 285

Phe Gly Pro Gly Ile Gly Ala Ala Ala Ala Gly Pro Gly Val Phe
                290                 295                 300

Gly Pro Tyr Gly Pro Gly Ala Gly Ala Ala Ala Ala Gly Ile Tyr
305                 310                 315                 320

Gly Pro Gly Val Phe Gly Pro Gly Ile Tyr Gly Pro Gly Ala Ala Gly
                325                 330                 335

Pro Gly Val Phe Gly Pro Tyr Gly Pro Gly Ala Gly Ala Ala Ala
                340                 345                 350

Ala Gly Ile Tyr Gly Pro Gly Val Phe Gly Pro Tyr Gly Pro Gly Ile
                355                 360                 365

Gly Ala Ala Ala Ala Gly Ile Tyr Val Phe Gly Pro Gly Val Phe
                370                 375                 380

Gly Pro Tyr Gly Pro Gly Ala Ala Gly Pro Gly Val Phe Gly Pro Tyr
385                 390                 395                 400

```
Gly Pro Gly Ala Gly Ala Ala Ala Ala Gly Pro Gly Ile Tyr Gly
                405                 410                 415

Pro Gly Val Phe Gly Pro Gly Ala Gly Ala Ala Ala Ala Gly Ile
            420                 425                 430

Tyr Gly Ala Gly Pro Gly Ile Tyr Gly Pro Tyr Gly Pro Gly Ile Ala
            435                 440                 445

Gly Pro Gly Ala Gly Val Phe Gly Ile Gly Pro Tyr Gly Pro Gly Ala
450                 455                 460

Gly Ala Ala Ala Ala Gly Ile Tyr Gly Pro Gly Val Phe Gly Pro
465                 470                 475                 480

Tyr Gly Pro Gly Ile Gly Ala Ala Ala Ala Gly Pro Gly Ala Gly
                485                 490                 495

Ile Tyr Gly Pro Gly Ala Ala Gly Ile Asn Gly Pro Gly Ala Gly Ile
            500                 505                 510

Tyr Gly Pro Gly Val Phe Gly Pro Gly Ile Gly Ala Ala Ala Ala
            515                 520                 525

Gly Ile Tyr Val Phe Gly Pro Gly Val Phe Gly Pro Tyr Gly Pro Gly
            530                 535                 540

Ala Gly Ala Ala Ala Ala Gly Ile Tyr Gly Ala Gly Pro Gly Val
545                 550                 555                 560

Phe Gly Pro Tyr Gly Pro Gly Ile Ala Gly Ala Gly Val Phe Gly Pro
                565                 570                 575

Gly Val Phe Gly Pro Tyr Ala Gly Ala Ala Ala Ala Gly Pro Gly
            580                 585                 590

Ala Gly Val Phe Gly Pro Gly Ala Gly
            595                 600

<210> SEQ ID NO 12
<211> LENGTH: 601
<212> TYPE: PRT
<213> ORGANISM: Artificial Sequence
<220> FEATURE:
<223> OTHER INFORMATION: PRT1103

<400> SEQUENCE: 12

Met His His His His His Ala Ala Gly Ala Ala Gly Pro Gly Gln
1               5                   10                  15

Gln Gly Pro Phe Gly Pro Gly Ala Gly Ala Ala Ala Ala Gly Gln
            20                  25                  30

Asn Gly Pro Gly Ala Gly Gln Gln Gly Pro Gly Gln Ala Gly Gln Phe
            35                  40                  45

Gly Pro Gly Gln Gln Gly Pro Gly Gln Gln Gly Pro Gly Ala Gly Ala
50                  55                  60

Ala Ala Ala Gly Pro Gly Gln Phe Gly Pro Gly Gln Gln Gly Pro
65                  70                  75                  80

Ser Ala Gly Ala Ala Ala Ala Gly Pro Gly Ala Gly Gln Gln Gly
                85                  90                  95

Pro Gly Ala Ala Gly Gln Phe Gly Pro Gly Gln Gln Gly Pro Gly Gln
            100                 105                 110

Gln Gly Pro Gly Ala Gly Ala Ala Ala Ala Gly Gln Phe Gly Ala
            115                 120                 125

Gly Pro Gly Gln Gln Gly Pro Phe Gly Gly Ala Ala Ala Ala Gly
            130                 135                 140

Pro Gly Ala Gly Gln Phe Gly Gln Gly Pro Phe Gly Pro Gly Ala Ala
145                 150                 155                 160
```

```
Gly Pro Gly Gln Phe Gly Pro Gly Gln Gln Gly Pro Ser Ala Gly Ala
            165                 170                 175

Ala Ala Ala Ala Gly Ala Gly Gln Gln Gly Pro Gln Phe Gly Pro
        180                 185                 190

Phe Ala Gly Ala Ala Ala Ala Gly Gln Phe Gly Ala Gly Pro Gly
        195                 200                 205

Gln Gln Gly Pro Phe Gly Pro Gly Gln Ala Gly Ala Gly Gln Gln Gly
    210                 215                 220

Pro Gly Gln Gln Gly Pro Phe Ala Gly Ala Ala Ala Ala Gly Pro
225                 230                 235                 240

Gly Gln Gln Gly Pro Phe Gly Pro Gly Ala Gly Ala Ala Ala Ala
            245                 250                 255

Gly Gln Phe Gly Phe Gly Pro Gly Gln Gln Gly Pro Phe Gly Pro Gly
            260                 265                 270

Ala Ala Gly Gln Asn Gly Pro Gly Ala Gly Gln Phe Gly Pro Gly Gln
        275                 280                 285

Gln Gly Pro Gly Gln Gly Ala Ala Ala Ala Gly Pro Gly Gln Gln
        290                 295                 300

Gly Pro Phe Gly Pro Gly Ala Gly Ala Ala Ala Ala Gly Gln Phe
305                 310                 315                 320

Gly Pro Gly Gln Gln Gly Pro Gly Gln Phe Gly Pro Gly Ala Ala Gly
            325                 330                 335

Pro Gly Gln Gln Gly Pro Phe Gly Pro Gly Ala Gly Ala Ala Ala
        340                 345                 350

Ala Gly Gln Phe Gly Pro Gly Gln Gln Gly Pro Phe Gly Pro Gly Gln
        355                 360                 365

Gly Ala Ala Ala Ala Gly Gln Phe Gln Gln Gly Pro Gly Gln Gln
        370                 375                 380

Gly Pro Phe Gly Pro Gly Ala Ala Gly Pro Gly Gln Gln Gly Pro Phe
385                 390                 395                 400

Gly Pro Gly Ala Gly Ala Ala Ala Ala Gly Pro Gly Gln Phe Gly
            405                 410                 415

Pro Gly Gln Gln Gly Pro Ser Ala Gly Ala Ala Ala Ala Gly Gln
        420                 425                 430

Phe Gly Ala Gly Pro Gly Gln Phe Gly Pro Phe Gly Pro Gly Gln Ala
435                 440                 445

Gly Pro Gly Ala Gly Gln Gln Gly Gly Pro Phe Gly Pro Gly Ala
        450                 455                 460

Gly Ala Ala Ala Ala Gly Gln Phe Gly Pro Gly Gln Gln Gly Pro
465                 470                 475                 480

Phe Gly Pro Gly Gln Gly Ala Ala Ala Ala Gly Pro Gly Ala Gly
        485                 490                 495

Gln Phe Gly Pro Gly Ala Ala Gly Gln Asn Gly Pro Gly Ala Gly Gln
        500                 505                 510

Phe Gly Pro Gly Gln Gln Gly Pro Gly Gln Gly Ala Ala Ala Ala
        515                 520                 525

Gly Gln Phe Gln Gln Gly Pro Gly Gln Gln Gly Pro Phe Gly Pro Gly
        530                 535                 540

Ala Gly Ala Ala Ala Ala Gly Gln Phe Gly Ala Gly Pro Gly Gln
545                 550                 555                 560

Gln Gly Pro Phe Gly Pro Gly Gln Ala Gly Ala Gly Gln Gln Gly Pro
            565                 570                 575
```

Gly Gln Gln Gly Pro Phe Ala Gly Ala Ala Ala Gly Pro Gly
            580                 585                 590

Ala Gly Gln Gln Gly Pro Gly Ala Ser
        595                 600

<210> SEQ ID NO 13
<211> LENGTH: 601
<212> TYPE: PRT
<213> ORGANISM: Artificial Sequence
<220> FEATURE:
<223> OTHER INFORMATION: PRT1107

<400> SEQUENCE: 13

Met His His His His His Ala Ala Gly Ala Ala Gly Pro Gly Val
1               5                   10                  15

Phe Gly Pro Tyr Gly Pro Gly Ala Val Ala Ala Ala Ala Gly Ile
                20                  25                  30

Asn Gly Pro Gly Ala Gly Val Phe Gly Pro Gly Ile Leu Gly Ile Tyr
                35                  40                  45

Gly Pro Gly Val Phe Gly Pro Gly Val Phe Gly Pro Gly Ala Leu Ala
        50                  55                  60

Ala Ala Ala Gly Pro Gly Ile Tyr Gly Pro Gly Val Phe Gly Pro
65                  70                  75                  80

Ile Ala Val Ala Ala Ala Ala Gly Pro Gly Ala Gly Val Phe Gly
                85                  90                  95

Pro Gly Ala Leu Gly Ile Tyr Gly Pro Gly Val Phe Gly Pro Gly Val
                100                 105                 110

Phe Gly Pro Gly Ala Leu Ala Ala Ala Ala Gly Ile Tyr Gly Ala
                115                 120                 125

Gly Pro Gly Val Phe Gly Pro Tyr Gly Leu Ala Ala Ala Ala Gly
        130                 135                 140

Pro Gly Ala Gly Ile Tyr Gly Ile Gly Pro Tyr Gly Pro Gly Ala Leu
145                 150                 155                 160

Gly Pro Gly Ile Tyr Gly Pro Gly Val Phe Gly Pro Ile Ala Val Ala
                165                 170                 175

Ala Ala Ala Gly Ala Gly Val Phe Gly Pro Gly Ile Tyr Gly Pro
                180                 185                 190

Tyr Ala Val Ala Ala Ala Ala Gly Ile Tyr Gly Ala Gly Pro Gly
        195                 200                 205

Val Phe Gly Pro Tyr Gly Pro Gly Ile Leu Gly Ala Gly Val Phe Gly
210                 215                 220

Pro Gly Val Phe Gly Pro Tyr Ala Val Ala Ala Ala Ala Gly Pro
225                 230                 235                 240

Gly Val Phe Gly Pro Tyr Gly Pro Gly Ala Leu Ala Ala Ala Ala
                245                 250                 255

Gly Ile Tyr Gly Tyr Gly Pro Gly Val Phe Gly Pro Tyr Gly Pro Gly
                260                 265                 270

Ala Leu Gly Ile Asn Gly Pro Gly Ala Gly Ile Tyr Gly Pro Gly Val
                275                 280                 285

Phe Gly Pro Gly Ile Leu Ala Ala Ala Ala Gly Pro Gly Val Phe
                290                 295                 300

Gly Pro Tyr Gly Pro Gly Ala Val Ala Ala Ala Ala Gly Ile Tyr
305                 310                 315                 320

Gly Pro Gly Val Phe Gly Pro Gly Ile Tyr Gly Pro Gly Ala Leu Gly
                325                 330                 335

```
Pro Gly Val Phe Gly Pro Tyr Gly Pro Gly Ala Leu Ala Ala Ala Ala
                340                 345                 350

Ala Gly Ile Tyr Gly Pro Val Phe Gly Pro Tyr Gly Pro Gly Ile
            355                 360                 365

Leu Ala Ala Ala Ala Gly Ile Tyr Val Phe Gly Pro Gly Val Phe
370                 375                 380

Gly Pro Tyr Gly Pro Gly Ala Leu Gly Pro Gly Val Phe Gly Pro Tyr
385                 390                 395                 400

Gly Pro Gly Ala Val Ala Ala Ala Ala Gly Pro Gly Ile Tyr Gly
                405                 410                 415

Pro Gly Val Phe Gly Pro Ile Ala Val Ala Ala Ala Ala Gly Ile
            420                 425                 430

Tyr Gly Ala Gly Pro Gly Ile Tyr Gly Pro Tyr Gly Pro Gly Ile Leu
            435                 440                 445

Gly Pro Gly Ala Gly Val Phe Gly Ile Gly Pro Tyr Gly Pro Gly Ala
            450                 455                 460

Val Ala Ala Ala Ala Gly Ile Tyr Gly Pro Gly Val Phe Gly Pro
465                 470                 475                 480

Tyr Gly Pro Gly Ile Leu Ala Ala Ala Ala Gly Pro Gly Ala Gly
            485                 490                 495

Ile Tyr Gly Pro Gly Ala Leu Gly Ile Asn Gly Pro Gly Ala Gly Ile
            500                 505                 510

Tyr Gly Pro Gly Val Phe Gly Pro Gly Ile Leu Ala Ala Ala Ala
            515                 520                 525

Gly Ile Tyr Val Phe Gly Pro Gly Val Phe Gly Pro Tyr Gly Pro Gly
            530                 535                 540

Ala Val Ala Ala Ala Ala Gly Ile Tyr Gly Ala Gly Pro Gly Val
545                 550                 555                 560

Phe Gly Pro Tyr Gly Pro Gly Ile Leu Gly Ala Gly Val Phe Gly Pro
            565                 570                 575

Gly Val Phe Gly Pro Tyr Ala Val Ala Ala Ala Ala Gly Pro Gly
            580                 585                 590

Ala Gly Val Phe Gly Pro Gly Ala Ile
            595                 600

<210> SEQ ID NO 14
<211> LENGTH: 601
<212> TYPE: PRT
<213> ORGANISM: Artificial Sequence
<220> FEATURE:
<223> OTHER INFORMATION: PRT1083

<400> SEQUENCE: 14

Met His His His His His Ser Ser Gly Ser Gly Leu Gly Val
1               5                   10                  15

Phe Gly Leu Tyr Gly Thr Gly Ala Ser Ala Ala Ala Ala Gly Ile
            20                  25                  30

Ala Gly Thr Gly Ser Gly Val Phe Gly Thr Gly Ile Ser Gly Ile Tyr
            35                  40                  45

Gly Leu Gly Val Phe Gly Leu Gly Val Phe Gly Thr Gly Ser Ser Ala
            50                  55                  60

Ala Ala Ala Ala Gly Thr Gly Ile Tyr Gly Leu Gly Val Phe Gly Leu
65                  70                  75                  80

Ser Ala Ser Ala Ala Ala Ala Gly Thr Gly Ser Gly Val Phe Gly
            85                  90                  95
```

```
Thr Gly Ala Ser Gly Ile Tyr Gly Leu Gly Val Phe Gly Leu Gly Val
            100                 105                 110

Phe Gly Thr Gly Ser Ser Ala Ala Ala Ala Gly Ile Tyr Gly Ser
        115                 120                 125

Gly Leu Gly Val Phe Gly Leu Tyr Gly Ser Ala Ala Ala Ala Gly
    130                 135                 140

Thr Gly Ser Gly Ile Tyr Gly Ile Gly Leu Tyr Gly Thr Gly Ala Ser
145                 150                 155                 160

Gly Thr Gly Ile Tyr Gly Leu Gly Val Phe Gly Leu Ser Ala Ser Ala
                165                 170                 175

Ala Ala Ala Ala Gly Ser Gly Val Phe Gly Thr Gly Ile Tyr Gly Leu
            180                 185                 190

Tyr Ala Ser Ala Ala Ala Ala Gly Ile Tyr Gly Ser Gly Leu Gly
        195                 200                 205

Val Phe Gly Leu Tyr Gly Thr Gly Ile Ser Gly Ser Gly Val Phe Gly
        210                 215                 220

Leu Gly Val Phe Gly Leu Tyr Ala Ser Ala Ala Ala Ala Gly Leu
225                 230                 235                 240

Gly Val Phe Gly Leu Tyr Gly Thr Gly Ser Ser Ala Ala Ala Ala
                245                 250                 255

Gly Ile Tyr Gly Tyr Gly Leu Gly Val Phe Gly Leu Tyr Gly Thr Gly
            260                 265                 270

Ala Ser Gly Ile Ala Gly Thr Gly Ser Gly Ile Tyr Gly Leu Gly Val
                275                 280                 285

Phe Gly Thr Gly Ile Ser Ala Ala Ala Ala Gly Leu Gly Val Phe
        290                 295                 300

Gly Leu Tyr Gly Thr Gly Ala Ser Ala Ala Ala Ala Gly Ile Tyr
305                 310                 315                 320

Gly Leu Gly Val Phe Gly Thr Gly Ile Tyr Gly Thr Gly Ser Ser Gly
                325                 330                 335

Leu Gly Val Phe Gly Leu Tyr Gly Thr Gly Ser Ser Ala Ala Ala Ala
                340                 345                 350

Ala Gly Ile Tyr Gly Leu Gly Val Phe Gly Leu Tyr Gly Thr Gly Ile
            355                 360                 365

Ser Ala Ala Ala Ala Gly Ile Tyr Val Phe Gly Leu Gly Val Phe
        370                 375                 380

Gly Leu Tyr Gly Thr Gly Ala Ser Gly Leu Gly Val Phe Gly Leu Tyr
385                 390                 395                 400

Gly Thr Gly Ala Ser Ala Ala Ala Ala Gly Thr Gly Ile Tyr Gly
                405                 410                 415

Leu Gly Val Phe Gly Leu Ser Ala Ser Ala Ala Ala Ala Gly Ile
                420                 425                 430

Tyr Gly Ser Gly Thr Gly Ile Tyr Gly Leu Tyr Gly Thr Gly Ile Ser
        435                 440                 445

Gly Thr Gly Ser Gly Val Phe Gly Ile Gly Leu Tyr Gly Thr Gly Ala
    450                 455                 460

Ser Ala Ala Ala Ala Gly Ile Tyr Gly Leu Gly Val Phe Gly Leu
465                 470                 475                 480

Tyr Gly Thr Gly Ile Ser Ala Ala Ala Ala Gly Thr Gly Ser Gly
                485                 490                 495

Ile Tyr Gly Thr Gly Ala Ser Gly Ile Ala Gly Thr Gly Ser Gly Ile
            500                 505                 510
```

```
Tyr Gly Leu Gly Val Phe Gly Thr Gly Ile Ser Ala Ala Ala Ala
            515                 520                 525

Gly Ile Tyr Val Phe Gly Leu Gly Val Phe Gly Leu Tyr Gly Thr Gly
            530                 535                 540

Ala Ser Ala Ala Ala Ala Gly Ile Tyr Gly Ser Gly Leu Gly Val
545                 550                 555                 560

Phe Gly Leu Tyr Gly Thr Gly Ile Ser Gly Ser Gly Val Phe Gly Leu
                565                 570                 575

Gly Val Phe Gly Leu Tyr Ala Ser Ala Ala Ala Ala Gly Thr Gly
            580                 585                 590

Ser Gly Val Phe Gly Thr Gly Ala Ser
            595                 600

<210> SEQ ID NO 15
<211> LENGTH: 601
<212> TYPE: PRT
<213> ORGANISM: Artificial Sequence
<220> FEATURE:
<223> OTHER INFORMATION: PRT826

<400> SEQUENCE: 15

Met His His His His His Thr Thr Gly Thr Thr Gly Pro Gly Gln
1               5                   10                  15

Gln Gly Pro Tyr Gly Pro Gly Ala Thr Ala Ala Ala Ala Gly Gln
            20                  25                  30

Asn Gly Pro Gly Thr Gly Gln Gln Gly Pro Gly Gln Thr Gly Gln Tyr
            35                  40                  45

Gly Pro Gly Gln Gln Gly Pro Gly Gln Gln Gly Pro Gly Thr Thr Ala
50                  55                  60

Ala Ala Ala Ala Gly Pro Gly Gln Tyr Gly Pro Gly Gln Gln Gly Pro
65                  70                  75                  80

Thr Ala Thr Ala Ala Ala Ala Gly Pro Gly Thr Gly Gln Gln Gly
            85                  90                  95

Pro Gly Ala Thr Gly Gln Tyr Gly Pro Gly Gln Gln Gly Pro Gly Gln
            100                 105                 110

Gln Gly Pro Gly Thr Thr Ala Ala Ala Ala Gly Gln Tyr Gly Thr
            115                 120                 125

Gly Pro Gly Gln Gln Gly Pro Tyr Gly Thr Ala Ala Ala Ala Gly
            130                 135                 140

Pro Gly Thr Gly Gln Tyr Gly Gln Gly Pro Tyr Gly Pro Gly Ala Thr
145                 150                 155                 160

Gly Pro Gly Gln Tyr Gly Pro Gly Gln Gln Gly Pro Thr Ala Thr Ala
                165                 170                 175

Ala Ala Ala Gly Thr Gly Gln Gln Gly Pro Gly Gln Tyr Gly Pro
            180                 185                 190

Tyr Ala Thr Ala Ala Ala Ala Gly Gln Tyr Gly Thr Gly Pro Gly
            195                 200                 205

Gln Gln Gly Pro Tyr Gly Pro Gly Thr Gly Thr Gly Gln Gln Gly
            210                 215                 220

Pro Gly Gln Gln Gly Pro Tyr Gly Thr Ala Ala Ala Ala Gly Pro
225                 230                 235                 240

Gly Gln Gln Gly Pro Tyr Gly Pro Gly Thr Thr Ala Ala Ala Ala
            245                 250                 255

Gly Gln Tyr Gly Tyr Gly Pro Gly Gln Gln Gly Pro Tyr Gly Pro Gly
            260                 265                 270
```

```
Ala Thr Gly Gln Asn Gly Pro Gly Thr Gly Gln Tyr Gly Pro Gly Gln
            275                 280                 285

Gln Gly Pro Gly Gln Thr Ala Ala Ala Ala Gly Pro Gly Gln Gln
290                 295                 300

Gly Pro Tyr Gly Pro Gly Ala Thr Ala Ala Ala Ala Gly Gln Tyr
305                 310                 315                 320

Gly Pro Gly Gln Gln Gly Pro Gly Gln Tyr Gly Pro Gly Thr Thr Gly
                325                 330                 335

Pro Gly Gln Gln Gly Pro Tyr Gly Pro Gly Thr Thr Ala Ala Ala
                340                 345                 350

Ala Gly Gln Tyr Gly Pro Gly Gln Gln Gly Pro Tyr Gly Pro Gly Gln
            355                 360                 365

Thr Ala Ala Ala Ala Gly Gln Tyr Gln Gly Pro Gly Gln Gln
370                 375                 380

Gly Pro Tyr Gly Pro Gly Ala Thr Gly Pro Gly Gln Gln Gly Pro Tyr
385                 390                 395                 400

Gly Pro Gly Ala Thr Ala Ala Ala Ala Gly Pro Gly Gln Tyr Gly
                405                 410                 415

Pro Gly Gln Gln Gly Pro Thr Ala Thr Ala Ala Ala Ala Gly Gln
                420                 425                 430

Tyr Gly Thr Gly Pro Gly Gln Tyr Gly Pro Tyr Gly Pro Gly Gln Thr
            435                 440                 445

Gly Pro Gly Thr Gly Gln Gln Gly Gln Gly Pro Tyr Gly Pro Gly Ala
450                 455                 460

Thr Ala Ala Ala Ala Gly Gln Tyr Gly Pro Gly Gln Gln Gly Pro
465                 470                 475                 480

Tyr Gly Pro Gly Gln Thr Ala Ala Ala Ala Gly Pro Gly Thr Gly
                485                 490                 495

Gln Tyr Gly Pro Gly Ala Thr Gly Gln Asn Gly Pro Gly Thr Gly Gln
                500                 505                 510

Tyr Gly Pro Gly Gln Gln Gly Pro Gly Gln Thr Ala Ala Ala Ala
            515                 520                 525

Gly Gln Tyr Gln Gln Gly Pro Gly Gln Gln Gly Pro Tyr Gly Pro Gly
530                 535                 540

Ala Thr Ala Ala Ala Ala Ala Gly Gln Tyr Gly Thr Gly Pro Gly Gln
545                 550                 555                 560

Gln Gly Pro Tyr Gly Pro Gly Gln Thr Gly Thr Gly Gln Gln Gly Pro
                565                 570                 575

Gly Gln Gln Gly Pro Tyr Ala Thr Ala Ala Ala Ala Gly Pro Gly
                580                 585                 590

Thr Gly Gln Gln Gly Pro Gly Ala Thr
            595                 600

<210> SEQ ID NO 16
<211> LENGTH: 601
<212> TYPE: PRT
<213> ORGANISM: Artificial Sequence
<220> FEATURE:
<223> OTHER INFORMATION: PRT1127

<400> SEQUENCE: 16

Met His His His His His Thr Thr Gly Thr Thr Gly Pro Gly Val
1               5                   10                  15

Phe Gly Pro Tyr Gly Pro Gly Ala Thr Ala Ala Ala Ala Ala Gly Ile
                20                  25                  30
```

```
Asn Gly Pro Gly Thr Gly Val Phe Gly Pro Gly Ile Thr Gly Ile Tyr
         35                  40                  45

Gly Pro Gly Val Phe Gly Pro Gly Val Phe Gly Pro Gly Thr Thr Ala
 50                  55                  60

Ala Ala Ala Ala Gly Pro Gly Ile Tyr Gly Pro Gly Val Phe Gly Pro
 65                  70                  75                  80

Thr Ala Thr Ala Ala Ala Ala Gly Pro Gly Thr Gly Val Phe Gly
                 85                  90                  95

Pro Gly Ala Thr Gly Ile Tyr Gly Pro Gly Val Phe Gly Pro Gly Val
            100                 105                 110

Phe Gly Pro Gly Thr Thr Ala Ala Ala Ala Gly Ile Tyr Gly Thr
            115                 120                 125

Gly Pro Gly Val Phe Gly Pro Tyr Gly Thr Ala Ala Ala Ala Gly
        130                 135                 140

Pro Gly Thr Gly Ile Tyr Gly Ile Gly Pro Tyr Gly Pro Gly Ala Thr
145                 150                 155                 160

Gly Pro Gly Ile Tyr Gly Pro Gly Val Phe Gly Pro Thr Ala Thr Ala
                165                 170                 175

Ala Ala Ala Ala Gly Thr Gly Val Phe Gly Pro Gly Ile Tyr Gly Pro
        180                 185                 190

Tyr Ala Thr Ala Ala Ala Ala Gly Ile Tyr Gly Thr Gly Pro Gly
            195                 200                 205

Val Phe Gly Pro Tyr Gly Pro Gly Ile Thr Gly Thr Gly Val Phe Gly
        210                 215                 220

Pro Gly Val Phe Gly Pro Tyr Ala Thr Ala Ala Ala Ala Gly Pro
225                 230                 235                 240

Gly Val Phe Gly Pro Tyr Gly Pro Gly Thr Thr Ala Ala Ala Ala
            245                 250                 255

Gly Ile Tyr Gly Tyr Gly Pro Gly Val Phe Gly Pro Tyr Gly Pro Gly
            260                 265                 270

Ala Thr Gly Ile Asn Gly Pro Gly Thr Gly Ile Tyr Gly Pro Gly Val
        275                 280                 285

Phe Gly Pro Gly Ile Thr Ala Ala Ala Ala Gly Pro Gly Val Phe
        290                 295                 300

Gly Pro Tyr Gly Pro Gly Ala Thr Ala Ala Ala Ala Gly Ile Tyr
305                 310                 315                 320

Gly Pro Gly Val Phe Gly Pro Gly Ile Tyr Gly Pro Gly Thr Thr Gly
            325                 330                 335

Pro Gly Val Phe Gly Pro Tyr Gly Pro Gly Thr Thr Ala Ala Ala
            340                 345                 350

Ala Gly Ile Tyr Gly Pro Gly Val Phe Gly Pro Tyr Gly Pro Gly Ile
        355                 360                 365

Thr Ala Ala Ala Ala Gly Ile Tyr Val Phe Gly Pro Gly Val Phe
            370                 375                 380

Gly Pro Tyr Gly Pro Gly Ala Thr Gly Pro Gly Val Phe Gly Pro Tyr
385                 390                 395                 400

Gly Pro Gly Ala Thr Ala Ala Ala Ala Gly Pro Gly Ile Tyr Gly
                405                 410                 415

Pro Gly Val Phe Gly Pro Thr Ala Thr Ala Ala Ala Ala Gly Ile
            420                 425                 430

Tyr Gly Thr Gly Pro Gly Ile Tyr Gly Pro Tyr Gly Pro Gly Ile Thr
            435                 440                 445
```

```
Gly Pro Gly Thr Gly Val Phe Gly Ile Gly Pro Tyr Gly Pro Gly Ala
    450                 455                 460

Thr Ala Ala Ala Ala Gly Ile Tyr Gly Pro Gly Val Phe Gly Pro
465                 470                 475                 480

Tyr Gly Pro Gly Ile Thr Ala Ala Ala Gly Pro Gly Thr Gly
            485                 490                 495

Ile Tyr Gly Pro Gly Ala Thr Gly Ile Asn Gly Pro Gly Thr Gly Ile
            500                 505                 510

Tyr Gly Pro Gly Val Phe Gly Pro Gly Ile Thr Ala Ala Ala Ala
            515                 520                 525

Gly Ile Tyr Val Phe Gly Pro Gly Val Phe Gly Pro Tyr Gly Pro Gly
    530                 535                 540

Ala Thr Ala Ala Ala Ala Gly Ile Tyr Gly Thr Gly Pro Gly Val
545                 550                 555                 560

Phe Gly Pro Tyr Gly Pro Gly Ile Thr Gly Thr Gly Val Phe Gly Pro
            565                 570                 575

Gly Val Phe Gly Pro Tyr Ala Thr Ala Ala Ala Ala Gly Pro Gly
            580                 585                 590

Thr Gly Val Phe Gly Pro Gly Ala Thr
    595                 600

<210> SEQ ID NO 17
<211> LENGTH: 12
<212> TYPE: PRT
<213> ORGANISM: Artificial Sequence
<220> FEATURE:
<223> OTHER INFORMATION: HisTag(S)

<400> SEQUENCE: 17

Met His His His His His His Ser Ser Gly Ser Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: HisTag(A)

<400> SEQUENCE: 18

Met His His His His His His Ala Ala Gly Ala Ala
1               5                   10

<210> SEQ ID NO 19
<211> LENGTH: 590
<212> TYPE: PRT
<213> ORGANISM: Artificial Sequence
<220> FEATURE:
<223> OTHER INFORMATION: Met-PRT410

<400> SEQUENCE: 19

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Gly Pro
    50                  55                  60
```

```
Gly Gln Gln Gly Pro Ser Ala Ser Ala Ala Ala Ala Gly Pro Gly
 65                  70                  75                  80

Ser Gly Gln Gln Gly Pro Gly Ala Ser Gly Gln Tyr Gly Pro Gly Gln
                 85                  90                  95

Gln Gly Pro Gly Gln Gln Gly Pro Gly Ser Ala Ala Ala Ala
                100                 105                 110

Gly Gln Tyr Gly Ser Gly Pro Gly Gln Gly Pro Tyr Gly Ser Ala
            115                 120                 125

Ala Ala Ala Ala Gly Pro Gly Ser Gly Gln Tyr Gly Gln Gly Pro Tyr
130                 135                 140

Gly Pro Gly Ala Ser Gly Pro Gln Tyr Gly Pro Gly Gln Gln Gly
145                 150                 155                 160

Pro Ser Ala Ser Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
            180                 185                 190

Gly Ser Gly Pro Gly Gln Gln Gly Pro Tyr Gly Pro Gly Gln Ser Gly
            195                 200                 205

Ser Gly Gln Gln Gly Pro Gly Gln Gln Gly Pro Tyr Ala Ser Ala Ala
    210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Tyr Gly Pro Gly Gln Gln Gly
                245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala
            275                 280                 285

Gly Pro Gly Gln Gln Gly Pro Tyr Gly Pro Gly Ala Ser Ala Ala Ala
    290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
            325                 330                 335

Ser Ala Ala Ala Ala Ala Gly Gln Tyr Gly Pro Gly Gln Gln Gly Pro
            340                 345                 350

Tyr Gly Pro Gly Gln Ser Ala Ala Ala Ala Gly Gln Tyr Gln Gln
            355                 360                 365

Gly Pro Gly Gln Gln Gly Pro Tyr Gly Pro Gly Ala Ser Gly Pro Gly
    370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gly Pro Ser Ala Ser Ala Ala
            405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
            435                 440                 445

Tyr Gly Pro Gly Ala Ser Ala Ala Ala Ala Gly Gln Tyr Gly Pro
            450                 455                 460

Gly Gln Gln Gly Pro Tyr Gly Pro Gly Gln Ser Ala Ala Ala Ala
465                 470                 475                 480
```

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
            500                 505                 510

Ala Ala Ala Ala Gly Gln Tyr Gln Gln Gly Pro Gly Gln Gln Gly
        515                 520                 525

Pro Tyr Gly Pro Gly Ala Ser Ala Ala Ala Ala Gly Gln Tyr Gly
        530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser
            580                 585                 590

<210> SEQ ID NO 20
<211> LENGTH: 597
<212> TYPE: PRT
<213> ORGANISM: Artificial Sequence
<220> FEATURE:
<223> OTHER INFORMATION: Met-PRT380

<400> SEQUENCE: 20

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Ala Ala Ala Ala Gly Gln Tyr Gly Pro Gly Gln Gln Gly
        35                  40                  45

Pro Gly Gln Gln Gly Pro Gly Ser Ser Ala Ala Ala Ala Gly Pro
    50                  55                  60

Gly Gln Tyr Gly Pro Gly Gln Gln Pro Ser Ala Ser Ala Ala Ala
65                  70                  75                  80

Ala Ala Gly Pro Gly Ser Gln Gln Gly Pro Gly Ala Ser Ala Ala
            85                  90                  95

Ala Ala Ala Gly Gln Tyr Gly Pro Gly Gln Gln Gly Pro Gly Gln Gln
        100                 105                 110

Gly Pro Gly Ser Ser Ala Ala Ala Ala Gly Gln Tyr Gly Ser Gly
        115                 120                 125

Pro Gly Gln Gln Gly Pro Tyr Gly Ser Ala Ala Ala Ala Gly Pro
    130                 135                 140

Gly Ser Gly Gln Tyr Gly Gln Gly Pro Tyr Gly Pro Gly Ala Ser Ala
145                 150                 155                 160

Ala Ala Ala Gly Pro Gly Gln Tyr Gly Pro Gly Gln Gln Gly Pro
        165                 170                 175

Ser Ala Ser Ala Ala Ala Ala Gly Ser Gly Gln Gln Gly Pro Gly
        180                 185                 190

Gln Tyr Gly Pro Tyr Ala Ser Ala Ala Ala Ala Gly Gln Tyr Gly
    195                 200                 205

Ser Gly Pro Gly Gln Gly Pro Tyr Gly Pro Gly Gln Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Gly Pro Gly Gln Gln Gly Pro Tyr Gly
            245                 250                 255

```
Pro Gly Ser Ser Ala Ala Ala Ala Gly Gln Tyr Gly Tyr Gly Pro
            260                 265                 270

Gly Gln Gln Gly Pro Tyr Gly Pro Gly Ala Ser Ala Ala Ala Ala
        275                 280                 285

Gly Gln Asn Gly Pro Gly Ser Gly Gln Tyr Gly Pro Gly Gln Gln Gly
        290                 295                 300

Pro Gly Gln Ser Ala Ala Ala Ala Gly Pro Gly Gln Gln Gly Pro
305                 310                 315                 320

Tyr Gly Pro Gly Ala Ser Ala Ala Ala Ala Gly Gln Tyr Gly Pro
                325                 330                 335

Gly Gln Gln Gly Pro Gly Gln Tyr Gly Pro Gly Ser Ser Ala Ala
        340                 345                 350

Ala Ala Gly Pro Gly Gln Gln Gly Pro Tyr Gly Pro Gly Ser Ser Ala
        355                 360                 365

Ala Ala Ala Gly Gln Tyr Gly Pro Gly Gln Gln Gly Pro Tyr Gly
        370                 375                 380

Pro Gly Gln Ser Ala Ala Ala Ala Gly Gln Tyr Gln Gly Pro
385                 390                 395                 400

Gly Gln Gln Gly Pro Tyr Gly Pro Gly Ala Ser Ala Ala Ala Ala
        405                 410                 415

Gly Pro Gly Gln Gln Gly Pro Tyr Gly Pro Gly Ala Ser Ala Ala
        420                 425                 430

Ala Ala Gly Pro Gly Gln Tyr Gly Pro Gly Gln Gln Gly Pro Ser Ala
        435                 440                 445

Ser Ala Ala Ala Ala Gly Gln Tyr Gly Ser Gly Pro Gly Gln Tyr
450                 455                 460

Gly Pro Tyr Gly Pro Gly Gln Ser Ala Ala Ala Ala Gly Pro Gly
465                 470                 475                 480

Ser Gly Gln Gln Gly Gln Pro Tyr Gly Pro Gly Ala Ser Ala Ala
        485                 490                 495

Ala Ala Ala Gly Gln Tyr Gly Pro Gly Gln Gly Pro Tyr Gly Pro
        500                 505                 510

Gly Gln Ser Ala Ala Ala Ala Gly Pro Gly Ser Gly Gln Tyr Gly
        515                 520                 525

Pro Gly Ala Ser Ala Ala Ala Ala Gly Gln Asn Gly Pro Gly Ser
        530                 535                 540

Gly Gln Tyr Gly Pro Gly Gln Gln Gly Pro Gly Gln Ser Ala Ala Ala
545                 550                 555                 560

Ala Ala Gly Gln Tyr Gln Gln Gly Pro Gly Gln Gln Gly Pro Tyr Gly
        565                 570                 575

Pro Gly Ala Ser Ala Ala Ala Ala Gly Pro Gly Ser Gly Gln Gln
        580                 585                 590

Gly Pro Gly Ala Ser
        595

<210> SEQ ID NO 21
<211> LENGTH: 597
<212> TYPE: PRT
<213> ORGANISM: Artificial Sequence
<220> FEATURE:
<223> OTHER INFORMATION: Met-PRT313

<400> SEQUENCE: 21

Met Gly Pro Gly Gln Gly Pro Tyr Gly Pro Gly Ala Ser Ala Ala
1               5                   10                  15
```

-continued

Ala Ala Ala Gly Gly Asn Gly Pro Gly Ser Gly Gln Gln Gly Pro Gly
            20                  25                  30
Gly Ser Ala Ala Ala Ala Gly Gly Tyr Gly Pro Gly Gly Gln Gly
        35                  40                  45
Pro Gly Gln Gln Gly Pro Gly Ser Ser Ala Ala Ala Ala Gly Pro
    50                  55                  60
Gly Gly Tyr Gly Pro Gly Gly Gln Gly Pro Ser Ala Ser Ala Ala
65                  70                  75                  80
Ala Ala Gly Pro Gly Ser Gly Gln Gln Gly Pro Gly Ala Ser Ala Ala
                85                  90                  95
Ala Ala Ala Gly Gly Tyr Gly Pro Gly Gly Gln Gly Pro Gly Gln Gln
            100                 105                 110
Gly Pro Gly Ser Ser Ala Ala Ala Ala Gly Gly Tyr Gly Ser Gly
        115                 120                 125
Pro Gly Gln Gln Gly Pro Tyr Gly Ser Ala Ala Ala Ala Gly Pro
    130                 135                 140
Gly Ser Gly Gly Tyr Gly Gln Gly Pro Tyr Gly Pro Gly Ala Ser Ala
145                 150                 155                 160
Ala Ala Ala Ala Gly Pro Gly Gly Tyr Gly Pro Gly Gly Gln Gly Pro
            165                 170                 175
Ser Ala Ser Ala Ala Ala Ala Ala Gly Ser Gly Gln Gln Gly Pro Gly
            180                 185                 190
Gly Tyr Gly Pro Tyr Ala Ser Ala Ala Ala Ala Gly Gly Tyr Gly
        195                 200                 205
Ser Gly Pro Gly Gln Gln Gly Pro Tyr Gly Pro Gly Gly Ser Ala Ala
210                 215                 220
Ala Ala Ala Gly Ser Gly Gln Gln Gly Pro Gly Gln Gln Gly Pro Tyr
225                 230                 235                 240
Ala Ser Ala Ala Ala Ala Gly Pro Gly Gly Gln Gly Pro Tyr Gly
        245                 250                 255
Pro Gly Ser Ser Ala Ala Ala Ala Gly Gly Tyr Gly Tyr Gly Pro
    260                 265                 270
Gly Gly Gln Gly Pro Tyr Gly Pro Gly Ala Ser Ala Ala Ala Ala
        275                 280                 285
Gly Gly Asn Gly Pro Gly Ser Gly Tyr Gly Pro Gly Gln Gln Gly
        290                 295                 300
Pro Gly Gly Ser Ala Ala Ala Ala Gly Pro Gly Gly Gln Gly Pro
305                 310                 315                 320
Tyr Gly Pro Gly Ala Ser Ala Ala Ala Ala Gly Gly Tyr Gly Pro
            325                 330                 335
Gly Gly Gln Gly Pro Gly Gly Tyr Gly Pro Gly Ser Ser Ala Ala Ala
                340                 345                 350
Ala Ala Gly Pro Gly Gly Gln Gly Pro Tyr Gly Pro Gly Ser Ser Ala
            355                 360                 365
Ala Ala Ala Ala Gly Gly Tyr Gly Pro Gly Gln Gln Gly Pro Tyr Gly
            370                 375                 380
Pro Gly Gly Ser Ala Ala Ala Ala Gly Gly Tyr Gln Gln Gly Pro
385                 390                 395                 400
Gly Gly Gln Gly Pro Tyr Gly Pro Gly Ala Ser Ala Ala Ala Ala
        405                 410                 415
Gly Pro Gly Gly Gln Gly Pro Tyr Gly Pro Gly Ala Ser Ala Ala Ala
            420                 425                 430

```
Ala Ala Gly Pro Gly Gly Tyr Gly Pro Gly Gln Gly Pro Ser Ala
            435                 440                 445
Ser Ala Ala Ala Ala Gly Gly Tyr Gly Ser Gly Pro Gly Gly Tyr
    450                 455                 460
Gly Pro Tyr Gly Pro Gly Ser Ala Ala Ala Ala Gly Pro Gly
465                 470                 475                 480
Ser Gly Gln Gln Gly Gln Gly Pro Tyr Gly Pro Gly Ala Ser Ala
                    485                 490                 495
Ala Ala Ala Gly Gly Tyr Gly Pro Gln Gln Gly Pro Tyr Gly Pro
            500                 505                 510
Gly Gly Ser Ala Ala Ala Ala Gly Pro Gly Ser Gly Gly Tyr Gly
            515                 520                 525
Pro Gly Ala Ser Ala Ala Ala Ala Gly Gly Asn Gly Pro Gly Ser
            530                 535                 540
Gly Gly Tyr Gly Pro Gly Gln Gln Pro Gly Gly Ser Ala Ala Ala
545                 550                 555                 560
Ala Ala Gly Gly Tyr Gln Gln Gly Pro Gly Gln Gly Pro Tyr Gly
                    565                 570                 575
Pro Gly Ala Ser Ala Ala Ala Ala Gly Pro Gly Ser Gly Gln Gln
            580                 585                 590
Gly Pro Gly Ala Ser
        595

<210> SEQ ID NO 22
<211> LENGTH: 601
<212> TYPE: PRT
<213> ORGANISM: Artificial Sequence
<220> FEATURE:
<223> OTHER INFORMATION: PRT410

<400> SEQUENCE: 22

Met His His His His His Ser Ser Gly Ser Ser Gly Pro Gly Gln
1               5                   10                  15
Gln Gly Pro Tyr Gly Pro Gly Ala Ser Ala Ala Ala Ala Gly Gln
            20                  25                  30
Asn Gly Pro Gly Ser Gly Gln Gln Gly Pro Gly Gln Ser Gly Gln Tyr
            35                  40                  45
Gly Pro Gly Gln Gln Gly Pro Gln Gln Gly Pro Gly Ser Ser Ala
    50                  55                  60
Ala Ala Ala Ala Gly Pro Gly Gln Tyr Gly Pro Gly Gln Gln Gly Pro
65                  70                  75                  80
Ser Ala Ser Ala Ala Ala Ala Ala Gly Pro Gly Ser Gly Gln Gln Gly
                85                  90                  95
Pro Gly Ala Ser Gly Gln Tyr Gly Pro Gly Gln Gln Gly Pro Gln
            100                 105                 110
Gln Gly Pro Gly Ser Ser Ala Ala Ala Ala Gly Gln Tyr Gly Ser
            115                 120                 125
Gly Pro Gly Gln Gln Gly Pro Tyr Gly Ser Ala Ala Ala Ala Gly
            130                 135                 140
Pro Gly Ser Gly Gln Tyr Gly Gln Gly Pro Tyr Gly Pro Gly Ala Ser
145                 150                 155                 160
Gly Pro Gly Gln Tyr Gly Pro Gly Gln Gln Gly Pro Ser Ala Ser Ala
                165                 170                 175
Ala Ala Ala Gly Ser Gly Gln Gln Gly Pro Gly Gln Tyr Gly Pro
            180                 185                 190
```

```
Tyr Ala Ser Ala Ala Ala Ala Gly Gln Tyr Gly Ser Gly Pro Gly
            195                 200                 205

Gln Gln Gly Pro Tyr Gly Pro Gly Gln Ser Gly Ser Gly Gln Gln Gly
    210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
            275                 280                 285

Gln Gly Pro Gly Gln Ser Ala Ala Ala Ala Gly Pro Gly Gln Gln
    290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
                325                 330                 335

Pro Gly Gln Gln Gly Pro Tyr Gly Pro Gly Ser Ser Ala Ala Ala
                340                 345                 350

Ala Gly Gln Tyr Gly Pro Gly Gln Gln Gly Pro Tyr Gly Pro Gly Gln
            355                 360                 365

Ser Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
                420                 425                 430

Tyr Gly Ser Gly Pro Gly Gln Tyr Gly Pro Tyr Gly Pro Gly Gln Ser
    435                 440                 445

Gly Pro Gly Ser Gly Gln Gln Gly Gln Gly Pro Tyr Gly Pro Gly Ala
    450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala
    515                 520                 525

Gly Gln Tyr Gln Gln Gly Pro Gly Gln Gln Gly Pro Tyr Gly Pro Gly
    530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
                580                 585                 590

Ser Gly Gln Gln Gly Pro Gly Ala Ser
    595                 600
```

```
<210> SEQ ID NO 23
<211> LENGTH: 608
<212> TYPE: PRT
<213> ORGANISM: Artificial Sequence
<220> FEATURE:
<223> OTHER INFORMATION: PRT380

<400> SEQUENCE: 23

Met His His His His His Ser Ser Gly Ser Ser Pro Gly Gln
1               5                   10                  15

Gln Gly Pro Tyr Gly Pro Gly Ala Ser Ala Ala Ala Gly Gln
                20                  25                  30

Asn Gly Pro Gly Ser Gly Gln Gly Pro Gly Gln Ser Ala Ala
            35                  40                  45

Ala Ala Gly Gln Tyr Gly Pro Gly Gln Gln Pro Gly Gln Gly
    50                  55                  60

Pro Gly Ser Ser Ala Ala Ala Ala Gly Pro Gly Gln Tyr Gly Pro
65                  70                  75                  80

Gly Gln Gln Gly Pro Ser Ala Ser Ala Ala Ala Gly Pro Gly
                85                  90                  95

Ser Gly Gln Gln Gly Pro Gly Ala Ser Ala Ala Ala Ala Gly Gln
                100                 105                 110

Tyr Gly Pro Gly Gln Gln Gly Pro Gly Gln Gln Gly Pro Ser Ser
            115                 120                 125

Ala Ala Ala Ala Ala Gly Gln Tyr Gly Ser Gly Pro Gly Gln Gln Gly
    130                 135                 140

Pro Tyr Gly Ser Ala Ala Ala Ala Gly Pro Gly Ser Gly Gln Tyr
145                 150                 155                 160

Gly Gln Gly Pro Tyr Gly Pro Gly Ala Ser Ala Ala Ala Ala Gly
                165                 170                 175

Pro Gly Gln Tyr Gly Pro Gly Gln Gln Gly Pro Ser Ala Ser Ala Ala
            180                 185                 190

Ala Ala Ala Gly Ser Gly Gln Gln Gly Pro Gly Gln Tyr Gly Pro Tyr
    195                 200                 205

Ala Ser Ala Ala Ala Ala Gly Gln Tyr Gly Ser Gly Pro Gly Gln
    210                 215                 220

Gln Gly Pro Tyr Gly Pro Gly Gln Ser Ala Ala Ala Ala Gly Ser
225                 230                 235                 240

Gly Gln Gln Gly Pro Gly Gln Gly Pro Tyr Ala Ser Ala Ala
                245                 250                 255

Ala Ala Gly Pro Gly Gln Gln Gly Pro Tyr Gly Pro Gly Ser Ser Ala
            260                 265                 270

Ala Ala Ala Gly Gln Tyr Gly Tyr Gly Pro Gly Gln Gln Gly Pro
    275                 280                 285

Tyr Gly Pro Gly Ala Ser Ala Ala Ala Gly Gln Asn Gly Pro
290                 295                 300

Gly Ser Gly Gln Tyr Gly Pro Gly Gln Gly Pro Gln Ser Ala
305                 310                 315                 320

Ala Ala Ala Gly Pro Gly Gln Gln Gly Pro Tyr Gly Pro Gly Ala
                325                 330                 335

Ser Ala Ala Ala Ala Gly Gln Tyr Gly Pro Gly Gln Gln Gly Pro
            340                 345                 350

Gly Gln Tyr Gly Pro Gly Ser Ser Ala Ala Ala Ala Gly Pro Gly
    355                 360                 365
```

-continued

```
Gln Gln Gly Pro Tyr Gly Pro Gly Ser Ser Ala Ala Ala Ala Ala Gly
    370                 375                 380
Gln Tyr Gly Pro Gly Gln Gln Gly Pro Tyr Gly Pro Gly Gln Ser Ala
385                 390                 395                 400
Ala Ala Ala Ala Gly Gln Tyr Gln Gln Gly Pro Gly Gln Gln Gly Pro
                405                 410                 415
Tyr Gly Pro Gly Ala Ser Ala Ala Ala Ala Gly Pro Gly Gln Gln
            420                 425                 430
Gly Pro Tyr Gly Pro Gly Ala Ser Ala Ala Ala Ala Gly Pro Gly
                435                 440                 445
Gln Tyr Gly Pro Gly Gln Gln Gly Pro Ser Ala Ser Ala Ala Ala Ala
    450                 455                 460
Ala Gly Gln Tyr Gly Ser Gly Pro Gly Gln Tyr Gly Pro Tyr Gly Pro
465                 470                 475                 480
Gly Gln Ser Ala Ala Ala Ala Ala Gly Pro Gly Ser Gly Gln Gln Gly
                485                 490                 495
Gln Gly Pro Tyr Gly Pro Gly Ala Ser Ala Ala Ala Ala Gly Gln
                500                 505                 510
Tyr Gly Pro Gly Gln Gln Gly Pro Tyr Gly Pro Gly Gln Ser Ala Ala
    515                 520                 525
Ala Ala Ala Gly Pro Gly Ser Gly Gln Tyr Gly Pro Gly Ala Ser Ala
530                 535                 540
Ala Ala Ala Gly Gln Asn Gly Pro Gly Ser Gly Tyr Gly Pro
545                 550                 555                 560
Gly Gln Gln Gly Pro Gln Ser Ala Ala Ala Ala Gly Gln Tyr
                565                 570                 575
Gln Gln Gly Pro Gly Gln Gln Gly Pro Tyr Gly Pro Gly Ala Ser Ala
    580                 585                 590
Ala Ala Ala Gly Pro Gly Ser Gly Gln Gln Gly Pro Gly Ala Ser
                595                 600                 605

<210> SEQ ID NO 24
<211> LENGTH: 547
<212> TYPE: PRT
<213> ORGANISM: Artificial Sequence
<220> FEATURE:
<223> OTHER INFORMATION: PRT219

<400> SEQUENCE: 24

Met His His His His His His His His Ser Ser Gly Ser Ser
1               5                   10                  15
Leu Gln Val Leu Phe Gln Gly Pro Ala Arg Ala Gly Ser Gln Gln
            20                  25                  30
Gly Pro Gly Gln Gln Gly Pro Gly Gln Gln Gly Pro Gly Gln Gln Gly
    35                  40                  45
Pro Tyr Gly Pro Gly Ala Ser Ala Ala Ala Ala Ala Gly Gly Tyr
    50                  55                  60
Gly Pro Gly Ser Gly Gln Gln Gly Pro Ser Gln Gln Gly Pro Gly Gln
65                  70                  75                  80
Gln Gly Pro Gly Gly Gln Gly Pro Tyr Gly Pro Gly Ala Ser Ala Ala
                85                  90                  95
Ala Ala Ala Ala Gly Gly Tyr Gly Pro Gly Ser Gln Gln Gly Pro
            100                 105                 110
Gly Gly Gln Gly Pro Tyr Gly Pro Gly Ser Ser Ala Ala Ala Ala Ala
    115                 120                 125
```

-continued

```
Ala Gly Gly Asn Gly Pro Gly Ser Gly Gln Gln Ala Gly Gln Gln
    130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln
            165                 170                 175

Pro Gly Gly Gln Gly Pro Tyr Gly Pro Gly Ala Ser Ala Ala Ala
                180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
    275                 280                 285

Tyr Gly Pro Gly Ala Ser Ala Ala Ser Ala Ala Ser Gly Gly Tyr Gly
        290                 295                 300

Pro Gly Ser Gly Gln Gln Gly Pro Gly Gln Gln Gly Pro Gly Gln
305                 310                 315                 320

Gly Pro Tyr Gly Pro Gly Ala Ser Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gln Gln Gly Pro Tyr Gly
    355                 360                 365

Pro Gly Ala Ser Ala Ala Ala Ala Ala Gly Gly Tyr Gly Pro Gly
        370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
    435                 440                 445

Gly Tyr Gly Pro Gly Ser Gly Gln Gln Gly Pro Gly Gln Gln Gly Pro
        450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525
```

Gly Gly Gln Gly Pro Tyr Gly Pro Gly Ala Ala Ser Ala Ala Val Val
            530                 535                 540
Val Val Val
545

<210> SEQ ID NO 25
<211> LENGTH: 601
<212> TYPE: PRT
<213> ORGANISM: Artificial Sequence
<220> FEATURE:
<223> OTHER INFORMATION: PRT1171

<400> SEQUENCE: 25

Met His His His His His Ser Ser Gly Ser Ser Gly Pro Gly Gly
1               5                   10                  15

Gln Gly Pro Tyr Gly Pro Gly Ala Ser Ala Ala Ala Ala Ala Ala
            20                  25                  30

Gly Pro Tyr Gly Tyr Gly Pro Gly Gly Gln Gly Pro Gly Gln Gln Gly
            35                  40                  45

Pro Tyr Gln Gln Gly Pro Gly Gln Gln Ser Gly Gly Asn Gly Pro Gly
    50                  55                  60

Gln Gln Gly Gly Tyr Gly Pro Gly Gln Gln Gly Pro Gly Ala Ala Ala
65                  70                  75                  80

Ala Ala Ala Ala Gly Pro Tyr Gly Tyr Gly Pro Gly Gln Gly Pro
                85                  90                  95

Gly Gln Gln Gly Pro Tyr Gln Gln Gly Pro Gly Gln Gln Ser Gly Gly
            100                 105                 110

Asn Gly Pro Gly Gln Gln Gly Gly Tyr Gly Pro Gly Gln Gln Gly Pro
            115                 120                 125

Gly Ala Ala Ala Ala Ala Ala Gly Pro Tyr Gly Tyr Gly Pro Gly
            130                 135                 140

Gly Gln Gly Pro Tyr Gln Gln Gly Pro Gly Gln Gln Ser Gly Gly Asn
145                 150                 155                 160

Gly Pro Gly Gln Gln Gly Gly Tyr Gly Pro Gly Gln Gln Gly Pro Gly
            165                 170                 175

Ala Ala Ala Ala Ala Ala Ala Gly Pro Tyr Gly Tyr Gly Pro Gly Gly
            180                 185                 190

Gln Gly Pro Tyr Gln Gln Gly Pro Gly Gln Gln Ser Gly Gly Asn Gly
            195                 200                 205

Pro Gly Gln Gln Gly Gly Tyr Gly Pro Gly Gln Gln Gly Pro Gly Ala
            210                 215                 220

Ala Ala Ala Ala Ala Gly Pro Tyr Gly Pro Gly Gln Gln Gly Pro
225                 230                 235                 240

Tyr Gln Gln Gly Pro Gly Gln Gln Asn Gly Gln Gln Gly Pro Gly Gly
            245                 250                 255

Gln Gln Gly Pro Gly Gln Gln Pro Gly Ala Ala Ala Ala Ala Ala
            260                 265                 270

Gly Pro Tyr Gly Pro Gly Gln Gln Pro Tyr Gln Gln Gly Pro Gly
            275                 280                 285

Gln Gln Gly Asn Gly Gln Gln Gly Pro Gly Gln Gln Gly Pro Gly Gln
            290                 295                 300

Gln Pro Gly Ala Ala Ala Ala Ala Ala Gly Pro Tyr Gly Pro Gly
305                 310                 315                 320

Gln Gln Gly Pro Tyr Gln Gln Gly Pro Gly Gln Gln Gly Pro Gly Gln
            325                 330                 335

```
Gln Gly Pro Gly Gln Gln Pro Gly Ala Ala Ala Ala Ala Ala Gly
            340                 345                 350
Pro Tyr Gly Pro Gly Gln Gln Gly Pro Tyr Gln Gln Gly Pro Gly Gln
        355                 360                 365
Gln Gly Pro Gly Gln Gln Gly Pro Gly Gln Pro Gly Ala Ala Ala
    370                 375                 380
Ala Ala Ala Ala Gly Pro Gly Gly Tyr Gly Pro Gly Gln Gly Pro
385                 390                 395                 400
Gly Gln Gln Gly Pro Gly Gln Gly Pro Ser Pro Gly Ala Ala Ala
            405                 410                 415
Ala Ala Ala Ala Gly Pro Gly Gly Tyr Gly Pro Gly Gln Gly Pro
            420                 425                 430
Gly Gln Gln Gly Pro Gly Gln Gly Pro Ser Pro Gly Ala Ala Ala
            435                 440                 445
Ala Ala Ala Ala Gly Pro Tyr Gln Gln Gly Pro Gly Gly Gln Gly Pro
    450                 455                 460
Tyr Gly Pro Gly Gln Gln Pro Gly Ala Ala Ala Ala Ala Ala Gly
465                 470                 475                 480
Pro Tyr Gln Gln Gly Pro Gly Gln Gly Pro Tyr Gly Pro Gly Gln
                485                 490                 495
Gln Pro Gly Ala Ala Ala Ala Ala Ala Gly Pro Gly Gly Tyr Gly
            500                 505                 510
Pro Gly Gly Gln Gly Pro Ser Pro Gly Ala Ala Ala Ala Ala Ala
        515                 520                 525
Gly Pro Gly Gly Tyr Gly Pro Gly Gln Gly Pro Ser Pro Gly Ala
    530                 535                 540
Ala Ala Ala Ala Ala Gly Pro Gly Gln Gln Gly Pro Tyr Pro Gly
545                 550                 555                 560
Ala Ala Ala Ala Ala Ala Gly Pro Gly Gln Gln Gly Pro Tyr Pro
                565                 570                 575
Gly Ala Ala Ala Ala Ala Ala Gly Pro Gly Pro Gly Ala Ala Ala
            580                 585                 590
Ala Ala Ala Ala Gly Pro Gly Pro Gly
            595                 600

<210> SEQ ID NO 26
<211> LENGTH: 16
<212> TYPE: PRT
<213> ORGANISM: Artificial Sequence
<220> FEATURE:
<223> OTHER INFORMATION: HisTag(SL)

<400> SEQUENCE: 26

Met His His His His His His His His His Ser Ser Gly Ser Ser
1               5                   10                  15

<210> SEQ ID NO 27
<211> LENGTH: 11
<212> TYPE: PRT
<213> ORGANISM: Artificial Sequence
<220> FEATURE:
<223> OTHER INFORMATION: HRV3C protease recognition site

<400> SEQUENCE: 27

Leu Gln Val Leu Phe Gln Gly Pro Ala Arg Ala
1               5                   10
```

```
<210> SEQ ID NO 28
<211> LENGTH: 590
<212> TYPE: PRT
<213> ORGANISM: Artificial Sequence
<220> FEATURE:
<223> OTHER INFORMATION: Met-PRT1171

<400> SEQUENCE: 28

Met Gly Pro Gly Gly Gln Gly Pro Tyr Gly Pro Gly Ala Ser Ala Ala
1               5                   10                  15

Ala Ala Ala Ala Ala Gly Pro Tyr Gly Tyr Gly Pro Gly Gly Gln Gly
                20                  25                  30

Pro Gly Gln Gln Gly Pro Tyr Gln Gln Gly Pro Gly Gln Gln Ser Gly
            35                  40                  45

Gly Asn Gly Pro Gly Gln Gln Gly Gly Tyr Gly Pro Gly Gln Gln Gly
50                  55                  60

Pro Gly Ala Ala Ala Ala Ala Ala Gly Pro Tyr Gly Tyr Gly Pro
65                  70                  75                  80

Gly Gly Gln Gly Pro Gly Gln Gln Gly Pro Tyr Gln Gln Gly Pro Gly
                85                  90                  95

Gln Gln Ser Gly Gly Asn Gly Pro Gly Gln Gln Gly Gly Tyr Gly Pro
            100                 105                 110

Gly Gln Gln Gly Pro Gly Ala Ala Ala Ala Ala Ala Gly Pro Tyr
            115                 120                 125

Gly Tyr Gly Pro Gly Gly Gln Gly Pro Tyr Gln Gln Gly Pro Gly Gln
            130                 135                 140

Gln Ser Gly Gly Asn Gly Pro Gly Gln Gln Gly Gly Tyr Gly Pro Gly
145                 150                 155                 160

Gln Gln Gly Pro Gly Ala Ala Ala Ala Ala Ala Gly Pro Tyr Gly
                165                 170                 175

Tyr Gly Pro Gly Gly Gln Gly Pro Tyr Gln Gln Gly Pro Gly Gln Gln
                180                 185                 190

Ser Gly Gly Asn Gly Pro Gly Gln Gln Gly Gly Tyr Gly Pro Gly Gln
            195                 200                 205

Gln Gly Pro Gly Ala Ala Ala Ala Ala Ala Gly Pro Tyr Gly Pro
210                 215                 220

Gly Gln Gln Gly Pro Tyr Gln Gln Gly Pro Gly Gln Gln Gly Asn Gly
225                 230                 235                 240

Gln Gln Gly Pro Gly Gln Gln Gly Pro Gly Gln Pro Gly Ala Ala
                245                 250                 255

Ala Ala Ala Ala Ala Gly Pro Tyr Gly Pro Gly Gln Gln Gly Pro Tyr
                260                 265                 270

Gln Gln Gly Pro Gly Gln Gln Gly Asn Gly Gln Gln Gly Pro Gly Gln
                275                 280                 285

Gln Gly Pro Gly Gln Gln Pro Gly Ala Ala Ala Ala Ala Gly
            290                 295                 300

Pro Tyr Gly Pro Gly Gln Gln Gly Pro Tyr Gln Gln Gly Pro Gly Gln
305                 310                 315                 320

Gln Gly Pro Gly Gln Gln Gly Pro Gly Gln Gln Pro Gly Ala Ala Ala
                325                 330                 335

Ala Ala Ala Ala Gly Pro Tyr Gly Pro Gly Gln Gln Gly Pro Tyr Gln
            340                 345                 350

Gln Gly Pro Gly Gln Gln Gly Pro Gly Gln Gln Gly Pro Gly Gln Gln
            355                 360                 365
```

```
Pro Gly Ala Ala Ala Ala Ala Ala Gly Pro Gly Gly Tyr Gly Pro
    370             375             380
Gly Gly Gln Gly Pro Gly Gln Gln Gly Pro Gly Gln Gln Gly Pro Ser
385             390             395             400
Pro Gly Ala Ala Ala Ala Ala Ala Gly Pro Gly Gly Tyr Gly Pro
            405             410             415
Gly Gly Gln Gly Pro Gly Gln Gln Gly Pro Gly Gln Gln Gly Pro Ser
            420             425             430
Pro Gly Ala Ala Ala Ala Ala Ala Gly Pro Tyr Gln Gln Gly Pro
            435             440             445
Gly Gly Gln Gly Pro Tyr Gly Pro Gly Gln Gln Pro Gly Ala Ala Ala
    450             455             460
Ala Ala Ala Ala Gly Pro Tyr Gln Gln Gly Pro Gly Gly Gln Gly Pro
465             470             475             480
Tyr Gly Pro Gly Gln Gln Pro Gly Ala Ala Ala Ala Ala Ala Gly
            485             490             495
Pro Gly Gly Tyr Gly Pro Gly Gly Gln Gly Pro Ser Pro Gly Ala Ala
            500             505             510
Ala Ala Ala Ala Ala Gly Pro Gly Gly Tyr Gly Pro Gly Gly Gln Gly
            515             520             525
Pro Ser Pro Gly Ala Ala Ala Ala Ala Ala Gly Pro Gly Gln Gln
    530             535             540
Gly Pro Tyr Pro Gly Ala Ala Ala Ala Ala Ala Gly Pro Gly Gln
545             550             555             560
Gln Gly Pro Tyr Pro Gly Ala Ala Ala Ala Ala Ala Gly Pro Gly
            565             570             575
Pro Gly Ala Ala Ala Ala Ala Ala Gly Pro Gly Pro Gly
            580             585             590
```

MODIFIED FIBROIN

RELATED PATENT APPLICATIONS

This application is based on and claims the benefit of priority from International Application No. PCT/JP2020/000535, filed on Jan. 9, 2020, which claims priority to Japanese Patent Application No. 2019-001812, filed on Jan. 9, 2019, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 6, 2021, is named "051723-0562164_SequenceListing.txt" and is 121 KB in size.

TECHNICAL FIELD

The present invention relates to a modified fibroin. More specifically, the present invention relates to a modified fibroin with a reduced content of serine residue.

BACKGROUND ART

Fibroin is a type of fibrous protein. Fibroin contains an amino acid residue having a small side chain, such as a glycine residue, an alanine residue, a serine residue, or a tyrosine residue at a high ratio of 90%. Proteins (silk proteins, hornet silk proteins, and spider silk proteins) and the like constituting the yarn produced by insects and spiders are known as fibroin.

Silk proteins have excellent mechanical properties, hygroscopic properties, and deodorizing properties, and are widely used as raw materials for garments. In addition, the silk yarn is an immuno-tolerant natural fiber, has high biocompatibility, and is therefore also used for surgical sutures.

Recombinant spider silk proteins and recombinant silk proteins are produced in several heterologous protein production systems. For example, many cases of production of a recombinant fibroin by a recombinant protein production system using goat, silkworm, plant, mammalian cell, yeast, mold, gram-negative bacterium, and gram-positive bacterium as a host have been reported, and certain outcomes have been obtained (Non Patent Literature 1 and Patent Literatures 1 and 2).

Various compositions each containing a modified fibroin are also produced. For example, a protein fiber is known as an example of the composition containing a modified fibroin. As a method for producing a protein fiber, a "wet spinning method and a dry-wet spinning method are known in which a spinning stock solution discharged from a nozzle is coagulated in a coagulation bath liquid to form a fiber. As a method for producing a protein fiber by a wet spinning method, a dry-wet spinning method, or the like, it is known that a protein solution in which a protein is dissolved in a solvent is used as a doping liquid (spinning stock solution), the doping liquid is extruded from a spinneret into a coagulation liquid in a desolvation tank, the solvent is desorbed from the doping liquid, and a fiber is formed into an undrawn yarn to obtain a protein fiber (see, for example, Patent Literature 3).

CITATION LIST

Patent Literature

Patent Literature 1: Japanese Unexamined Patent Publication No. 2014-502140
Patent Literature 2: International Patent Publication No. WO2015/042164
Patent Literature 3: International Patent Publication No. WO2013/065651

Non Patent Literature

Non Patent Literature 1: Science, 2002, Vol. 295, pp. 472-476

SUMMARY OF INVENTION

Technical Problem

In production of a protein fiber, formic acid may be used as a solvent of a doping liquid and/or an additive of a coagulation bath liquid. The present inventors have found that a protein fiber produced using formic acid generates an odor disadvantageously when the protein fiber is left in the air. The present inventors have also found that in a protein fiber produced using a carboxylic acid such as formic acid as a solvent of a doping liquid and/or an additive of a coagulation bath liquid, an ester group is formed by a dehydration condensation reaction between a hydroxy group in a protein and a carboxylic acid in a spinning process. In the protein fiber thus obtained, hydrolysis of an ester group added to the protein may proceed using a carboxylic acid such as formic acid remaining in a trace amount on a surface of the protein or inside the protein as a catalyst, and the carboxylic acid may be released. The released carboxylic acid may generate an odor or the like. The present invention is to solve such a problem newly found by the present inventors.

That is, an object of the present invention is to provide a modified fibroin in which formation of an ester bond by contact with a carboxylic acid such as formic acid is reduced.

Solution to Problem

The present inventors have found that the above object can be achieved by reducing the content of serine residue in an amino acid sequence of a modified fibroin. The present invention is based on this finding.

The present invention relates to, for example, each of the following inventions.

[1] A modified fibroin including a domain sequence represented by Formula 1: [(A)$_n$ motif-REP]$_m$ or Formula 2: [(A)$_n$ motif-REP]$_m$-(A)$_n$ motif, in which
a serine residue content rate is less than 5.5%.
[In Formula 1 and Formula 2, the (A)$_n$ motif represents an amino acid sequence consisting of 4 to 27 amino acid residues, and the number of alanine residues with respect to the total number of amino acid residues in the (A)$_n$ motif is 80% or more. REP represents an amino acid sequence consisting of 10 to 200 amino acid residues. m represents an integer of 10 to 300. The plurality of (A)$_n$ motifs may be the same amino acid sequence or different amino acid sequences. A plurality of REPs may be the same amino acid sequence or different amino acid sequences.]

[2] The modified fibroin according to aspect [1], in which a threonine residue content rate is 9% or less.

[3] The modified fibroin according to aspect [1] or [2], in which a content rate of serine residue and threonine residue is 9% or less.

[4] A modified fibroin including: an amino acid sequence set forth in SEQ ID NO: 2, SEQ ID NO: 3, SEQ ID NO: 4, SEQ ID NO: 5, or SEQ ID NO: 28; or an amino acid sequence having 90% or more sequence identity with the amino acid sequence set forth in SEQ ID NO: 2, SEQ ID NO: 3, SEQ ID NO: 4, SEQ ID NO: 5, or SEQ ID NO: 28.

[5] The modified fibroin according to any one of aspects [1] to [4], further including a tag sequence at either or both of an N-terminal and a C-terminal.

[6] The modified fibroin according to aspect [5], in which the tag sequence includes an amino acid sequence set forth in SEQ ID NO: 17 or SEQ ID NO: 18.

[7] A modified fibroin including: an amino acid sequence set forth in SEQ ID NO: 10, SEQ ID NO: 11, SEQ ID NO: 12, SEQ ID NO: 13, or SEQ ID NO: 25; or an amino acid sequence having 90% or more sequence identity with the amino acid sequence set forth in SEQ ID NO: 10, SEQ ID NO: 11, SEQ ID NO: 12, SEQ ID NO: 13, or SEQ ID NO: 25.

[8] A nucleic acid that encoding the modified fibroin according to any one of aspects [1] to [7].

[9] A nucleic acid hybridizing with a complementary strand of the nucleic acid according to aspect [8] under stringent conditions and encoding a modified fibroin including a domain sequence represented by Formula 1: $[(A)_n$ motif-REP$]_m$ or Formula 2: $[(A)_n$ motif-REP$]_m$-$(A)_n$ motif. [In Formula 1 and Formula 2, the $(A)_n$ motif represents an amino acid sequence consisting of 4 to 27 amino acid residues, and the number of alanine residues with respect to the total number of amino acid residues in the $(A)_n$ motif is 80% or more. REP represents an amino acid sequence consisting of 10 to 200 amino acid residues. m represents an integer of 10 to 300. The plurality of $(A)_n$ motifs may be the same amino acid sequence or different amino acid sequences. A plurality of REPs may be the same amino acid sequence or different amino acid sequences.]

[10] A nucleic acid having 90% or more sequence identity with the nucleic acid according to aspect [8] and encoding a modified fibroin including a domain sequence represented by Formula 1: $[(A)_n$ motif-REP$]_m$ or Formula 2: $[(A)_n$ motif-REP$]_m$-$(A)_n$ motif. [In Formula 1 and Formula 2, the $(A)_n$ motif represents an amino acid sequence consisting of 4 to 27 amino acid residues, and the number of alanine residues with respect to the total number of amino acid residues in the $(A)_n$ motif is 80% or more. REP represents an amino acid sequence consisting of 10 to 200 amino acid residues. m represents an integer of 10 to 300. The plurality of $(A)_n$ motifs may be the same amino acid sequence or different amino acid sequences. A plurality of REPs may be the same amino acid sequence or different amino acid sequences.]

[11] An expression vector having: the nucleic acid sequence according to any one of aspects [8] to [10]; and one or a plurality of regulatory sequences operably linked to the nucleic acid sequence according to any one of aspects [8] to [10].

[12] The expression vector according to aspect [11], which is a plasmid vector or a viral vector.

[13] A host transformed with the expression vector according to aspect [11] or [12].

[14] The host according to aspect [13], which is a prokaryote.

[15] The host according to aspect [14], in which the prokaryote is a microorganism belonging to a genus selected from the group consisting of *Escherichia*, *Brevibacillus*, *Serratia*, *Bacillus*, *Microbacterium*, *Brevibacterium*, *Corynebacterium*, and *Pseudomonas*.

[16] The host according to aspect [13], which is a eukaryote.

[17] The host according to aspect [16], in which the eukaryote is a yeast, a filamentous fungus, or an insect cell.

[18] An artificially modified fibroin composition containing the modified fibroin according to any one of aspects [1] to [7].

[19] The artificially modified fibroin composition according to aspect [18], which is a protein powder.

[20] The artificially modified fibroin composition according to aspect [18], which is a doping liquid.

[21] The artificially modified fibroin composition according to aspect [18], which is a fiber.

[22] The artificially modified fibroin composition according to aspect [18], which is a film.

[23] A method for producing a modified fibroin, the method including a step in which a host transformed with an expression vector having a nucleic acid sequence encoding a modified fibroin and one or a plurality of regulatory sequences operably linked to the nucleic acid sequence expresses the nucleic acid, in which
the modified fibroin is the modified fibroin according to any one of aspects [1] to [7].

[24] A method for producing an artificially modified fibroin composition containing a modified fibroin, the method including a step of preparing a modified fibroin, in which the modified fibroin is the modified fibroin according to any one of aspects [1] to [7].

[25] The production method according to aspect [23] or [24], further including a step of bringing the modified fibroin into contact with a carboxylic acid.

[26] The production method according to aspect [24], further including a step of adjusting a modified fibroin solution containing the modified fibroin and a carboxylic acid.

[27] A product including the modified fibroin according to any one of aspects [1] to [7],
the product being selected from the group consisting of a fiber, a yarn, a film, a foam, a grain, a nanofibril, a gel, and a resin.

Advantageous Effects of Invention

The present invention can provide a modified fibroin in which formation of an ester bond by contact with a carboxylic acid such as formic acid is reduced.

BRIEF DESCRIPTION OF DRAWINGS

FIG. 2 is a graph illustrating measurement results of an infrared absorption spectrum of a protein fiber formed of a modified fibroin.

DESCRIPTION OF EMBODIMENTS

Figure 1:
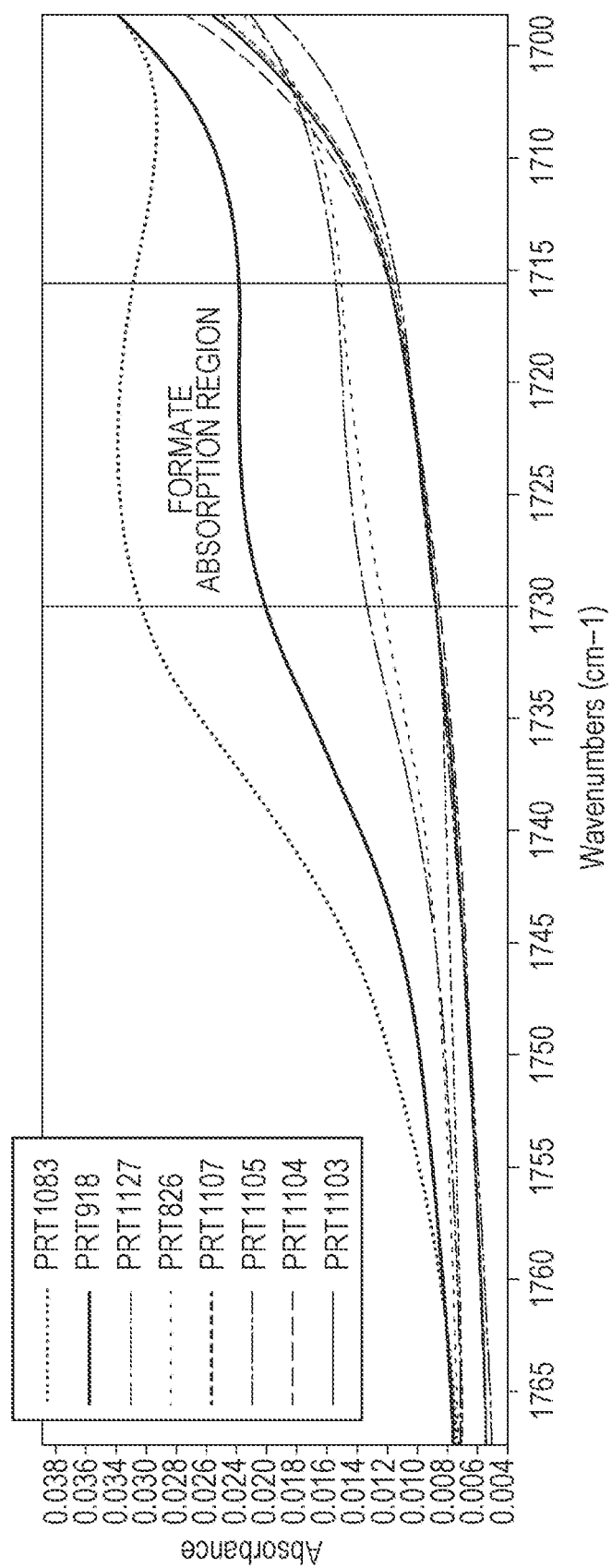
FIG. 1 is a graph illustrating measurement results of an infrared absorption spectrum of a film formed of a modified fibroin.

Hereinafter, embodiments for carrying out the present invention will be described in detail. However, the present invention is not limited to the Following Embodiments.

[Modified Fibroin]

The modified fibroin according to the present invention is a protein including a domain sequence represented by Formula 1: $[(A)_n \text{ motif-REP}]_m$ or Formula 2: $[(A)_n \text{ motif-REP}]_m\text{-}(A)_n$ motif. In the modified fibroin, an amino acid sequence (N-terminal sequence and C-terminal sequence) may be further added to either or both of the N-terminal side and the C-terminal side of the domain sequence. The N-terminal sequence and the C-terminal sequence, although not limited thereto, are typically regions that do not have repetitions of amino acid motifs characteristic of fibroin and consist of amino acids of about 100 residues.

The term "modified fibroin" as used herein means a fibroin whose amino acid sequence is different from the amino acid sequence of a naturally occurring fibroin. The term "naturally occurring fibroin" as used herein means a fibroin whose amino acid sequence is the same as that of a fibroin produced by insects, spiders, or the like which naturally exist. The naturally occurring fibroin is also a protein including a domain sequence represented by Formula 1: $[(A)_n \text{ motif-REP}]_m$ or Formula 2: $[(A)_n \text{ motif-REP}]_m\text{-}(A)_n$ motif.

Examples of the naturally occurring fibroin include a fibroin produced by insects or spiders.

Examples of the fibroin produced by insects include silk proteins produced by silkworms such as *Bombyx mori, Bombyx mandarina, Antheraea yamamai, Anteraea pernyi, Eriogyna pyretorum, Pilosamia Cynthia ricini, Samia cynthia, Caligura japonica, Antheraea mylitta,* and *Antheraea assama*; and hornet silk proteins discharged by larvae of *Vespa simillima xanthoptera*.

A more specific example of the fibroin produced by insects includes a silkworm fibroin L chain (GenBank Accession No. M76430 (base sequence), AAA27840.1 (amino acid sequence)).

Examples of the fibroin produced by spiders include spider silk proteins produced by spiders belonging to the genus *Araneus* such as *Araneus ventricosus, Araneus diadematus, Araneus pinguis, Araneus pentagrammicus* and *Araneus nojimai*, spiders belonging to the genus *Neoscona* such as *Neoscona scylla, Neoscona nautica, Neoscona adianta* and *Neoscona scylloides*, spiders belonging to the genus *Pronus* such as *Pronous minutes*, spiders belonging to the genus *Cyrtarachne* such as *Cyrtarachne bufo* and *Cyrtarachne inaequalis*, spiders belonging to the genus *Gasteracantha* such as *Gasteracantha kuhli* and *Gasteracantha mammosa*, spiders belonging to the genus *Ordgarius* such as *Ordgarius hobsoni* and *Ordgarius sexspinosus*, spiders belonging to the genus *Argiope* such as *Argiope amoena, Argiope minuta* and *Argiope bruennich*, spiders belonging to the genus *Arachnura* such as *Arachnura logio*, spiders belonging to the genus *Acusilas* such as *Acusilas coccineus*, spiders belonging to the genus *Cytophora* such as *Cyrtophora moluccensis, Cyrtophora exanthematica* and *Cyrtophora unicolor*, spiders belonging to the genus *Poltys* such as *Poltys illepidus*, spiders belonging to the genus *Cyclosa* such as *Cyclosa octotuberculata, Cyclosa sedeculata, Cyclosa vallata* and *Cyclosa atrata*, and spiders belonging to the genus *Chorizopes* such as *Chorizopes nipponicus*; and spider silk proteins produced by spiders belonging to the genus *Tetragnatha* such as *Tetragnatha praedonia, Tetragnatha maxillosa, Tetragnatha extensa* and *Tetragnatha squamata*, spiders belonging to the genus *Leucauge* such as *Leucauge magnifica, Leucauge blanda* and *Leucauge subblanda*, spiders belonging to the genus *Nephila* such as *Nephila clavata* and *Nephila pilipes*, spiders belonging to the genus *Menosira* such as *Menosira ornata*, spiders belonging to the genus *Dyschiriognatha* such as *Dyschiriognatha tenera*, spiders belonging to the genus *Latrodectus* such as *Latrodectus mactans, Latrodectus hasseltii, Latrodectus geometricus* and *Latrodectus tredecimguttatus*, and spiders belonging to the family Tetragnathidae such as spiders belonging to the genus *Euprosthenops*. Examples of spider silk proteins include traction yarn proteins such as MaSp (MaSp1 and MaSp2) and ADF (ADF3 and ADF4), and MiSp (MiSp1 and MiSp2).

More specific examples of the fibroin produced by spiders include fibroin-3 (adf-3) [derived from *Araneus diadematus*] (GenBank Accession Number AAC47010 (amino acid sequence), U47855 (base sequence)), fibroin-4 (adf-4) [derived from *Araneus diadematus*] (GenBank Accession Number AAC47011 (amino acid sequence), U47856 (base sequence)), dragline silk protein spidroin 1 [derived from *Nephila clavipes*] (Gen Bank Accession Number AAC04504 (amino acid sequence), U37520 (base sequence)), major angullate spidroin 1 [derived from *Latrodectus hesperus*] (GenBank Accession Number ABR68856 (amino acid sequence), EF595246 (base sequence)), dragline silk protein spidroin 2 [derived from *Nephila clavata*] (GenBank Accession Number AAL32472 (amino acid sequence), AF441245 (base sequence)), major anpullate spidroin 1 [derived from *Euprosthenops australis*] (GenBank Accession Number CAJ00428 (amino acid sequence), AJ973155 (base sequence)) and major ampullate spidroin 2 [*Euprosthenops australis*] (GenBank Accession Number CAM32249.1 (amino acid sequence), AM490169 (base sequence)), minor ampullate silk protein 1 [*Nephila clavipes*] (GenBank Accession Number AAC14589.1 (amino acid sequence), minor ampullate silk protein 2 [*Nephila clavipes*] (GenBank Accession Number AAC14591.1 (amino acid sequence)), and minor ampullate spidroin-like protein [*Nephilengys cruentata*] (GenBank Accession Number ABR37278.1 (amino acid sequence)).

As a further specified example of the naturally occurring fibroin, fibroin whose sequence information is registered in NCBI GenBank may be mentioned. For example, sequences thereof may be confirmed by extracting sequences in which spidroin, ampullate, fibroin, "silk and polypeptide", or "silk and protein" is described as a keyword in DEFINITION among sequences containing INV as DIVISION among sequence information registered in NCBI GenBank, sequences in which a specific character string of products is described from CDS, or sequences in which a specific character string is described from SOURCE to TISSUE TYPE.

The "modified fibroin" may be a fibroin whose amino acid sequence has been modified based on a naturally occurring fibroin (for example, a fibroin whose amino acid sequence has been modified by altering a cloned gene sequence of naturally occurring fibroin) or a fibroin obtained by artificially designing an amino acid sequence independently of a naturally occurring fibroin (for example, a fibroin having a desired amino acid sequence by chemically synthesizing a nucleic acid encoding the designed amino acid sequence), as long as it has the amino acid sequence specified in the present invention.

The term "domain sequence" as used herein refers to an amino acid sequence which produces a crystalline region (typically, equivalent to $(A)_n$ motif of an amino acid sequence) and an amorphous region (typically, equivalent to REP of an amino acid sequence) peculiar to fibroin and means an amino acid sequence represented by Formula 1: $[(A)_n \text{ motif-REP}]_m$ or Formula 2: $[(A)_n \text{ motif-REP}]_m\text{-}(A)_n$ motif. Here, the $(A)_n$ motif represents an amino acid sequence consisting of 4 to 27 amino acid residues, and the number of alanine residues with respect to the total number of amino acid residues in the (A)$_n$ motif is 80% or more. REP represents an amino acid sequence consisting of 10 to 200 amino acid residues. m represents an integer of 10 to 300. m is preferably an integer of 20 to 300, and more preferably an integer of 30 to 300. The plurality of (A)$_n$ motifs may be the same amino acid sequence or different amino acid sequences. The plurality of REPs may be the same amino acid sequence or different amino acid sequences.

The (A)$_n$ motif may be such that the number of alanine residues is 80% or more with respect to the total number of amino acid residues in the (A)$_n$ motif, but it is preferably 85% or more, more preferably 90% or more, still more preferably 95% or more, and even still more preferably 100% (which means that the (A)$_n$ motif consists of only alanine residues). It is preferable that at least seven of the plurality of (A)$_n$ motifs in the domain sequence consist of only alanine residues. The phrase "consist of only alanine residues" means that the (A)$_n$ motif has an amino acid sequence represented by (Ala)$_k$ (where Ala represents an alanine residue, and k represents an integer of 4 to 27, preferably an integer of 4 to 20, and more preferably an integer of 4 to 16).

The modified fibroin according to the present embodiment has an amino acid sequence having a reduced content of serine residue. In the modified fibroin according to the present embodiment, the content of serine residue is reduced, and therefore formation of an ester bond by contact with a carboxylic acid such as formic acid is reduced. As a result, an odor is less likely to be generated even when the modified fibroin according to the present embodiment is left in the air.

The serine residue content rate in the modified fibroin according to the present embodiment is preferably 9% or less, preferably less than 8.5%, preferably 8% or less, preferably less than 7.5%, preferably 7% or less, preferably less than 6.5%, preferably 6% or less, preferably less than 5.5%, preferably 5% or less, preferably less than 4.5%, preferably 4% or less, preferably less than 3.5%, preferably 3% or less, preferably less than 2.5%, preferably 2% or less, preferably less than 1.5%, preferably 1% or less, preferably less than 0.5%, and particularly preferably 0%. When the serine residue content rate is within this range, the effect of the present invention can be more remarkably exhibited.

Herein, the "serine residue content rate" is a value calculated by x/y×100%, where x represents the total number of serine residues and y represents the total number of amino acid residues in a fibroin including a domain sequence represented by Formula 1: [(A)$_n$ motif-REP]$_m$ or Formula 2: [(A)$_n$ motif-REP]$_m$-(A)$_n$ motif.

Furthermore, the threonine residue content rate in the modified fibroin according to the present embodiment is preferably 9% or less, preferably less than 8.5%, preferably 8% or less, preferably less than 7.5%, preferably 7% or less, preferably less than 6.5%, preferably 6% or less, preferably less than 5.5%, preferably 5% or less, preferably less than 4.5%, preferably 4% or less, preferably less than 3.5%, preferably 3% or less, preferably less than 2.5%, preferably 2% or less, preferably less than 1.5%, preferably 1% or less, preferably less than 0.5%, and particularly preferably 0%. When the threonine residue content rate is within this range, the effect of the present invention can be more remarkably exhibited.

Herein, the "threonine residue content rate" is a value calculated by z/y×100%, where z represents the total number of threonine residues and y represents the total number of amino acid residues in a fibroin including a domain sequence represented by Formula 1: [(A)$_n$ motif-REP]$_m$ or Formula 2: [(A)$_n$ motif-REP]$_m$-(A)$_n$ motif.

The content rate of serine residue and threonine residue in the modified fibroin according to the present embodiment is preferably 9% or less, preferably less than 8.5%, preferably 8% or less, preferably less than 7.5%, preferably 7% or less, preferably less than 6.5%, preferably 6% or less, preferably less than 5.5%, preferably 5% or less, preferably less than 4.5%, preferably 4% or less, preferably less than 3.5%, preferably 3% or less, preferably less than 2.5%, preferably 2% or less, preferably less than 1.5%, preferably 1% or less, preferably less than 0.5%, and particularly preferably 0%. When the content rate of serine residue and threonine residue is within this range, the effect of the present invention can be more remarkably exhibited.

Herein, the "serine residue and threonine residue" is a value calculated by (x+z)/y×100%, where z represents the total number of serine residues, z represents the total number of threonine residues, and y represents the total number of amino acid residues in a fibroin including a domain sequence represented by Formula 1: [(A)$_n$ motif-REP]$_m$ or Formula 2: [(A)$_n$ Motif-REP]$_m$-(A)$_n$ motif.

The molecular weight of the modified fibroin according to the present invention is not particularly limited, and may be, for example, 10 kDa or more and 700 kDa or less. The molecular weight of the modified fibroin according to the present invention may be, for example, 20 kDa or more, 30 kDa or more, 40 kDa or more, 50 kDa or more, 60 kDa or more, 70 kDa or more, 80 kDa or more, 90 kDa or more, or 100 kDa or more, and may be 600 kDa or less, 500 kDa or less, 400 kDa or less, 300 kDa or less, or 200 kDa or less.

A more specific example of the modified fibroin according to the present invention may be a modified fibroin including (i) an amino acid sequence set forth in SEQ ID NO: 2, SEQ ID NO: 3, SEQ ID NO: 4, SEQ ID NO: 5, or SEQ ID NO: 28, or a modified fibroin including (ii) an amino acid sequence having 90% or more sequence identity with the amino acid sequence set forth in SEQ ID NO: 2, SEQ ID NO: 3, SEQ ID NO: 4, SEQ ID NO: 5, or SEQ ID NO: 28.

The amino acid sequence set forth in SEQ ID NO: 2 (Met-PRT1104) is obtained by substituting most of serine residues (S) of the amino acid sequence set forth in SEQ ID NO: 19 (Met-PRT410) with alanine residues (A) or glycine residues (G). The amino acid sequence set forth in SEQ ID NO: 19 is obtained by deleting one of every two (A)$_n$ motifs from the N-terminal side to the C-terminal side in the amino acid sequence set forth in SEQ ID NO: 20 (Met-PRT380) and further inserting one [(A)$_n$ motif-REP] just before the C-terminal sequence. The amino acid sequence set forth in SEQ ID NO: 20 is obtained by substituting all GGXs in REP of the amino acid sequence set forth in SEQ ID NO: 21 (Met-PRT313) equivalent to a naturally occurring fibroin with GQXs.

The amino acid sequence set forth in SEQ ID NO: 3 (Met-PRT1105) is obtained by substituting a serine residue (S) of the amino acid sequence set forth in SEQ ID NO: 1 (Met-PRT918) with an alanine residue (A) or a glycine residue (G). The amino acid sequence set forth in SEQ ID NO: 1 is obtained by substituting all QQs in the amino acid sequence set forth in SEQ ID NO: 19 with VFs and substituting the remaining Qs with Is.

The amino acid sequence set forth in SEQ ID NO: 4 (Met-PRT1103) is obtained by substituting a tyrosine residue (Y) of the amino acid sequence set forth in SEQ ID NO:

19 with a phenylalanine residue (F) and substituting most of serine residues (S) with alanine residues (A) or glycine residues (G).

The amino acid sequence set forth in SEQ ID NO: 5 (Met-PRT1107) is obtained by substituting a serine residue (S) of the amino acid sequence set forth in SEQ ID NO: 1 with an alanine residue (A), a valine residue (V), a leucine residue (L), or an isoleucine residue (I).

The amino acid sequence set forth in SEQ ID NO: 28 (Met-PRT1171) has an amino acid sequence in which the number of amino acid residues of an $(A)_n$ motif is unified to 7 and REP (non-crystalline region) is shortened toward the C-terminal in the amino acid sequence including a unit of an amino acid sequence represented by Formula 1: $[(A)_n$ motif-REP$]_m$.

The modified fibroin of (i) may consist of the amino acid sequence set forth in SEQ ID NO: 2, SEQ ID NO: 3, SEQ ID NO: 4, SEQ ID NO: 5, or SEQ ID NO: 28.

The modified fibroin of (ii) includes an amino acid sequence having 90% or more sequence identity with the amino acid sequence set forth in SEQ ID NO: 2, SEQ ID NO: 3, SEQ ID NO: 4, SEQ ID NO: 5, or SEQ ID NO: 28. The modified fibroin of (ii) is also a protein including a domain sequence represented by Formula 1: $[(A)_n$ motif-REP$]_m$ or Formula 2: $[(A)_n$ motif-REP$]_m$-$(A)_n$ motif. The sequence identity is preferably 95% or more.

The modified fibroin of (ii) preferably has a serine residue content rate of less than 5.5%. The modified fibroin of (ii) preferably has a threonine residue content rate of 9% or less. Furthermore, the modified fibroin of (ii) preferably has a content rate of serine residue and threonine residue of 9% or less.

The above-described modified fibroin may include a tag sequence at either or both of the N-terminal and C-terminal. This makes it possible to isolate, immobilize, detect, and visualize the modified fibroin.

The tag sequence may be, for example, an affinity tag utilizing specific affinity (binding property, affinity) with another molecule. As a specific example of the affinity tag, a histidine tag (His tag) can be mentioned. The His tag is a short peptide in which about 4 to 10 histidine residues are arranged and has a property of specifically binding to a metal ion such as nickel, so it can be used for isolation of modified fibroin by chelating metal chromatography. A specific example of the tag sequence may be an amino acid sequence set forth in SEQ ID NO: 17 or SEQ ID NO: 18 (amino acid sequence including a His tag).

In addition, a tag sequence such as glutathione-S-transferase (GST) that specifically binds to glutathione or a maltose binding protein (MBP) that specifically binds to maltose can also be used.

Further, an "epitope tag" utilizing an antigen-antibody reaction can also be used. By adding a peptide (epitope) illustrating antigenicity as a tag sequence, an antibody against the epitope can be bound. Examples of the epitope tag include an HA (peptide sequence of hemagglutinin of influenza virus) tag, a myc tag, and a FLAG tag. The modified fibroin can easily be purified with high specificity by utilizing an epitope tag.

It is also possible to use a tag sequence which can be cleaved with a specific protease. By treating a protein adsorbed through the tag sequence with protease, it is also possible to recover the modified fibroin cleaved from the tag sequence.

A more specific example of the modified fibroin including a tag sequence may be a modified fibroin including (iii) an amino acid sequence set forth in SEQ ID NO: 10, SEQ ID NO: 11, SEQ ID NO: 12, SEQ ID NO: 13, or SEQ ID NO: 25, or a modified fibroin including an amino acid sequence having 90% or more sequence identity with the amino acid sequence set forth in SEQ ID NO: 10, SEQ ID NO: 11, SEQ ID NO: 12, SEQ ID NO: 13, or SEQ ID NO: 25.

The amino acid sequences set forth in SEQ ID NO: 10, SEQ ID NO: 11, SEQ ID NO: 12, and SEQ ID NO: 13 respectively have amino acid sequences obtained by adding the amino acid sequence (including a His tag) set forth in SEQ ID NO: 18 to the N-terminals of the amino acid sequences set forth in SEQ ID NO: 2, SEQ ID NO: 3, SEQ ID NO: 4, and SEQ ID NO: 5. The amino acid sequence set forth in SEQ ID NO: 25 has an amino acid sequence obtained by adding the amino acid sequence (including a His tag) set forth in SEQ ID NO: 17 to the N-terminal of the amino acid sequence set forth in SEQ ID NO: 28.

The modified fibroin of (iii) may consist of the amino acid sequence set forth in SEQ ID NO: 10, SEQ ID NO: 11, SEQ ID NO: 12, SEQ ID NO: 13, or SEQ ID NO: 25.

The modified fibroin of (iii) includes an amino acid sequence having 90% or more sequence identity with the amino acid sequence set forth in SEQ ID NO: 10, SEQ ID NO: 11, SEQ ID NO: 12, SEQ ID NO: 13, or SEQ ID NO: 25. The modified fibroin of (iii) is also a protein including a domain sequence represented by Formula 1: $[(A)_n$ motif-REP$]_m$ or Formula 2: $[(A)_n$ motif-REP$]_m$-$(A)_n$ motif. The sequence identity is preferably 95% or more.

The modified fibroin of (iii) preferably has a serine residue content rate of less than 5.5%. The modified fibroin of (iii) preferably has a threonine residue content rate of 9% or less. Furthermore, the modified fibroin of (iii) preferably has a content rate of serine residue and threonine residue of 9% or less.

The above-mentioned modified fibroin may include a secretory signal for releasing the protein produced in the recombinant protein production system to the outside of a host. The sequence of the secretory signal can be appropriately set depending on the type of the host.

[Nucleic Acid]

The nucleic acid according to the present invention encodes the modified fibroin according to the present invention. Specific examples of the nucleic acid include nucleic acids encoding a modified fibroin including an amino acid sequence set forth in SEQ ID NO: 2, SEQ ID NO: 3, SEQ ID NO: 4, SEQ ID NO: 5, or SEQ ID NO: 28, or a modified fibroin or the like having an amino acid sequence (tag sequence) set forth in SEQ ID NO: 17 or SEQ ID NO: 18 attached to either or both of the N-terminal and C-terminal of each of these amino acid sequences.

The nucleic acid according to one embodiment is a nucleic acid hybridizing with a complementary strand of the nucleic acid encoding the modified fibroin according to the present invention under stringent conditions and encoding a modified fibroin including a domain sequence represented by Formula 1: $[(A)_n$ motif-REP$]_m$, or Formula 2: $[(A)_n$ motif-REP$]_m$-$(A)_n$ motif. The modified fibroin encoded by the nucleic acid preferably has a serine residue content rate of less than 5.5%. The modified fibroin encoded by the nucleic acid preferably has a threonine residue content rate of 9% or less. Furthermore, the modified fibroin encoded by the nucleic acid preferably has a content rate of serine residue and threonine residue of 9% or less.

The term "stringent conditions" refers to conditions under which a so-called specific hybrid is formed and a non-specific hybrid is not formed. The "stringent conditions" may be any of low stringent conditions, moderately stringent conditions and highly stringent conditions. The low stringent conditions mean that hybridization occurs only in the case where there is at least 85% or more identity between the sequences, and include, for example, conditions of hybridization at 42° C. using 5×SSC containing 0.5% SDS. The moderately stringent conditions mean that hybridization occurs only in the case where there is at least 90% or more identity between the sequences, and include, for example, conditions of hybridization at 50° C. using 5×SSC containing 0.5% SDS. The highly stringent conditions mean that hybridization occurs only in the case where there is at least 95% or more identity between the sequences, and include, for example, conditions of hybridization at 60° C. using 5×SSC containing 0.5% SDS.

The nucleic acid according to other embodiment is a nucleic acid having 90% or more sequence identity with the nucleic acid encoding the modified fibroin according to the present invention and encoding a modified fibroin including a domain sequence represented by Formula 1: [(A)$_n$ motif-REP]$_m$, or Formula 2: [(A)$_n$ motif-REP]$_m$-(A)$_n$ motif. The modified fibroin encoded by the nucleic acid preferably has a serine residue content rate of less than 5.5%. The modified fibroin encoded by the nucleic acid preferably has a threonine residue content rate of 9% or less. Furthermore, the modified fibroin encoded by the nucleic acid preferably has a content rate of serine residue and threonine residue of 9% or less.

[Host and Expression Vector]

An expression vector according to the present invention includes a nucleic acid sequence according to the present invention and one or a plurality of regulatory sequences operably linked thereto. The regulatory sequence is a sequence (for example, a promoter, an enhancer, a ribosome binding sequence, or a transcription termination sequence) that controls the expression of a recombinant protein in a host, and can be appropriately selected depending on the type of the host. The type of the expression vector such as a plasmid vector, a viral vector, a cosmid vector, a fosmid vector, or an artificial chromosome vector can be appropriately selected depending on the type of the host.

The host according to the present invention is a host which has been transformed with the expression vector according to the present invention. Both prokaryotes and eukaryotes such as yeast, filamentous fungi, insect cells, animal cells, and plant cells can be suitably used as hosts.

As the expression vector, an expression vector which can autonomously replicate in a host cell or can be incorporated into a chromosome of a host and which contains a promoter at a position capable of transcribing the nucleic acid according to the present invention is suitably used.

In a case where a prokaryote such as a bacterium is used as a host, the expression vector according to the present invention is preferably a vector which is capable of autonomous replication in the prokaryote and at the same time includes a promoter, a ribosome binding sequence, a nucleic acid according to the present invention and a transcription termination sequence. A gene that controls a promoter may be included.

Examples of the prokaryote include microorganisms belonging to the genus *Escherichia*, *Brevibacillus*, *Serratia*, *Bacillus*, *Microbacterium*, *Brevibacterium*, *Corynebacterium* and *Pseudomonas*.

Examples of microorganisms belonging to the genus *Escherichia* include *Escherichia coli* BL21 (Novagen, Inc.), *Escherichia coli* BL21 (DE3) (Life Technologies Corporation), *Escherichia coli* BLR (DE3) (Merck KGaA), *Escherichia coli* DH1, *Escherichia coli* G1698, *Escherichia coli* HB101, *Escherichia coli* JM109, *Escherichia coli* K5 (ATCC 23506), *Escherichia coli* KY3276, *Escherichia coli* MC1000, *Escherichia coli* MG1655 (ATCC 47076), *Escherichia coli* No. 49, *Escherichia coli* Rosetta (DE3) (Novagen, Inc.), *Escherichia coli* TB1, *Escherichia coli* Tuner (Novagen, Inc.), *Escherichia coli* Tuner (DE3) (Novagen, Inc.), *Escherichia coli* W1485, *Escherichia coli* W3110 (ATCC 27325), *Escherichia coli* XL1-Blue, and *Escherichia coli* XL2-Blue.

Examples of microorganisms belonging to the genus *Brevibacillus* include *Brevibacillus agri*, *Brevibacillus borstelensis*, *Brevibacillus centrosporus*, *Brevibacillus formosus*, *Brevibacillus invocatus*, *Brevibacillus laterosporus*, *Brevibacillus limnophilus*, *Brevibacillus parabrevis*, *Brevibacillus reuszeri*, *Brevibacillus thermoruber*, *Brevibacillus brevis* 47 (FERM BP-1223), *Brevibacillus brevis* 47K (FERM BP-2308), *Brevibacillus brevis* 47-5 (FERM BP-1664), *Brevibacillus brevis* 47-5Q (JCM 8975), *Brevibacillus choshinensis* HPD31 (FERM BP-1087), *Brevibacillus choshinensis* HPD31-S (FERM BP-6623), *Brevibacillus choshinensis* HPD31-OK (FERM BP-4573), and *Brevibacillus choshinensis* SP3 strain (manufactured by Takara Bio, Inc.).

Examples of microorganisms belonging to the genus *Serratia* include *Serratia liquefacience* ATCC 14460, *Serratia entomophila*, *Serratia ficaria*, *Serratia fonticola*, *Serratia grimesii*, *Serratia proteamaculans*, *Serratia odorifera*, *Serratia plymuthica*, and *Serratia rubidaea*.

Examples of microorganisms belonging to the genus *Bacillus* include *Bacillus subtilis* and *Bacillus amyloliquefaciens*.

Examples of microorganisms belonging to the genus *Microbacterium* include *Microbacterium ammoniaphilum* ATCC 15354.

Examples of microorganisms belonging to the genus *Brevibacterium* include *Brevibacterium divaricatum* (*Corynebacterium glutamicum*) ATCC 14020, *Brevibacterium flavum* (*Corynebacterium glutamicum* ATCC 14067) ATCC 13826, ATCC 14067, *Brevibacterium immariophilum* ATCC 14068, *Brevibacterium lactofermentum* (*Corynebacterium glutamicum* ATCC 13869) ATCC 13665, ATCC 13869, *Brevibacterium roseum* ATCC 13825, *Brevibacterium saccharolyticum* ATCC 14066, *Brevibacterium tiogenitalis* ATCC 19240, *Brevibacterium album* ATCC 15111, and *Brevibacterium cerinum* ATCC 15112.

Examples of microorganisms belonging to the genus *Corynebacterium* include *Corynebacterium ammoniagenes* ATCC 6871, ATCC 6872, *Corynebacterium glutamicum* ATCC 13032, *Corynebacterium glutamicum* ATCC 14067, *Corynebacterium acetoacidophilum* ATCC 13870, *Corynebacterium acetoglutamicum* ATCC 15806, *Corynebacterium* alkanolyticum ATCC 21511, *Corynebacterium callunae* ATCC 15991, *Corynebacterium glutamicum* ATCC 13020, ATCC 13032, ATCC 13060, *Corynebacterium lilium* ATCC 15990, *Corynebacterium melassecola* ATCC 17965, *Corynebacterium thermoaminogenes* AJ12340 (FERMBP-1539), and *Corynebacterium herculis* ATCC 13868.

Examples of microorganisms belonging to the genus *Pseudomonas* include *Pseudomonas putida*, *Pseudomonas fluorescens*, *Pseudomonas brassicacearum*, *Pseudomonas fulva*, and *Pseudomonas* sp. D-0110.

As a method for introducing an expression vector into the foregoing host cell, any method can be used as long as it introduces DNA into the host cell. Examples thereof include a method using calcium ions [Proc. Natl. Acad. Sci. USA, 69, 2110 (1972)], a protoplast method (Japanese Unexamined Patent Publication No. S63-248394), or a method described in Gene, 17, 107 (1982) or Molecular & General Genetics, 168, 111 (1979).

Transformation of microorganisms belonging to the genus *Brevibacillus* can be carried out, for example, by the method of Takahashi et al. (J. Bacteriol., 1983, 156: 1130-1134), the method of Takagi et al. (Agric. Biol. Chem., 1989, 53: 3099-3100), or the method of Okamoto et al. (Biosci. Biotechnol. Biochem., 1997, 61: 202-203).

Examples of the vector into which the nucleic acid according to the present invention is introduced (hereinafter, simply referred to as "vector") include pBTrp2, pBTac1, and pBTac2 (all commercially available from Boehringer Mannheim GmbH), pKK233-2 (manufactured by Pharmacia Corporation), pSE280 (manufactured by Invitrogen Corporation), pGEMEX-1 (manufactured by Promega Corporation), pQE-8 (manufactured by QIAGEN Corporation), pKYP10 (Japanese Unexamined Patent Publication No. S58-110600), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(-) (manufactured by Stratagene Corporation), pTrs30 [constructed from *Escherichia coli* JM109/pTrS30 (FERM BP-5407)], pTrs32 [constructed from *Escherichia coli* JM109/pTrS32 (FERM BP-5408)], pGHA2 [constructed from *Escherichia coli* IGHA2 (FERM B-400), Japanese Unexamined Patent Publication No. S60-221091], pGKA2 [constructed from *Escherichia coli* IGKA2 (FERM BP-6798), Japanese Unexamined Patent Publication No. 60-221091], pTerm2 (U.S. Pat. Nos. 4,686,191, 4,939,094, 5,160,735), pSupex, pUB110, pTP5, pC194, pEG400 [J. Bacteriol., 172, 2392 (1990)], pGEX (manufactured by Pharmacia Corporation), and pET systems (manufactured by Novagen, Inc.).

In the case where *Escherichia coli* is used as a host, pUC18, pBluescriptII, pSupex, pET22b, pCold, or the like can be mentioned as a suitable vector.

Specific examples of vectors suitable for microorganisms belonging to the genus *Brevibacillus* include pUB110 or pHY500 (Japanese Unexamined Patent Publication No. H2-31682), pNY700 (Japanese Unexamined Patent Publication No. H4-278091), pHY4831 (J. Bacteriol., 1987, 1239-1245), pNU200 (UDAKA Shigezou, Journal of the Agricultural Chemical Society of Japan, 1987, 61: 669-676), pNU100 (Appl. Microbiol. Biotechnol., 1989, 30: 75-80), pNU211 (J. Biochem., 1992, 112: 488-491), pNU211R2L5 (Japanese Unexamined Patent Publication No. H7-170984), pNH301 (Appl. Environ. Microbiol., 1992, 58: 525-531), pNH326, pNH400 (J. Bacteriol., 1995, 177: 745-749), and pHT210 (Japanese Unexamined Patent Publication No. H6-133782), pHT110R2L5 (Appl. Microbiol. Biotechnol., 1994, 42: 358-363), which are known as *Bacillus subtilis* vectors; and pNCO2 (Japanese Unexamined Patent Publication No. 2002-238569) which is a shuttle vector between *Escherichia coli* and a microorganism belonging to the genus *Brevibacillus*.

The promoter is not limited as long as it functions in a host cell. Examples thereof include promoters derived from *Escherichia coli* or phage such as a trp promoter (Ptrp), a lac promoter, a PL promoter, a PR promoter, and a T7 promoter. Also, promoters artificially designed and modified, such as a promoter (Ptrpx2) in which two Ptrps are connected in series, a tac promoter, a lacT7 promoter, and a let I promoter, can also be used.

It is preferable to use a plasmid in which the distance between the Shine-Dalgarno sequence, which is a ribosome binding sequence, and the initiation codon is adjusted to an appropriate distance (for example, 6 to 18 bases). In the expression vector according to the present invention, a transcription termination sequence is not necessarily required for the expression of the nucleic acid according to the present invention, but it is preferable to arrange a transcription termination sequence immediately below a structural gene.

Examples of eukaryotic hosts include yeast, filamentous fungi (mold and the like), and insect cells.

Examples of the yeast include yeasts belonging to the genus *Saccharomyces, Schizosaccharomyces, Kluyveromyces, Trichosporon, Schwanniomyces, Pichia, Candida, Yarrowia, Hansenula*, and the like. More specific examples of the yeast include *Saccharomyces cerevisiae, Schizosaccharomyces pombe, Kluyveromyces lactis, Kluyveromyces marxianus, Trichosporon pullulans, Schwanniomyces alluvius, Schwanniomyces occidentalis, Candida utilis, Pichia pastoris, Pichia angusta, Pichia methanolica, Pichia polymorpha, Pichia stipitis, Yarrowia lipolytica*, and *Hansenula polymorpha*.

It is preferable that the expression vector in the case where yeast is used as a host cell usually include an origin of replication (in the case where amplification in a host is required), a selection marker for propagation of the vector in *Escherichia coli*, a promoter and a terminator for recombinant protein expression in yeast, and a selection marker for yeast.

In the case where the expression vector is a non-integrating vector, it is preferable to further include an autonomously replicating sequence (ARS). This makes it possible to improve the stability of the expression vectors in cells (Myers, A. M., et al. (1986) Gene 45: 299-310).

Examples of the vector in the case where yeast is used as a host include YEP13 (ATCC 37115), YEp24 (ATCC 37051), YCp50 (ATCC 37419), Ylp, pHS19, pHS15, pA0804, pHIL3OI, pHIL-S1, pPIC9K, pPICZa, pGAPZa, and pPICZ B.

The promoter is not limited as long as it can be expressed in yeast. Examples of the promoter include a promoter of glycolytic genes such as hexose kinase, a PHO5 promoter, a PGK promoter, a GAP promoter, an ADH promoter, a gal 1 promoter, a gal 10 promoter, a heat shock polypeptide promoter, an MFα1 promoter, a CUP 1 promoter, a pGAP promoter, a pGCW14 promoter, an AOX1 promoter, and an MOX promoter.

As a method for introducing an expression vector into yeast, any method can be used as long as it introduces DNA into yeast. Examples thereof include an electroporation method (Methods Enzymol., 194, 182 (1990)), a spheroplast method (Proc. Natl. Acad. Sci., USA, 81, 4889 (1984)), a lithium acetate method (J. Bacteriol., 153, 163 (1983)), and a method described in Proc. Natl. Acad. Sci. USA, 75, 1929 (1978).

Examples of filamentous fungi include fungi belonging to the genus *Acremonium, Aspergillus, Ustilago, Trichoderma, Neurospora, Fusarium, Humicola, Penicillium, Myceliophtora, Botryts, Magnaporthe, Mucor, Metarhizium, Monascus, Rhizopus*, and *Rhizomucor*.

Specific examples of filamentous fungi include *Acremonium alabamense, Acremonium cellulolyticus, Aspergillus aculeatus, Aspergillus awamori, Aspergillus oryzae, Aspergillus sake, Aspergillus sojae, Aspergillus tubigensis, Aspergillus niger, Aspergillus nidulans, Aspergillus parasiticus, Aspergillus ficuum, Aspergillus phoeicus, Aspergillus foetidus, Aspergillus flavus, Aspergillus fumigatus, Aspergillus japonicus, Trichoderma viride, Trichoderma harzianum, Trichoderma reseei, Chrysosporium lucknowense, Ther-

*moascus, Sporotrichum, Sporotrichum cellulophilum, Talaromyces, Thielavia terrestris, Thielavia, Neurospora crassa, Fusarium oxysporus, Fusarium graminearum, Fusarium venenatum, Humicola insolens, Penicillium chrysogenum, Penicillium camemberti, Penicillium canescens, Penicillium emersonii, Penicillium funiculosum, Penicillium griseoroseum, Penicillium purpurogenum, Penicillium roqueforti, Myceliophtaora thermophilum, Mucor ambiguus, Mucor circinelloides, Mucor fragilis, Mucor hiemalis, Mucor inaequisporus, Mucor oblongiellipticus, Mucor racemosus, Mucor recurvus, Mocor saturninus, Mocor subtilissmus, Ogataea polymorpha, Phanerochaete chrysosporium, Rhizomucor miehei, Rhizomucor pusillus*, and *Rhizopus arrhizus*.

The promoter in the case where the host is a filamentous fungus may be any one of a gene related to a glycolytic system, a gene related to constitutive expression, an enzyme gene related to hydrolysis, and the like. Specific examples thereof include amyB, glaA, agdA, glaB, TEF1, xynF1 tannase gene, No. 8AN, gpdA, pgkA, enoA, melO, sodM, catA, and catB.

Introduction of the expression vector into filamentous fungi can be carried out by a conventionally known method. Examples thereof include the method of Cohen et al. (calcium chloride method) [Proc. Natl. Acad. Sci. USA, 69: 2110 (1972)], a protoplast method [Mol. Gen. Genet., 168: 111 (1979)], a competent method [J. Mol. Biol., 56: 209 (1971)], and an electroporation method.

Insect cells include, for example, lepidopteran insect cells, more specifically insect cells derived from *Spodoptera frugiperda* such as Sf9 and Sf21, and insect cells derived from *Trichoplusia ni* such as High 5.

Examples of the vector in the case where an insect cell is used as a host include baculoviruses such as *Autographa californica* nuclear polyhedrosis virus which is a virus that infects insects belonging to the family Noctuidae (Baculovirus Expression Vectors, A Laboratory Manual, W. H. Freeman and Company, New York (1992)).

In the case where an insect cell is used as a host, a polypeptide can be expressed by the method described in, for example, Current Protocols in Molecular Biology, Baculovirus Expression Vectors, A Laboratory Manual, W. H. Freeman and Company, New York (1992), or Bio/Technology, 6, 47 (1988).

That is, a recombinant gene transfer vector and a baculovirus are co-introduced into an insect cell to obtain a recombinant virus (expression vector) in an insect cell culture supernatant, and then the recombinant virus is further infected into an insect cell, whereby the polypeptide can be expressed. Examples of the gene transfer vector used in the above method include pVL1392, pVL1393, and pBlueBacIII (all manufactured by Invitorogen Corporation).

As a method for co-introducing a recombinant gene transfer vector and a baculovirus into an insect cell for constructing the recombinant virus, for example, a calcium phosphate method (Japanese Unexamined Patent Publication No. H2-227075), a lipofection method (Proc. Natl. Acad. Sci. USA, 84, 7413 (1987)), or the like can be mentioned.

The recombinant vector according to the present invention preferably further contains a selection marker gene for selecting a transformant. For example, in *Escherichia coli*, resistance genes for various drugs such as tetracycline, ampicillin, and kanamycin can be used as selection marker genes. A recessive selection marker capable of complementing a genetic mutation involved in auxotrophy can also be used. In yeast, a resistance gene for geneticin can be used as a selection marker gene, and a gene complementing a genetic mutation involved in auxotrophy, or a selection marker such as LEU2, URA3, TRP1, or HIS3 can also be used. Examples of the selection marker gene for filamentous fungi include a marker gene selected from the group consisting of niaD (Biosci. Biotechnol. Biochem., 59, 1795-1797 (1995)), argB (Enzyme Microbiol Technol, 6, 386-389, (1984)), sC (Gene, 84, 329-334, (1989)), ptrA (BiosciBiotechnol Biochem, 64, 1416-1421, (2000)), pyrG (Biochem-Biophys Res Commun, 112, 284-289, (1983)), amdS (Gene, 26, 205-221, (1983)), aureobasidin resistance gene (Mol Gen Genet, 261, 290-296, (1999)), benomyl resistance gene (Proc Natl Acad Sci USA, 83, 4869-4873, (1986)) and hygromycin resistance gene (Gene, 57, 21-26, (1987)), and a leucine auxotrophy-complementing gene. Further, in the case where the host is an auxotrophic mutant strain, a wild-type gene complementing the auxotrophy can also be used as a selection marker gene.

The selection of the host transformed with the expression vector according to the present invention can be carried out by plaque hybridization and colony hybridization using a probe that selectively binds to the nucleic acid according to the present invention. As the probe, it is possible to use a probe obtained by modifying a partial DNA fragment amplified by a PCR method based on sequence information of the nucleic acid according to the present invention with a radioisotope or digoxigenin.

[Method for Producing Modified Fibroin]

The modified fibroin according to the present invention can be produced by a method including a step in which a host transformed with the expression vector according to the present invention expresses the nucleic acid according to the present invention. As for the expression method, secretory production, fusion protein expression, or the like, in addition to direct expression, can be carried out according to the method described in Molecular Cloning, 2nd edition. In the case where it is expressed by yeast, an animal cell, or an insect cell, a modified fibroin can be obtained as a polypeptide to which a sugar or sugar chain is added.

The modified fibroin according to the present invention can be produced, for example, by culturing a host transformed with the expression vector according to the present invention in a culture medium, producing and accumulating the modified fibroin according to the present invention in the culture medium, and then collecting the modified fibroin from the culture medium. The method for culturing the host according to the present invention in a culture medium can be carried out according to a method commonly used for culturing a host.

In the case where the host according to the present invention is a prokaryote such as *Escherichia coli* or a eukaryote such as yeast, any of a natural medium and a synthetic medium may be used as a culture medium of the host according to the present invention as long as it contains a carbon source, a nitrogen source, inorganic salts and the like which can be assimilated by the host and it is capable of efficiently culturing the host.

As the carbon source, any carbon source that can be assimilated by the host may be used. Examples of the carbon source that can be used include carbohydrates such as glucose, fructose, sucrose, and molasses, starch and starch hydrolyzates containing them, organic acids such as acetic acid and propionic acid, and alcohols such as ethanol and propanol.

Examples of the nitrogen source that can be used include ammonium salts of inorganic or organic acids such as ammonia, ammonium chloride, ammonium sulfate, ammonium acetate and ammonium phosphate, other nitrogen-containing compounds, peptone, meat extract, yeast extract, corn steep liquor, casein hydrolyzate, soybean cake and soybean cake hydrolyzate, various fermented microbial cells and digested products thereof.

Examples of the inorganic salt that can be used include potassium dihydrogen phosphate, dipotassium phosphate, magnesium phosphate, magnesium sulfate, sodium chloride, ferrous sulfate, manganese sulfate, copper sulfate, and calcium carbonate.

Culture of a prokaryote such as *Escherichia coli* or a eukaryote such as yeast can be carried out under aerobic conditions such as shaking culture or deep aeration stirring culture. The culture temperature is, for example, 15 to 40° C. The culture time is usually 16 hours to 7 days. It is preferable to maintain the pH of the culture medium during the culture at 3.0 to 9.0. The pH of the culture medium can be adjusted using an inorganic acid, an organic acid, an alkali solution, urea, calcium carbonate, ammonia, or the like.

In addition, antibiotics such as ampicillin and tetracycline may be added to the culture medium as necessary during the culture. In the case of culturing a microorganism transformed with an expression vector using an inducible promoter as a promoter, an inducer may be added to the medium as necessary. For example, in the case of culturing a microorganism transformed with an expression vector using a lac promoter, isopropyl-β-D-thiogalactopyranoside or the like is used, and in the case of culturing a microorganism transformed with an expression vector using a trp promoter, indole acrylic acid or the like may be added to the medium.

As a culture medium for insect cells, commonly used TNM-FH medium (manufactured by Pharmingen Inc.), Sf-900 II SFM medium (manufactured by Life Technologies Corporation), ExCell 400 and ExCell 405 (both manufactured by JRH Biosciences Inc.), Grace's Insect Medium (Nature, 195, 788 (1962)), and the like can be used.

Culture of insect cells can be carried out, for example, for a culture time of 1 to 5 days under conditions such as pH 6 to 7 of culture medium and culture temperature 25 to 30° C. In addition, an antibiotic such as gentamicin may be added to the culture medium as necessary during the culture.

In the case where the host is a plant cell, the transformed plant cell may be directly cultured, or it may be differentiated into a plant organ and then cultured. As the culture medium for culturing a plant cell, for example, commonly used Murashige and Skoog (MS) medium, White medium, or a medium in which a plant hormone such as auxin or cytokinin is added to these media can be used.

Culture of animal cells can be carried out, for example, for a culture time of 3 to 60 days under conditions such as pH 5 to 9 of the culture medium and culture temperature 20 to 40° C. In addition, an antibiotic such as kanamycin or hygromycin may be added to the medium as necessary during the culture.

As a method for producing a modified fibroin using a host transformed with the expression vector according to the present invention, there are a method for producing the modified fibroin in a host cell, a method for secreting the modified fibroin outside the host cell, and a method for producing the modified fibroin on the outer membrane of the host cell. Each of these methods can be selected depending on the host cell to be used and the structure of the modified fibroin to be produced.

For example, in the case where a modified fibroin is produced in the host cell or on the outer membrane of the host cell, the production method can be altered to actively secrete the modified fibroin outside the host cell according to the method of Paulson et al. (J. Biol. Chem., 264, 17619 (1989)), the method of Lowe et al. (Proc. Natl. Acad. Sci. USA, 86, 8227 (1989), Genes Develop., 4, 1288 (1990)), or the methods described in Japanese Unexamined Patent Publication No. H5-336963, International Publication No. WO 94/23021, and the like. That is, the modified fibroin can be actively secreted outside the host cell by expressing the modified fibroin in a form in which a signal peptide is added to a polypeptide containing an active site of a modified fibroin using a gene recombination technique.

The modified fibroin produced by the host transformed with the expression vector according to the present invention can be isolated and purified by a method commonly used for protein isolation and purification. For example, in the case where the modified fibroin is expressed in a dissolved state in cells, the host cells are recovered by centrifugation after completion of the culture, suspended in an aqueous buffer solution, and then disrupted using an ultrasonicator, a French press, a Manton-Gaulin homogenizer, a Dyno-Mill, or the like to obtain a cell-free extract. From the supernatant obtained by centrifuging the cell-free extract, a purified preparation can be obtained by a method commonly used for protein isolation and purification, that is, a solvent extraction method, a salting-out method using ammonium sulfate or the like, a desalting method, a precipitation method using an organic solvent, an anion exchange chromatography method using a resin such as diethylaminoethyl (DEAE)-Sepharose or DIAION HPA-75 (manufactured by Mitsubishi Kasei Kogyo Kabushiki Kaisha), a cation exchange chromatography method using a resin such as S-Sepharose FF (Pharmacia Corporation), a hydrophobic chromatography method using a resin such as butyl sepharose or phenyl sepharose, a gel filtration method using a molecular sieve, an affinity chromatography method, a chromatofocusing method, an electrophoresis method such as isoelectric focusing or the like, alone or in combination thereof.

As the chromatography, column chromatography using phenyl-TOYOPEARL (available from Tosoh Corporation), DEAE-TOYOPEARL (available from Tosoh Corporation), and Sephadex G-150 (available from Pharmacia Biotech Inc.) is preferably used.

In the case where the modified fibroin is expressed by the formation of an insoluble matter in the cell, similarly, the host cells are recovered, disrupted and centrifuged to recover the insoluble matter of the modified fibroin as a precipitated fraction. The recovered insoluble matter of the modified fibroin can be solubilized with a protein denaturing agent. After this operation, a purified preparation of modified fibroin can be obtained by the same isolation and purification method as described above.

In the case where a modified fibroin or a derivative in which a sugar chain has been added to the modified fibroin is secreted extracellularly, the modified fibroin or the derivative thereof can be recovered from the culture supernatant. That is, a culture supernatant is obtained by treating the culture by a technique such as centrifugation, and a purified preparation can be obtained from the culture supernatant by using the same isolation and purification method as described above.

In the modified fibroin according to the present invention, formation of an ester bond by contact with a carboxylic acid such as formic acid is reduced. As a result, an odor is less likely to be generated even when the modified fibroin according to the present embodiment is left in the air. Therefore, the method for producing the modified fibroin according to the present embodiment may include a step of bringing the modified fibroin into contact with a carboxylic acid such as formic acid.

[Artificially Modified Fibroin Composition]

An artificially modified fibroin composition according to the present embodiment contains at least the modified fibroin according to the present invention.

The content of the modified fibroin in the artificially modified fibroin composition may be 30 to 100% by mass, preferably 35 to 100% by mass, and more preferably 40 to 100% by mass based on the total amount of the artificially modified fibroin composition.

The artificially modified fibroin composition according to the present embodiment may further contain another additive depending on its form, application, and the like. Examples of the additive include a plasticizer, a leveling agent, a crosslinking agent, a crystal nucleating agent, an antioxidant, an ultraviolet absorber, a colorant, a filler, and a synthetic resin. The content of the additive may be 50 parts by mass or less with respect to 100 parts by mass of the total amount of the modified fibroin.

The artificially modified fibroin composition according to the present embodiment may be in any form of powder, paste, and liquid (for example, suspension or solution). The artificially modified fibroin composition according to the present embodiment may be in a form of a raw material composition (for example, protein powder or a doping liquid), or also may be in a form of a molded body (for example, a fiber, a yarn, a film, a foam, a grain, or a mold-molded body) containing the artificially modified fibroin composition or consisting of the artificially modified fibroin composition.

(Doping Liquid)

The artificially modified fibroin composition according to the present embodiment may be in a form of a doping liquid. The doping liquid according to the present embodiment contains at least the modified fibroin and a solvent. The doping liquid according to the present embodiment may further contain a dissolution promoter. The doping liquid according to the present embodiment may further contain a protein other than the modified fibroin.

Examples of the solvent include an aqueous solution or the like containing hexafluoroisopropanol (HFIP), hexafluoroacetone (HFA), dimethylsulfoxide (DMSO), N,N-dimethylformamide (DMF), formic acid, urea, guanidine, sodium dodecylsulfate (SDS), lithium bromide, calcium chloride, and lithium thiocyanate. These solvents may be used singly or in combination of two or more kinds thereof.

The content of the modified fibroin in the doping liquid may be 15% by mass or more, 30% by mass or more, 40% by mass or more, or 50% by mass or more based on the total mass of the doping liquid. The content of the modified fibroin may be 70% by mass or less, 65% by mass or less, or 60% by mass or less based on the total mass of the doping liquid from a viewpoint of production efficiency of the doping liquid.

Examples of the dissolution promoter include an inorganic salt consisting of the following Lewis acid and Lewis base. Examples of the Lewis base include an oxo acid ion (such as a nitrate ion and a perchlorate ion), a metal oxo acid ion (such as a permanganate ion), a halide ion, a thiocyanate ion, a cyanate ion, and the like. Examples of the Lewis acid include a metal ions such as an alkali metal ion and an alkaline earth metal ion, a polyatomic ion such as an ammonium ion, and a complex ion. Specific examples of the inorganic salts consisting of a Lewis acid and a Lewis base include: lithium salts such as lithium chloride, lithium bromide, lithium iodide, lithium nitrate, lithium perchlorate, and lithium thiocyanate; calcium salts such as calcium chloride, calcium bromide, calcium iodide, calcium nitrate, calcium perchlorate and calcium thiocyanate; iron salts such as iron chloride, iron bromide, iron iodide, iron nitrate, iron perchlorate and iron thiocyanate; aluminum salts such as aluminum chloride, aluminum bromide, aluminum iodide, aluminum nitrate, aluminum perchlorate, and aluminum thiocyanate; potassium salts such as potassium chloride, potassium bromide, potassium iodide, potassium nitrate, potassium perchlorate, and potassium thiocyanate; sodium salts such as sodium chloride, sodium bromide, sodium iodide, sodium nitrate, sodium perchlorate and sodium thiocyanate; zinc salts such as zinc chloride, zinc bromide, zinc iodide, zinc nitrate, zinc perchlorate and zinc thiocyanate, chloride; magnesium salts such as magnesium chloride, magnesium bromide, magnesium iodide, magnesium nitrate, magnesium perchlorate, and magnesium thiocyanate; barium salts such as barium chloride, barium bromide, barium iodide, barium nitrate, barium perchlorate, and barium thiocyanate; and strontium salts such as strontium chloride, strontium bromide, strontium iodide, strontium nitrate, strontium perchlorate, and strontium thiocyanate.

The content of the dissolution promoter may be 1.0 parts by mass or more, 5.0 parts by mass or more, 9.0 parts by mass or more, 15 parts by mass or more, or 20.0 parts by mass or more with respect to 100 parts by mass of the total amount of the modified fibroin. The content of the dissolution promoter may be 40 parts by mass or less, 35 parts by mass or less, or 30 parts by mass or less with respect to 100 parts by mass of the total amount of the modified fibroin.

During production of the doping liquid according to the present embodiment, heating may be performed at 30 to 90° C. It is only required to appropriately set the temperature at which dissolution is possible according to the solvent to be used, the type of modified fibroin, and the like. Shaking and stirring may be performed to promote dissolution.

The viscosity of the doping liquid according to the present embodiment may be appropriately set according to application or the like of the doping liquid. For example, when the doping liquid according to the present embodiment is used as a spinning stock solution, the viscosity of the doping liquid may be set according to a spinning method. For example, it is only required to set the viscosity to 100 to 15,000 cP (centipoise) at 35° C. or 100 to 30,000 cP (centipoise) at 40° C. The viscosity of the spinning stock solution can be measured using, for example, an "EMS viscometer" (trade name) manufactured by Kyoto Electronics Manufacturing Co., Ltd.

(Protein Fiber)

The artificially modified fibroin composition according to the present embodiment may be in a form of protein fiber. The protein fiber can be obtained, for example, by spinning the above-described doping liquid (spinning solution) by a method usually used for spinning fibroin.

The spinning method is not particularly limited as long as it is a method capable of spinning the modified fibroin according to the present invention, and examples thereof include dry-type spinning, melt spinning, and wet-type spinning. A preferred spinning method is wet-type spinning.

In wet-type spinning, an undrawn yarn with the shape of yarn can be obtained by extruding, from a spinneret (nozzle), a doping liquid into a coagulation liquid (coagulation liquid bath) in which the modified fibroin is solidified. The coagulation liquid may be any solution that can be desolvated, and examples thereof include lower alcohols having 1 to 5 carbon atoms such as methanol, ethanol and 2-propanol, and acetone. Water may be appropriately added to the coagulation liquid. The temperature of the coagulation liquid is preferably 0 to 30° C. In a case where a syringe pump having a nozzle with a diameter of 0.1 to 0.6 mm is used as the spinneret, the extrusion speed is preferably 0.2 to 6.0 ml/hour per hole and more preferably 1.4 to 4.0 ml/hour. The length of the coagulation liquid bath is not limited as long as the desolvation can be efficiently carried out, and is, for example, 200 to 500 mm. The withdrawing speed of the undrawn yarn may be, for example, 1 to 20 m/min and preferably 1 to 3 m/min. The residence time may be, for example, 0.01 to 3 minutes and preferably 0.05 to 0.15 minutes. In addition, drawing (pre-drawing) may be performed in the coagulation liquid. In order to suppress evaporation of the lower alcohol, the coagulation liquid may be kept at a low temperature, and yarn may be withdrawn in an undrawn state. The coagulation liquid bath may be provided in multiple stages, and the drawing may be performed in each stage or in a specific stage as necessary.

The undrawn yarn (or pre-drawn yarn) obtained by the above-described method can be made into a drawn yarn through a drawing step. Examples of the drawing method include wet heat drawing and dry heat drawing.

The wet heat drawing can be performed in warm water, in a solution obtained by adding an organic solvent or the like to warm water, or in heated steam. The temperature may be, for example, 50 to 90° C. and preferably 75 to 85° C. In the wet heat drawing, the undrawn yarn (or pre-drawn yarn) can be drawn, for example, by 1 to 10 times and preferably by 2 to 8 times.

The dry heat drawing can be performed using an electric tubular furnace, a dry heat plate, or the like. The temperature may be, for example, 140 to 270° C., and is preferably 160 to 230° C. In the dry heat drawing, the undrawn yarn (or pre-drawn yarn) can be drawn, for example, by 0.5 to 8 times and preferably by 1 to 4 times.

The wet heat drawing and the dry heat drawing may be performed independently or in combination, or may be performed in multiple stages. That is, the wet heat drawing and the dry heat drawing can be performed in suitable combination, for example, in a manner in which a first stage drawing is performed by wet heat drawing and a second stage drawing is performed by dry heat drawing or in a manner in which the first stage drawing is performed by wet heat drawing, the second stage drawing is performed by wet heat drawing, and a third stage drawing is performed by dry heat drawing.

The final drawing ratio in the drawing step is, for example, 5 to 20 times and preferably 6 to 11 times with respect to the undrawn yarn (or pre-drawn yarn).

The protein fiber may be drawn and then chemically crosslinked between polypeptide molecules within the protein fiber. Examples of functional groups that can be crosslinked include an amino group, a carboxyl group, a thiol groups, and a hydroxy group. For example, an amino group of a lysine side chain contained in the polypeptide can be crosslinked through an amide bond by dehydration condensation with a carboxyl group of a glutamic acid or aspartic acid side chain. The crosslinking may be performed by performing a dehydration condensation reaction under vacuum heating, or by a dehydration condensation agent such as carbodiimides.

The crosslinking between polypeptide molecules may be performed using a crosslinking agent such as carbodiimides or glutaraldehyde, or may be performed using an enzyme such as transglutaminase. Carbodiimides are compounds represented by the general formula $R_1N=C=NR_2$ (where $R_1$ and $R_2$ each independently represent an organic group containing an alkyl group having 1 to 6 carbon atoms or a cycloalkyl group). Specific examples of carbodiimides include 1-ethyl-3-(3-dimethylaminopropyl) carbodiimide hydrochloride (EDC), N,N'-dicyclohexylcarbodiimide (DCC), 1-cyclohexyl-3-(2-morpholinoethyl) carbodiimide, and diisopropyl carbodiimide (DIC). Among these, EDC and DIC are preferable because they have a high ability to form an amide bond between polypeptide molecules and easily perform a crosslinking reaction.

The crosslinking treatment is preferably performed by applying a crosslinking agent to the protein fiber and performing crosslinking with vacuum heating and drying. As the crosslinking agent, a pure product may be applied to the protein fiber, or a product diluted with a lower alcohol having 1 to 5 carbon atoms, a buffer solution, or the like to a concentration of 0.005 to 10% by mass may be applied to the protein fiber. The crosslinking treatment is preferably performed at a temperature of 20 to 45° C. for 3 to 42 hours. Higher stress (strength) can be imparted to the protein fiber by the crosslinking treatment.

(Film)

The artificially modified fibroin composition according to the present embodiment may be in a form of a film. The film can be obtained, for example, by cast-molding the above-described doping liquid on a surface of a base material and drying and/or desolvating the doping liquid.

The viscosity of the doping liquid is preferably 15 to 80 cP (centipoise) and more preferably 20 to 70 cP.

The concentration of the modified fibroin according to the present invention is preferably 3 to 50% by mass, more preferably 3.5 to 35% by mass, and still more preferably 4.2 to 15.8% by mass in a case where the doping liquid is set to 100% by mass.

When preparing the doping liquid, heating may be performed at 30 to 60° C. Shaking and stirring may be performed to promote dissolution.

The base material may be a resin substrate, a glass substrate, a metal substrate, or the like. The base material is preferably a resin substrate from the viewpoint that the film after cast-molding can be easily peeled off. The resin substrate may be, for example, a polyethylene terephthalate (PET) film, a fluororesin film such as polytetrafluoroethylene, a polypropylene (PP) film, or a release film in which a silicone compound is immobilized on the surface of these films. It is more preferable that the base material is stable with respect to solvent such as HFIP and DMSO, is stably cast-molded with the doping liquid, and from the viewpoint that the film after molding can be easily peeled off is a release film in which the silicone compound is immobilized in the PET film or on the surface of the PET film.

The specific procedure is as follows. First, the doping liquid is cast on the surface of the base material, and a wet film having a predetermined thickness (for example, a thickness of 1 to 1,000 µm after drying and/or desolvation) is produced using a film thickness control means such as an applicator, a knife coater, and a bar coater.

Drying and/or desolvation can be performed by a dry-type method and/or by a wet-type method. Examples of the dry-type method include vacuum drying, hot air drying, and air drying. Examples of the wet-type method include a method in which a cast film is immersed in a desolvation liquid (also referred to as a coagulation liquid) to remove the solvent. Examples of the desolvation liquid include water, alcohol liquids such as lower alcohols having 1 to 5 carbon atoms including methanol, ethanol, and 2-propanol, and a mixed liquid of water and the alcohol. The temperature of the desolvation liquid (coagulation liquid) is preferably 0 to 90° C.

The undrawn film after drying and/or desolvation can be uniaxially or biaxially drawn in water. Biaxial drawing may be sequential drawing or simultaneous biaxial drawing. Multi-stage drawing of two or more stages may be performed. The drawing ratio is preferably 1.01 to 6 times and more preferably 1.05 to 4 times both in length and width. Within this range, it is easy to balance stress with strain. The drawing in water is preferably performed at a water temperature of 20 to 90° C. The drawn film is preferably heat-fixed by a dry heat of 50 to 200° C. for 5 to 600 seconds. This heat-fixing provides dimensional stability to the film at room temperature. A uniaxially drawn film becomes a uniaxially aligned film, and a biaxially drawn film becomes a biaxially aligned film.

[Method for Producing Artificially Modified Fibroin Composition]

The artificially modified fibroin composition according to the present invention can be produced by a method including a step of preparing the modified fibroin according to the present invention. The method for producing the artificially modified fibroin composition according to the present invention may further include a step of adjusting a modified fibroin solution (for example, a doping liquid) containing the modified fibroin according to the present invention and a carboxylic acid.

In the modified fibroin according to the present invention, formation of an ester bond by contact with a carboxylic acid such as formic acid is reduced. As a result, an odor is less likely to be generated even when the modified fibroin according to the present embodiment is left in the air. Therefore, the method for producing the artificially modified fibroin composition according to the present embodiment may include a step of bringing the modified fibroin into contact with a carboxylic acid such as formic acid.

[Product]

The protein fiber formed according to the present invention can be applied to a woven fabric, a knitted fabric, a braided fabric, a non-woven fabric, and the like, as a fiber (such as a long fiber, a short fiber, a multifilament, and a monofilament) or a yarn (such as a spun yarn, a twisted yarn, a false twisted yarn, a processed yarn, a blended yarn, and a blended spun yarn). This protein fiber can also be applied to high strength applications such as a rope, a surgical suture, a flexible stop for electrical components, and a physiologically active material for implantation (for example, artificial ligament and aortic band).

In addition to the fiber and the film, the artificially modified fibroin composition according to the present invention can also be applied to a foam, a grain (such as a sphere or a non-sphere), a nanofibril, a gel (such as a hydrogel), a resin and equivalents thereof, which can be produced in accordance with the method described in Japanese Unexamined Patent Publication No. 2009-505668, Japanese Patent No. 5678283, Japanese Patent No. 4638735, or the like.

EXAMPLES

Hereinafter, the present invention will be described more specifically based on Examples. However, the present invention is not limited to following Examples.

Test Example 1

[Production of Modified Fibroin]
(1) Production of Expression Vector

Modified fibroins (PRT918, PRT1104, PRT1105, PRT1103, PRT1107, PRT1083, PRT826, and PRT1127) respectively having the amino acid sequence set forth in SEQ ID NOs: 9 to 16 were designed.

The amino acid sequence set forth in SEQ ID NO: 9 (PRT918) has an amino acid sequence obtained by adding the amino acid sequence (including a His tag) set forth in SEQ ID NO: 17 to the N-terminal of the amino acid sequence set forth in SEQ ID NO: 1 (Met-PRT918) (Comparative Example 1).

The amino acid sequences set forth in SEQ ID NOs: 10 to 13 (PRT1104, PRT1105, PRT1103, and PRT1107) are as described above (Examples 1 to 4).

The amino acid sequence set forth in SEQ ID NO: 14 (PRT1083) is obtained by substituting GPGA in the amino acid sequence set forth in SEQ ID NO: 9 (PRT918) with GTGA, substituting GPGS with GTGS, substituting GPGV with GLGV, substituting GPGI with GTGI, substituting GPY with GLY, and substituting GPS with GTS (Comparative Example 2).

The amino acid sequence set forth in SEQ ID NO: 15 (PRT826) is obtained by substituting a serine residue (S) with a threonine residue (T) in an amino acid sequence obtained by adding the amino acid sequence (including a His tag) set forth in SEQ ID NO: 18 to the N-terminal of the amino acid sequence set forth in SEQ ID NO: 19 (Met-PRT410) (Example 5).

The amino acid sequence set forth in SEQ ID NO: 16 (PRT1127) is obtained by substituting a serine residue (S) with a threonine residue (T) in the amino acid sequence set forth in SEQ ID NO: 9 (PRT918) (Example 6).

A threonine residue content rate, a serine residue content rate, and a content rate of threonine residue and serine residue in each of the modified fibroins having the amino acid sequences set forth in SEQ ID NOs: 9 to 16 are as illustrated in Table 1.

TABLE 1

| | Modified fibroin | Serine residue content rate | Threonine residue content rate | Content rate of serine residue and threonine residue |
|---|---|---|---|---|
| Comparative Example 1 | PRT918 (SEQ ID NO: 9) | 9.65% | 0% | 9.65% |
| Example 1 | PRT1104 (SEQ ID NO: 10) | 0.67% | 0% | 0.67% |
| Example 2 | PRT1105 (SEQ ID NO: 11) | 0% | 0% | 0% |
| Example 3 | PRT1103 (SEQ ID NO: 12) | 0.67 | 0% | 0.67% |
| Example 4 | PRT1107 (SEQ ID NO: 13) | 0% | 0% | 0% |
| Comparative Example 2 | PRT1083 (SEQ ID NO: 14) | 9.65% | 6.32% | 15.97% |

TABLE 1-continued

|  | Modified fibroin | Serine residue content rate | Threonine residue content rate | Content rate of serine residue and threonine residue |
|---|---|---|---|---|
| Example 5 | PRT826 (SEQ ID NO: 15) | 0% | 9.65% | 9.65% |
| Example 6 | PRT1127 (SEQ ID NO: 16) | 0% | 9.65% | 9.65% |

A nucleic acid encoding the designed modified fibroin was synthesized. In the nucleic acid, an NdeI site was added to the 5' end and an EcoRI site was added downstream of the stop codon. The nucleic acid was cloned into a cloning vector (pUC118). Thereafter, the nucleic acid was enzymatically cleaved by treatment with NdeI and EcoRI, and then recombinated into a protein expression vector pET-22b(+) to obtain an expression vector.

(2) Production of Protein

*Escherichia coli* BLR (DE3) was transformed with the obtained expression vector. The transformed *Escherichia coli* was cultured in 2 mL of an LB medium containing ampicillin for 15 hours. The culture solution was added to 100 mL of a seed culture medium (Table 2) containing ampicillin so that the $OD_{600}$ was 0.005. While maintaining the temperature of the culture solution at 30° C., flask culture was carried out (for about 15 hours) until the $OD_{600}$ reached 5, thereby obtaining a seed culture solution.

TABLE 2

Seed culture medium

| Reagent | Concentration (g/L) |
|---|---|
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter containing 500 mL of a production medium (Table 3) so that the $OD_{600}$ was 0.05. The culture was carried out while keeping the culture solution temperature at 37° C. and controlling the pH constant at 6.9. Further, the dissolved oxygen concentration in the culture solution was maintained at 20% of the dissolved oxygen saturation concentration.

TABLE 3

Production medium

| Reagent | Concentration (g/L) |
|---|---|
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| Adeka nol (Adeka, LG-295S) | 0.1 (mL/L) |

Immediately after glucose in the production medium was completely consumed, a feed solution (455 g/1 L of glucose and 120 g/1 L of Yeast Extract) was added at a rate of 1 mL/min. The culture was carried out while keeping the culture solution temperature at 37° C. and controlling the pH constant at 6.9. Further, the dissolved oxygen concentration in the culture solution was maintained at 20% of the dissolved oxygen saturation concentration, and the culture was carried out for 20 hours. Thereafter, 1 M isopropyl-β-thiogalactopyranoside (IPTG) was added to the culture solution to a final concentration of 1 mM to induce the expression of the modified fibroin. 20 hours after addition of IPTG, the culture solution was centrifuged to recover the bacterial cell pellet. SDS-PAGE was carried out using bacterial cell pellets prepared from the culture solution before the addition of IPTG and after the addition of IPTG, and the expression of the target modified fibroin was checked by the IPTG addition-dependent appearance of a band equivalent to a target modified fibroin size.

(3) Purification of Protein

The bacterial cell pellet recovered 2 hours after the addition of IPTG was washed with 20 mM Tris-HCl buffer solution (pH 7.4). The bacterial cell pellet after washing was suspended in 20 mM Tris-HCl buffer solution (pH 7.4) containing about 1 mM PMSF, and the cell suspension was disrupted with a high-pressure homogenizer (manufactured by GEA Niro Soavi SpA). The disrupted cells were centrifuged to obtain a precipitate. The obtained precipitate was washed with 20 mM Tris-HCl buffer solution (pH 7.4) until the obtained precipitate became highly pure. The precipitate after washing was suspended in 8 M guanidine buffer solution (8 M guanidine hydrochloride, 10 mM sodium dihydrogen phosphate, 20 mM NaCl, 1 mM Tris-HCl, pH 7.0) so that the concentration of the suspension was 100 mg/mL, and dissolved by stirring with a stirrer at 60° C. for 30 minutes. After dissolution, dialysis was carried out in water using a dialysis tube (cellulose tube 36/32 manufactured by Sanko Junyaku Co., Ltd.). The white aggregated protein obtained after dialysis was collected by centrifugation, moisture was removed with a lyophilizer, and a lyophilized powder was collected to obtain modified fibroins (PRT918, PRT1104, PRT1105, PRT1103, PRT1107, PRT1083, PRT826, and PRT1127).

[Production and Evaluation of Protein Film]

(1) Production of Protein Film

The obtained dry powder of the modified fibroin was added to formic acid and heated at 40° C. for one hour to be dissolved, thereby obtaining a doping liquid (protein concentration in the doping liquid: 26% by mass).

The obtained doping liquid was applied to a slide glass at a thickness of about 0.5 mm, and sequentially immersed in acetone and water (each for 15 minutes) to perform solidification and washing. Thereafter, the film was naturally dried overnight and then peeled off from the slide glass to obtain a sample. The film had a thickness of about 0.5 to 1.0 mm.

(2) Evaluation of Protein Film

An infrared absorption spectrum of the produced film sample was measured using the following measuring apparatus to evaluate the degree of generation of a formate in the film sample.

Measuring apparatus: NICOLET™ iS50 FT-IR (manufacturer: Thermo Fisher Scientific Inc.).

The degree of generation of a formate was evaluated by calculating an absorbance ratio P1/P2. The smaller the absorbance ratio P1/P2 is, the less the formate is.

P1: peak height of 1725 cm$^{-1}$ (peak based on C=O of ester)
P2: peak height at 1445 cm$^{-1}$ (peak based on amide III of protein)

Results are illustrated in FIG. 1 and Table 4. A film formed of each of the modified fibroins of Examples 1 to 6 having a reduced serine residue content rate reduced generation of a formate. In a film formed of each of the modified fibroins of Examples 1 to 4 having a threonine residue content rate of 9% or less and a content rate of serine residue and threonine residue of 9% or less, no peak was observed in a formate absorption region (1715 to 1730 cm$^{-1}$), and no formate was generated. On the other hand, in a film formed of each of the modified fibroins of Comparative Examples 1 and 2 having a high serine residue content rate, a peak was observed in the formate absorption region, and it was confirmed that a large amount of formate was generated.

TABLE 4

|  | Modified fibroin | Absorbance ratio P1/P2 |
| --- | --- | --- |
| Comparative Example 1 | PRT918 (SEQ ID NO: 9) | 0.030 |
| Example 1 | PRT1104 (SEQ ID NO: 10) | 0.000 |
| Example 2 | PRT1105 (SEQ ID NO: 11) | 0.000 |
| Example 3 | PRT1103 (SEQ ID NO: 12) | 0.000 |
| Example 4 | PRT1107 (SEQ ID NO: 13) | 0.000 |
| Comparative Example 2 | PRT1083 (SEQ ID NO: 14) | 0.086 |
| Example 5 | PRT826 (SEQ ID NO: 15) | 0.003 |
| Example 6 | PRT1127 (SEQ ID NO: 16) | 0.010 |

[Production and Evaluation of Protein Fiber]
(1) Production of Protein Fiber

The obtained dry powder of each of the modified fibroins (PRT918 and PRT1107) was added to formic acid and heated at 40° C. for one hour to be dissolved, thereby obtaining a doping liquid (protein concentration in the doping liquid: 26% by mass).

The obtained doping liquid was put into a syringe equipped with a nozzle having a pore size of 0.2 mm, and discharged into a coagulation bath (methanol bath) in a fibrous form to be solidified. The fiber that has passed through the methanol bath was washed and dried through a water bath and a hot roller, and then wound to obtain a fiber sample. The obtained fiber sample had a fiber diameter of about 30 to 40 μm.

(2) Evaluation of Protein Fiber

An infrared absorption spectrum of the produced fiber sample was measured using the following measuring apparatus to check whether or not a formate was generated in the fiber sample.

Measuring apparatus: NICOLET™ iS50 FT-IR (manufacturer: Thermo Fisher Scientific Inc.).

Results are illustrated in FIG. 2. In a protein fiber formed of the modified fibroin of Example 4 (PRT1107) having a reduced serine residue content rate, no peak was observed in the formate absorption region (1715 to 1730 cm$^{-1}$), and no formate was generated. On the other hand, in a protein fiber formed of the modified fibroin of Comparative Example 1 (PRT918) having a high serine residue content rate, a peak was observed in the formate absorption region, and it was confirmed that a large amount of formate was generated.

Test Example 2

[Production of modified fibroin]
(1) Production of Expression Vector

Modified fibroins (PRT219 and PRT1171) respectively having the amino acid sequences set forth in SEQ ID NOs: 24 and 25 were designed.

The amino acid sequence set forth in SEQ ID NO: 24 (PRT219) is obtained by removing a non-repetitive region at the C-terminal and adding a valine residue (V) in an ADF3 amino acid sequence (NOBI Genebank Accession No.: AAC47010, GI: 1263287) obtained by adding the amino acid sequence (including a His tag) set forth in SEQ ID NO: 26 and the amino acid sequence set forth in SEQ ID NO: 27 (amino acid sequence consisting of HRV3C protease (Human rhinovirus 3C protease) recognition site) to the N-terminal (Reference Example 1).

The amino acid sequence set forth in SEQ ID NO: 25 (PRT1171) is as described above (Example 7).

A threonine residue content rate, a serine residue content rate, and a content rate of threonine residue and serine residue in each of the modified fibroins having the amino acid sequences set forth in SEQ ID NOs: 24 and 25 are as illustrated in Table 5.

TABLE 5

|  | Modified fibroin | Serine residue content rate | Threonine residue content rate | Content rate of serine residue and threonine residue |
| --- | --- | --- | --- | --- |
| Reference Example 1 | PRT219 (SEQ ID NO: 24) | 6.0% | 0% | 6.0% |
| Example 7 | PRT1171 (SEQ ID NO: 25) | 2.2% | 0% | 2.2% |

A nucleic acid encoding the designed modified fibroin was synthesized. In the nucleic acid, an NdeI site was added to the 5' end and an EcoRI site was added downstream of the stop codon. The nucleic acid was cloned into a cloning vector (pUC118). Thereafter, the nucleic acid was enzymatically cleaved by treatment with NdeI and EcoRI, and then recombined into a protein expression vector pET-22b(+) to obtain an expression vector.

(2) Production and Purification of Protein

Production and purification of a protein were performed in a similar manner to Test Example 1.

[Production and Evaluation of Protein Film]
(1) Production of Protein Film

The obtained dry powder of the modified fibroin was added to formic acid and heated at 40° C. for one hour to be dissolved, thereby obtaining a doping liquid (protein concentration in the doping liquid: 26% by mass).

The obtained doping liquid was applied to a slide glass at a thickness of about 0.2 mm, and sequentially immersed in acetone and water (each for 15 minutes) to perform solidification and washing. Thereafter, the film was naturally dried overnight and then peeled off from the slide glass to obtain a sample. The film had a thickness of about 0.1 mm.

(2) Evaluation of Protein Film

The produced film sample (0.08 to 0.1 g) was immersed in 20 mL methanol and allowed to stand at 4° C. for 16 hours to extract formic acid by a transesterification reaction. Shaking was slightly performed to homogenize the concentration, and then the film sample was removed from the methanol. Using the obtained methanol (including the extracted formic acid) as an analysis sample, the extracted formic acid was quantified under the following conditions using a high performance liquid chromatography (HPLC).

HPLC system;
Liquid feeding unit: LC-20AD (manufactured by Shimadzu Corporation)
System controller: CBM-20A (manufactured by Shimadzu Corporation)
Autosampler: SIL-20AC (manufactured by Shimadzu Corporation)
Detector: SPD-M20A (manufactured by Shimadzu Corporation)
Column oven: CTO-20AC (manufactured by Shimadzu Corporation)
Column: Synergi (registered trademark) 4 μm Hydro-RP 80 Å, LC Column 250×4.6 mm, Ea (manufactured by Phenomenex)
Eluent: 20 mM potassium phosphate (pH 2.9)
Flow rate: 0.7 mL/min
Detection wavelength: 220 nm The degree of generation of a formate was evaluated by calculating a residual formic acid ratio in the film according to the following formula.

Residual formic acid ratio in film=(Total weight of formic acid extracted into methanol (g)/weight of film sample (g))×100(%)

Results are illustrated in Table 6.

TABLE 6

| | Modified fibroin | Residual formic acid ratio in film (%) |
|---|---|---|
| Reference Example 1 | PRT219 (SEQ ID NO: 24) | 0.9 |
| Example 7 | PRT1171 (SEQ ID NO: 25) | 0.1 |

It was confirmed that the protein film formed of the modified fibroin of Example 7 (PRT1171) having a lower serine residue content rate had a smaller residual formic acid ratio in the film and suppressed generation of a formate more than the protein film formed of the modified fibroin of Reference Example 1 (PRT219).

The invention claimed is:

1. A modified fibroin comprising a domain sequence represented by Formula 1: [(A)$_n$ motif-REP]$_m$ or Formula 2: [(A)$_n$ motif-REP]$_m$-(A)$_n$ motif, wherein a serine residue content rate is less than 5.5%, and wherein:

in Formula 1 and Formula 2, the (A)$_n$ motif represents an amino acid sequence consisting of 4 to 27 amino acid residues and the number of alanine residues with respect to the total number of amino acid residues in the (A)$_n$ motif is 80% or more, REP represents an amino acid sequence consisting of 10 to 200 amino acid residues, m represents an integer of 10 to 300, the plurality of (A)$_n$ motifs may be the same amino acid sequence or different amino acid sequences, and the plurality of REPs may be the same amino acid sequence or different amino acid sequences.

2. The modified fibroin according to claim 1, wherein a threonine residue content rate is 9% or less.

3. The modified fibroin according to claim 1, wherein a content rate of serine residue and threonine residue is 9% or less.

4. The modified fibroin according to claim 1, wherein the modified fibroin comprises: an amino acid sequence set forth in SEQ ID NO: 2, SEQ ID NO: 3, SEQ ID NO: 4, SEQ ID NO: 5, or SEQ ID NO: 28; or an amino acid sequence having 90% or more sequence identity with the amino acid sequence set forth in SEQ ID NO: 2, SEQ ID NO: 3, SEQ ID NO: 4, SEQ ID NO: 5, or SEQ ID NO: 28.

5. The modified fibroin according to claim 1, further comprising a tag sequence at either or both of an N-terminal and a C-terminal.

6. The modified fibroin according to claim 5, wherein the tag sequence includes an amino acid sequence set forth in SEQ ID NO: 17 or SEQ ID NO: 18.

7. The modified fibroin according to claim 1, wherein the modified fibroin comprises: an amino acid sequence set forth in SEQ ID NO: 10, SEQ ID NO: 11, SEQ ID NO: 12, SEQ ID NO: 13, or SEQ ID NO: 25; or an amino acid sequence having 90% or more sequence identity with the amino acid sequence set forth in SEQ ID NO: 10, SEQ ID NO: 11, SEQ ID NO: 12, SEQ ID NO: 13, or SEQ ID NO: 25.

8. A nucleic acid encoding the modified fibroin according to claim 1.

9. A nucleic acid hybridizing with a complementary strand of the nucleic acid according to claim 8 under hybridization conditions, wherein there is at least 85% or more identity between the sequences, and include at 42° C. using 5×SSC containing 0.5% SDS, and encoding a modified fibroin including a domain sequence represented by Formula 1: [(A) n motif-REP] m or Formula 2: [(A)~motif-REP]m-(A) n motif, and wherein: in Formula 1 and Formula 2, the (A) n motif represents an amino acid sequence consisting of 4 to 27 amino acid residues and the number of alanine residues with respect to the total number of amino acid residues in the (A) n motif is 80% or more, REP represents an amino acid sequence consisting of 10 to 200 amino acid residues, m represents an integer of 10 to 300, the plurality of (A) n motifs may be the same amino acid sequence or different amino acid sequences, and the plurality of REPs may be the same amino acid sequence or different amino acid sequences.

10. A nucleic acid having 90% or more sequence identity with the nucleic acid according to claim 8 and encoding a modified fibroin including a domain sequence represented by Formula 1: $[(A)_n$ motif-REP$]_m$ or Formula 2: $[(A)_n$ motif-REP$]_m$-$(A)_n$ motif, and wherein:

in Formula 1 and Formula 2, the (A) n motif represents an amino acid sequence consisting of 4 to 27 amino acid residues and the number of alanine residues with respect to the total number of amino acid residues in the (A) n motif is 80% or more, REP represents an amino acid sequence consisting of 10 to 200 amino acid residues, m represents an integer of 10 to 300, the plurality of (A) n motifs may be the same amino acid sequence or different amino acid sequences, and a plurality of REPs may be the same amino acid sequence or different amino acid sequences.

11. An expression vector comprising: the nucleic acid sequence according to any of one of claims 8-10, and one or more regulatory sequences operably linked thereto.

12. A host transformed with the expression vector according to claim 11.

13. The host according to claim 12, which is a prokaryote.

14. The host according to claim 12, which is a eukaryote.

15. An artificially modified fibroin composition comprising the modified fibroin according to claim 1.

16. The artificially modified fibroin composition according to claim 15, which is a protein powder.

17. The artificially modified fibroin composition according to claim 15, which is a doping liquid.

18. The artificially modified fibroin composition according to claim 15, which is a fiber.

19. The artificially modified fibroin composition according to claim 15, which is a film.

20. A method for producing a modified fibroin, the method comprising a step in which a host transformed with an expression vector including a nucleic acid sequence encoding a modified fibroin and one or a plurality of regulatory sequences operably linked to the nucleic acid sequence expresses the nucleic acid, wherein the modified fibroin is the modified fibroin according to claim 1.

21. A method for producing an artificially modified fibroin composition containing a modified fibroin, the method comprising a step of preparing a modified fibroin, wherein the modified fibroin is the modified fibroin according to claim 1.

22. The production method according to claim 20, further comprising a step of bringing the modified fibroin into contact with a carboxylic acid.

23. The production method according to claim 21, further comprising a step of adjusting a modified fibroin solution containing the modified fibroin with a carboxylic acid.

24. A product comprising the modified fibroin according to claim 1, the product being selected from the group consisting of a fiber, a yarn, a film, a foam, a grain, a nanofibril, a gel, and a resin.

* * * * *